US011168347B2

(12) United States Patent
Ismagilov et al.

(10) Patent No.: US 11,168,347 B2
(45) Date of Patent: Nov. 9, 2021

(54) DIGITAL QUANTIFICATION OF DNA REPLICATION AND/OR CHROMOSOME SEGREGATION BASED DETERMINATION OF ANTIMICROBIAL SUSCEPTIBILITY

(71) Applicant: CALIFORNIA INSTITUTE OF TECHNOLOGY, Pasadena, CA (US)

(72) Inventors: Rustem F. Ismagilov, Altadena, CA (US); Nathan G. Schoepp, Pasadena, CA (US); Travis S. Schlappi, Pasadena, CA (US); Matthew S. Curtis, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 91 days.

(21) Appl. No.: 15/715,086

(22) Filed: Sep. 25, 2017

(65) Prior Publication Data

US 2018/0105859 A1 Apr. 19, 2018

Related U.S. Application Data

(60) Provisional application No. 62/460,625, filed on Feb. 17, 2017, provisional application No. 62/399,196, filed on Sep. 23, 2016.

(51) Int. Cl.
C12Q 1/18 (2006.01)
C12Q 1/6851 (2018.01)
C12Q 1/10 (2006.01)

(52) U.S. Cl.
CPC ............ *C12Q 1/18* (2013.01); *C12Q 1/10* (2013.01); *C12Q 1/6851* (2013.01)

(58) Field of Classification Search
CPC ............................. C12Q 1/18; C12Q 1/6851
See application file for complete search history.

(56) References Cited

U.S. PATENT DOCUMENTS

| | | | |
|---|---|---|---|
| 5,789,173 A | 8/1998 | Peck et al. | |
| 6,153,400 A | 11/2000 | Matsumura et al. | |
| 6,391,577 B1 | 5/2002 | Mikkelsen et al. | |
| 7,728,119 B2 | 6/2010 | Nakamura et al. | |
| 8,476,063 B2 | 7/2013 | Jovanovich et al. | |
| 9,133,498 B2 | 9/2015 | Kwon et al. | |
| 9,415,392 B2 | 8/2016 | Ismagilov et al. | |
| 9,447,461 B2 | 9/2016 | Ismagilov et al. | |
| 9,464,319 B2 | 10/2016 | Ismagilov et al. | |
| 9,493,826 B2 | 11/2016 | Ismagilov et al. | |
| 9,687,845 B2 | 6/2017 | Weibel et al. | |
| 9,803,237 B2 | 10/2017 | Ismagilov et al. | |
| 9,808,798 B2 | 11/2017 | Ismagilov et al. | |
| 9,822,356 B2 | 11/2017 | Ismagilov et al. | |
| 2005/0095665 A1 | 5/2005 | Williams et al. | |
| 2009/0181395 A1 | 7/2009 | Becker et al. | |
| 2011/0269130 A1 | 11/2011 | Shi et al. | |
| 2012/0010091 A1 | 1/2012 | Linnarson | |
| 2012/0028342 A1 | 2/2012 | Ismagilov et al. | |
| 2012/0100551 A1 | 4/2012 | Kojima et al. | |
| 2012/0329038 A1 | 12/2012 | Ismagilov et al. | |
| 2013/0052653 A1 | 2/2013 | Stein et al. | |
| 2013/0190196 A1 | 7/2013 | Onderdonk et al. | |
| 2013/0281316 A1 | 10/2013 | Ismagilov et al. | |
| 2013/0288249 A1 | 10/2013 | Gullberg et al. | |
| 2013/0309679 A1 | 11/2013 | Ismagilov et al. | |
| 2014/0278136 A1 | 9/2014 | Shamsheyeva et al. | |
| 2014/0308663 A1 | 10/2014 | Yonekawa et al. | |
| 2014/0323340 A1 | 10/2014 | Goldberg et al. | |
| 2014/0336064 A1 | 11/2014 | Ismagilov et al. | |
| 2015/0104789 A1 | 4/2015 | Haake et al. | |
| 2015/0159205 A1 | 6/2015 | Narayanan et al. | |
| 2015/0225803 A1 | 8/2015 | Ismagilov et al. | |
| 2015/0247190 A1 | 9/2015 | Ismagilov et al. | |
| 2015/0267266 A1 | 9/2015 | Soetaert et al. | |
| 2016/0138072 A1 | 5/2016 | Talebpour et al. | |
| 2016/0160268 A1 | 6/2016 | Haake et al. | |
| 2016/0256870 A1 | 9/2016 | Ismagilov et al. | |
| 2016/0263577 A1 | 9/2016 | Ismagilov et al. | |
| 2016/0288121 A1 | 10/2016 | Ismagilov et al. | |
| 2016/0362734 A1 | 12/2016 | Ismagilov et al. | |
| 2017/0225161 A1 | 8/2017 | Begolo et al. | |
| 2018/0105859 A1 | 4/2018 | Ismagilov et al. | |
| 2019/0194726 A1 | 6/2019 | Ismagilov et al. | |

FOREIGN PATENT DOCUMENTS

| | | |
|---|---|---|
| CN | 206089692 U | 4/2017 |
| JP | 2001299388 A | 10/2001 |
| KR | 101779038 B1 | 9/2017 |
| WO | 2010/111265 A1 | 9/2010 |

(Continued)

OTHER PUBLICATIONS

Glossary entry for "Dalton" in Lodish H, Berk A, Zipursky SL, et al. Molecular Cell Biology. 4th edition. New York: W. H. Freeman; 2000. Available from: https://www.ncbi.nlm.nih.gov/books/NBK21475/, printed as p. 1/1. (Year: 2000).*
Glossary entry for "replication origin" in Lodish H, Berk A, Zipursky SL, et al. Molecular Cell Biology. 4th edition. New York: W. H. Freeman; 2000. Available from: https://www.ncbi.nlm.nih.gov/books/NBK21475/, printed as p. 1/1. (Year: 2000).*
Glossary entry for "base pair" in Lodish H, Berk A, Zipursky SL, et al. Molecular Cell Biology. 4th edition. New York: W. H. Freeman; 2000. Available from: https://www.ncbi.nlm.nih.gov/books/NBK21475/, printed as p. 1/1. (Year: 2000).*
Li et al. Picoliter well array chip-based digital recombinase polymerase amplification forabolute quantification of nucleic acids. PLOS ONE, vol. 11, No. 4, E0153359, Apr. 13, 2016, printed as p. Jan. 15, 15/15, including p. 1/3-3/3 of Supporting Information. (Year: 2016).*
Kalsi et al. Rapid and sensitive detection of antibiotic resistance on a programmable digital microfluidic platform. Lab on a Chip, vol. 15, pp. 3065-3075, Jun. 18, 2015, including p. 1/2-2/2 of Supplementary Material. (Year: 2015).*

(Continued)

*Primary Examiner* — Jennifer Dunston

(74) *Attorney, Agent, or Firm* — Steinfl + Bruno LLP

(57) ABSTRACT

Disclosed herein are methods and devices for using digital isothermal amplification to detect subtle responses to environmental stimuli, such as detecting antibiotic susceptibility using digital quantification of DNA replication and/or chromosome segregation.

21 Claims, 21 Drawing Sheets

Specification includes a Sequence Listing.

(56) References Cited

FOREIGN PATENT DOCUMENTS

| WO | WO 2010117620 | 10/2010 |
|---|---|---|
| WO | 2012/148477 A1 | 11/2012 |
| WO | 2013/072069 A1 | 5/2013 |
| WO | WO 2013/130875 A1 | 9/2013 |
| WO | WO 2013159116 | 10/2013 |
| WO | WO 2013159117 | 10/2013 |
| WO | WO 2014055963 | 4/2014 |
| WO | WO 2014172688 | 10/2014 |
| WO | WO 2015009967 | 1/2015 |
| WO | WO 2015013324 | 1/2015 |
| WO | WO 2015058008 | 4/2015 |
| WO | WO 2015084458 | 6/2015 |
| WO | WO 2016/011280 | 1/2016 |
| WO | WO 2016085632 | 6/2016 |
| WO | 2017/127727 A1 | 7/2017 |
| WO | 2018/111630 A2 | 6/2018 |
| WO | 2019/075264 A1 | 4/2019 |
| WO | 2020/028718 A1 | 2/2020 |

OTHER PUBLICATIONS

Assmann, et al. "Identification of vancomycin interaction with Enterococcus faecal is within 30 min of interaction time using Raman spectroscopy", Anal. Bioanal. Chern., vol. 407, 2015, pp. 8343-8352.

Bernhardt, et al. "Detection of Bacteria in Blood by Centrifugation and Filtration" J. Clinical Microbiology, vol. 29, No. 3, 1991, pp. 422-425.

Besant, et al. "Rapid electrochemical phenotypic profiling of antibiotic-resistant bacteria" Lab Chip, vol. 15, May 2015, pp. 2799-2807.

Beuving, et al. "Antibiotic Susceptibility Testing of Grown Blood Cultures by Combining Culture and Real-Time Polymerase Chain Reaction Is Rapid and Effective" PLoS ONE, vol. 6, No. 12, 2011, pp. e27689.

Blattner, et al. "The Complete Genome Sequence of *Escherichia coli* K-12" Science, vol. 277, 1997, pp. 1453-1462.

Boedicker, et al. "Microfluidic Confinement of Single Cells of Bacteria in Small Volumes Initiates High-Density Behavior of Quorum Sensing and Growth and Reveals Its Variability" Agnew. Chern. Int. Ed., vol. 48, 2009, pp. 5908-5911. Including Supporting Information.

Boedicker, J. et al., "Detecting Bacteria and Determining Their Susceptibility to Antibiotics by Stochastic Confinement in Nanoliter Droplets Using Plug-Based Microfluidics," Lab on a Chip, vol. 8, No. 8, Jan. 1, 2008, pp. 1265-1272.

Brunschede, et al. "Establishment of exponential growth after a nutritional shift-up in *Escherichia coli* B/r: Accumulation of deoxyribonucleic acid, ribonucleic acid, and protein" J. Bacteriology, vol. 129, No. 2, 1977, pp. 1020-1033.

Cartron, et al. "Feo—Transport of ferrous iron into bacteria" BioMetals, vol. 19, 2006, pp. 143-157.

Churski, et al. "Rapid screening of antibiotic toxicity in an automated microdroplet system" Lab Chip, vol. 12, 2012, pp. 1629-1637.

Cirz, et al. "Inhibition of Mutation and Combating the Evolution of Antibiotic Resistance" PLoS Biology, vol. 3, No. 6, 2005, p. e176.

Couturier and Rocha. "Replication-associated gene dosage effects shape the genomes of fast-growing bacteria but only fortranscription and translation genes" Molecular Microbiology, vol. 59, No. 5, 2006, pp. 1506-1518.

Donachie and Blakely. "Coupling the initiation of chromosome replication to cell size in *Escherichia coli*" Cur. Opin. Microbioloov, vol. 6, 2003, pp. 146-150.

Drlica and Zhao. "DNA gyrase, topoisomerase IV, and 4-quinolones" Microbial. Mol. Biology Rev., vol. 61, No. 3, 1997, pp. 377-392.

Dwyer, et al. "Antibiotics induce redox-related physiological alterations as part of their lethality" PNAS, vol. 111, No. 20, May 2014, pp. E100-E109.

European Patent Office, Extended European Search Report, EP Patent Application No. 15862888.3, dated Jul. 9, 2018, nine pages.

Fossum, et al. "Organization of sister origins and replisomes during multifork DNA replication in *Escherichia coli*" EMBO Journal, vol. 26, 2007, pp. 4514-4522.

Geiss, et al. "Direct multiplexed measurement of gene expression with color-coded probe pairs" Nature Biotech., vol. 26, No. 3, 2008, pp. 317-325. Including Corrigendum.

Hagiwara, et al. "A Genome-Wide View of *Escherichia coli* BasS-BasR Two-component System Implicated in Iron-responses" Bioscience, Biotechnology and Biochemistry, vol. 68, No. 8, 2004, pp. 1758-1767.

Intellectual Property Office of Singapore, Search Report and Invitation to Respond to Written Opinion, Singapore Patent Application No. 11201703695V, dated May 8, 2018, 10 pages.

Jeon, et al. "RstA-Promoted Expression of the Ferrous Iron Transporter FeoB under Iron-Replete Conditions Enhances Fur Activity in *Salmonella enterica*" J. Bacteriology, vol. 190, No. 2, 2008, pp. 7326-7334.

Joshi, et al. "*Escherichia coli* sister chromosome separation includes an abrupt global transition with concomitant release of late-splitting intersister snaps" PNAS, vol. 108, No. 7, 2011, pp. 2765-2770.

Kang, et al. "An extracorporeal blood-cleansing device for sepsis therapy" Nature Med., vol. 20, No. 10, Oct. 2014, pp. 1211-1216.

Kang, et al. "Rapid detection of single bacteria in unprocessed blood using Integrated Comprehensive Droplet Digital Detection" Nature Communications, Nov. 2014, pp. 1-10.

Kempf, et al. "Fluorescent In Situ Hybridization Allows Rapid Identification of Microorganisms in Blood Cultures" J. Clin. Microbial., vol. 38, No. 2, 2000, pp. 830-838.

Kubitschek and Freedman "Chromosome Replication and the Division Cycle of *Escherichia coli* B/r" J. Bacteriology, vol. 107, No. 1, 1971, pp. 95-99.

Lehman, et al. "A multiplex real-time PCR assay for rapid detection and differentiation of 25 bacterial and fungal pathogens from whole blood samples" Med Microbial Immunol, vol. 197, 2008, pp. 313-324.

Lobritz, et al. "Antibiotic efficacy is linked to bacterial cellular respiration" PNAS, vol. 12, No. 27, Jul. 2015, pp. 8173-8180.

Ma, et al. "Gene-targeted microfluidic cultivation validated by isolation of a gut bacterium listed in Human Microbiome Project's Most Wanted taxa" PNAS, vol. 111, No. 27, Jul. 2014, pp. 9768-9773.

Ma, et al. "Individually addressable arrays of replica microbial cultures enabled by splitting SlipChips" Integr Biol, vol. 6, 2014, pp. 796-805. Including Supporting Information.

Mann and Mikkelson "Antibiotic Susceptibility Testing at a Screen-Printed Carbon Electrode Array" Anal Chem, vol. 80, 2008, pp. 843-848.

Millar, et al. "A simple and sensitive method to extract bacterial, yeast and fungal DNA from blood culture material" J Microbial Methods, vol. 42, 2000, pp. 139-147.

PCT International Search Report & Witten Opinion, International Application No. PCT/US2015/059344, dated Jul. 12, 2016, 20 Pages.

Shen, et al. "Digital PCR on a SlipChip" Lab Chip, vol. 10, 2010, pp. 2666-2672.

Shishkin, et al. "Simultaneous generation of many RNA-seg libraries in a single reaction." Nat Meth, vol. 12, 2014, pp. 323-325.

Slager, et al. "Antibiotic-induced replication stress triggers bacterial competence by increasing gene dosage near the origin." Cell, vol. 157, 2014, pp. 395-406.

Tamayo, et al. "Rapid assessment of the effect ofciprofloxacin on chromosomal DNA from *Escherichia coli* using an in situ DNA fragmentation assay." BMC Microbial, vol. 9, 2009, p. 69.

Touati, et al. "Lethal oxidative damage and mutagenesis are generated by iron in delta-fur mutants of *Escherichia coli*: Protective role of superoxide dismutase." J Bacter, vol. 177, 1995, pp. 2305-2314.

Weaver, et al. "Taking qPCR to a higher level: Analysis of CNV reveals the power of high throughput qPCR to enhance quantitative resolution." Methods, vol. 50, 2010, pp. 271-276.

(56) References Cited

OTHER PUBLICATIONS

Wecke and Masch Er "Antibiotic research in the age of omics: from expression profiles to interspecies communication." J. Antimicrob Chemo, vol. 66, 2011, pp. 2689-2704.
Zierdt "Simplified Lysed-Blood Culture Technique" J Clin Microbial, vol. 23, No. 3, 1986, pp. 452-455.
Zierdt, et al. "Development of lysis-filtration blood culture technique." J Clin Microbial, vol. 5, 1977, pp. 46-50.
PCT International Search Report and Written Opinion for PCT/US17/53338, dated Jan. 30, 2018, 25 Pages.
PCT International Search Report and Written Opinion for PCT/US2017/061403, dated Feb. 13, 2018, 16 Pages.
Pholwat et al.," Digital PCR to Detect and Quantify Heteroresistance in Drug Resistant Mycobacterium tuberculosis", PLoS One, Feb. 2013, vol. 8, No. 2, e57238, pp. 1-10.
United States Patent Office, Office Action, U.S. Appl. No. 15/524,449, filed Apr. 11, 2019, 21 pages.
Barczak, A. K., "RNA signatures allow rapid identification of pathogens and antibiotic susceptibilities," Proc Natl Acad Sci U S A, Apr. 17, 2012, vol. 109, No. 16, pp. 6217-6222.
Chantell C., "Multiplexed automated digital microscopy for rapid identification and antimicrobial susceptibility testing of bacteria and yeast directly from clinical samples," Clinical Microbiology Newsletter, Oct. 15, 2015, vol. 37, No. 20, pp. 161-167.
Choi, J., et al., "A rapid antimicrobial susceptibility test based on single-cell morphological analysis," Sci Transl Med., Dec. 17, 2014, vol. 6, No. 267, 267ra174, pp. 1-15.
Davies, J., et al., "Origins and evolution of antibiotic resistance," Microbiol Mol Biol Rev., Sep. 2010, vol. 74, No. 3, pp. 417-433.
Douglas, I.S., et al., "Rapid automated microscopy for microbiological surveillance of ventilator-associated pneumonia," Am J Respir Crit Care Med., Mar. 1, 2015, vol. 191, No. 5, pp. 566-573.
Ertl, P., et al., "Rapid antibiotic susceptibility testing via electrochemical measurement of ferricyanide reduction by *Escherichia coli* and Clostridium sporogenes," Anal Chem., Oct. 15, 2000, vol. 72, No. 20, pp. 4957-4964.
Fredborg, M., et al., "Real-time optical antimicrobial susceptibility testing," J Clin Microbiol., Jul. 2013, vol. 51, No. 7, pp. 2047-2053.
Halford, C., et al., "Rapid antimicrobial susceptibility testing by sensitive detection of precursor rRNA using a novel electrochemical biosensing platform," Antimicrob Agents Chemother., Feb. 2013, vol. 57, No. 2, pp. 936-943.
Ikeuchi, T., et al., "PCR-based method for rapid and minimized electrochemical detection of mecA gene of methicillin-resistant *Staphylococcus aureus* and methicillin-resistant *Staphylococcus epidermidis*," General Medicine: Open Access. 2015, vol. 3, No. 6, pp. 1-5.
Jorgensen, J.H., et al., "Antimicrobial susceptibility testing: a review of general principles and contemporaiy practices," Clin Infect Dis., Dec. 2009, vol. 49, No. 11, pp. 1749-1755.
Kostic, T., et al., "Thirty-minute screening of antibiotic resistance genes in bacterial isolates with minimal sample preparation in static self-dispensing 64 and 384 assay cards," Appl Microbiol Biotechnol., Jul. 31, 2015, vol. 99, No. 18, pp. 7711-7722.
Kreutz, J.E., et al.," Theoretical Design and Analysis of Multivolume Digital Assays with Wide Dynamic Range Validated Experimentally with Microfluidic Digital PCR," Analytical Chemistiy, Oct. 2011, vol. 83, pp. 8158-8168.
Kumar, A., et al., "Duration of hypotension before initiation of effective antimicrobial therapy is the critical determinant of survival in human septic shock," Crit Care Med. 2006, vol. 34, No. 6, pp. 1589-1596.
Kurosaki, Y., et al., "Development and Evaluation of Reverse Transcription-Loop-Mediated Isothermal Amplification (RT-LAMP) Assay Coupled with a Portable Device for Rapid Diagnosis of *Ebola* Virus Disease in Guinea," PLoS Negl Trap Dis., Feb. 22, 2016, vol. 10, No. e0004472, pp. 1-12.
Mach, K.E., et al., "A biosensor platform for rapid antimicrobial susceptibility testing directly from clinical samples," J Urol,, Jan. 2011, vol. 185, No. 1, pp. 148-153.

Marston, H.D., et al., "Antimicrobial Resistance," JAMA. Sep. 20, 2016, vol. 316, No. 11, pp. 1193-1204.
Mezger, A., et al., "A general method for rapid determination of antibiotic susceptibility and species in bacterial infections," J Clin Microbiol., Feb. 2015, vol. 53, No. 2, pp. 425-432.
Peterson, L.R., et al., "Methicillin-Resistant *Staphylococcus aureus* Control in the 21st Century: Laboratory Involvement Affecting Disease Impact and Economic Benefit from Large Population Studies," J Clin Microbiol., Nov. 2016, vol. 54, No. 11, pp. 2647-2654.
Rolain, J.M., et al., "Real-time PCR for universal antibiotic susceptibility testing," J Antimicrob Chemother., Jul. 2004, vol. 54, No. 2, pp. 538-541.
Schlappi, T., et al., "Flow-through Capture and in Situ Amplification Can Enable Rapid Detection of a Few Single Molecules of Nucleic Acids from Several Milliliters of Solution." Analytical Chemistry, Jul. 2016, vol. 88, No. 15, pp. 7647-7653.
Schoepp, N.G., et al., "Digital Quantification of DNA Replication and Chromosome Segregation Enables Determination of Antimicrobial Susceptibility after only 15 Minutes of Antibiotic Exposure," Angew Chern Int Ed Engl., 2016, vol. 55, No. 33, pp. 9557-9561.
Shen, F., et al., "Nanoliter multiplex PCR arrays on a SlipChip," Analytical chemistry, Jun. 1, 2010, vol. 82, No. 11, pp. 4606-4612.
Shen, F., et al., "Digital Isothermal Quantification of Nucleic Acids via Simultaneous Chemical Initiation of Recombinase Polymerase Amplification Reactions on SlipChip," Analytical Chemistry, Apr. 8, 2011, vol. 83, pp. 3533-3540.
Spencer, M., et al., "A primer on on-demand polymerase chain reaction technology," Am J Infect Control, 2015, vol. 43, No. 10, pp. 1102-1108.
Steinberger-Levy, I., et al., "A Rapid Molecular Test for Determining Yersinia pestis Susceptibility to Ciprofloxacin by the Quantification of Differentially Expressed Marker Genes," Frontiers in Microbiology, May 2016, vol. 7, pp. 1-13.
Van der Zee, A., et al., "Review of a major epidemic of methicillin-resistant Staphylococcus aureus: the costs of screening and consequences of outbreak management," Am J Infect Control. 2013, vol. 41, No. 3, pp. 204-209.
Whale, A. S., et al., "Comparison of microfluidic digital PCR and conventional quantitative PCR for measuring copy number variation," Nucleic Acids Res., Feb. 28, 2012, vol. 40, No. 11, e82, pp. 1-9.
Zboromyrska, Y., et al., "Rapid detection of beta-lactamases directly from positive blood cultures using a loop-mediated isothermal amplification (LAMP)-based assay," Int J Antimicrob Ag., Mar. 4, 2015, vol. 46, No. 3, pp. 355-356.
PCT Invitation to Pay Additional Fees for PCT/US17/53338, dated Nov. 30, 2017, 3 Pages.
Aellen S. et al., "Detection of Live and Antibiotic-Killed Bacteria by Quantitative Real-Time PCR of Specific Fragments of rRNA" Antimicrobial Agents and Chemotherapy, Jun. 2006, pp. 1913-1920.
Ahn H. et al., "Single-Step Recombinase Polymerase Amplification Assay Based on a Paper Chip for Simultaneous Detection of Multiple Foodborne Pathogens." Anal Chern,(2018).
Allan-Blitz L.T. et al., "Wild-Type Gyrase A Genotype of Neisseria gonorrhoeae Predicts In Vitro Susceptibility to Ciprofloxacin: A Systematic Review of the Literature and Meta-Analysis."*Sex Transm Dis*, 261-265 (2017).
Allen VG, et al. "Neisseria gonorrhoeae treatment failure and susceptibility to cefixime in Toronto, Canada." JAMA 309, 163-170 (2013).
Altschul S.F et al., "Basic local alignment search tool. "J Mol Biol, 1990. 215(3); p. 403-410.
Altschul S.F et al., "Gapped BLAST and PSI-BLAST: a new generation of protein database search programs "Nucleic Acids Res,1997. 25(17): p. 3389-3402.
Avesar, J., et al. "Rapid phenotypic antimicrobial susceptibility testing using nanoliter arrays." Proceedings of the National Academy of Sciences 114(29): E5787. (2017).

(56) References Cited

OTHER PUBLICATIONS

B. Sun, et al., "Measuring fate and rate of single-molecule competition of amplification and restriction digestion, and its use for rapid genotyping tested with hepatitis C viral RNA." Angew. Chern. Int. Ed. Engl. 53, 8088-8092 (2014).

Badshah S.L. et al., "New developments in non-quinolone-based antibiotics for the inhibition of bacterial gyrase and topoisomerase IV."*Eur J Med Chem*,2018. 152: p. 393-400.

Baker, et al., "Review and re-analysis of domain-specific 16S primers" Journal of Microbiological Methods, 541-555, 2003.

Balashov S. et al., "Multiplex bead suspension array for screening Neisseria gonorrhoeae antibiotic resistance genetic determinants in noncultured clinical samples." J Mol Diagn 15, 116-129 (2013).

Baltekin, 0., et al. "Antibiotic susceptibility testing in less than 30 min using direct single-cell imaging." Proc Natl Acad Sci US A 114(34): 9170-9175. (2017).

Banoo, S., et al. "Evaluation of diagnostic tests for infectious diseases: general principles." Nat Rev Microbiol 4(9 Suppl): S21-31. (2006).

Bard J.D. "Why Can't We Just Use PCR? The Role of Genotypic versus Phenotypic Testing for Antimicrobial Resistance Testing." Clinical Microbiology Newsletter 40, 87-95 (2018).

Baumann, E., et al. "Hemolysis of human erythrocytes with saponin affects the membrane structure." Acta Histochem 102(1): 21-35. (2000).

Bernabeu S. et al., "Evaluation of the beta-CARBA test, a colorimetric test for the rapid detection of carbapenemase activity in Gram-negative bacilli." J Antimicrob Chemother 72, 1646-1658 (2017).

Bhattacharyya, R. P., et al. "Simultaneous detection of genotype and phenotype enables rapid and accurate antibiotic susceptibility determination." Nature Medicine 25(12): 1858-1864. (2019).

Blank, S. et al., "Neisseria gonorrhoeae—Rising Infection Rates, Dwindling Treatment Options." N Engl J Med 379(19): 1795-1797. (2018).

Bogaerts P. et al., "Evaluation of the BYG Carba Test, a New Electrochemical Assay for Rapid Laboratory Detection of Carbapenemase-Producing Enterobacteriaceae." J Clin Microbiol 54, 349-358(2016).

Bolan G.A., et al., "The emerging threat of untreatable gonococcal infection." N Engl J Med 366, 485-487 (2012).

Bou G, et al. "Fast assessment of resistance to carbapenems and ciprofloxacin of clinical strains of Acinetobacter baumannii." J Clin Microbiol 50, 3609-3613 (2012).

Buckley C, et al. "Real-time PCR detection of Neisseria gonorrhoeae susceptibility to penicillin." J Antimicrob Chemother 71, 3090-3095 (2016).

Burnham C.A et al., "Rapid ertapenem susceptibility testing and Klebsiella pneumoniae carbapenemase phenotype detection in Klebsiella pneumoniae isolates by use of automated microscopy of immobilized live bacterial cells." J Clin Microbiol 52, 982-986(2014).

Cacciapuoti, A F. et al., "Cell envelope of Neisseria gonorrhoeae: phospholipase activity and its relationship to autolysis." Infection and Immunity, vol. 2, No. 2, pp. 418-420 (1978).

Cady N. , "Quantum Dot Molecular Beacons for DNA Detection" Methods Mol Biol 554:367-79, 2009.

Cai S. "Phosphorothioated Primers Lead to Loop-Mediated Isothermal Amplification at Low Temperatures." Anal Chem 90, 8290-8294 (2018).

Cansizoglu, M. F., et al. "Rapid ultrasensitive detection platform for antimicrobial susceptibility testing." PLOS Biology 17(5): e3000291. (2019).

CDC—Agar Dilution Antimicrobial Susceptibility Testing. (2013).
CDC. Antibiotic Resistance Threats in the United States. (2013).
CPC. "Antibiotic/Antimicrobial Resistance: Biggest Threats and Data."(2019).
CDC. Sexually Transmitted Pisease Surveillance.(2017).
CDC. Sexually Transmitted Piseases Treatment Guidelines. In: Morbidity and Mortality Weekly Report (2015).

Cerqueira GC, et al. "Multi-institute analysis of carbapenem resistance reveals remarkable diversity, unexplained mechanisms, and limited clonal outbreaks." Proc Natl Acad Sci U S A 114, 1135-1140 (2017).

Chakravorty, S., et al., "A detailed analysis of 16S ribosomal RNA gene segments for the diagnosis of pathogenic bacteria." J Microbiol Methods, 69(2): p. 330-339.2007.

Chang YY, et al. "Clinical features of patients with carbapenem nonsusceptible Klebsiella pneumoniae and *Escherichia coli* in intensive care units: a nationwide multicenter study in Taiwan." J Microbiol Immunol Infect 48, 219-225 (2015).

Charalampous, T., et al. "Nanopore metagenomics enables rapid clinical diagnosis of bacterial lower respiratory infection." Nature Biotechnology 37(7): 783-792.(2019).

Chen, C.Y. et al., "A 6 x 6 drop plate method for simultaneous colony counting and MPN enumeration of Campylobacter jejuni, Listeria monocytogenes, and *Escherichia coli*." J Microbiol Methods, 55(2): p. 475-479.2003.

Chen L. et al., "Direct-qPCR Assay for Coupled Identification and Antimicrobial Susceptibility Testing of Neisseria gonorrhoeae." ACS Infect Dis 4, 1377-1384 (2018).

Chen Y., "Polymeric Sequence Probe for Single DNA Detection." Analytical chemistry 83.19 (2011): 7250-7254.

Chern E.C. et al., "Comparison of quantitative PCR assays for *Escherichia coli* targeting ribosomal RNA and single copy genes." Lett Appl Microbiol 52, 298-306 (2011).

Chesson H. W. et al., "An Illustration of the Potential Health and Economic Benefits of Combating Antibiotic-Resistant Gonorrhea." Sex Transm Dis 45, 250-253(2018).

Cho S. et al., "Smartphone-based, sensitive microPAD detection of urinary tract infection and gonorrhea." Biosens Bioelectron 74, 601-611(2015).

Cissell et al., "Resonance energy transfer methods of RNA detection" Anal Bioanal Chern 393(1 ):125-35, 2009.

Clifford, et al., "Detection of Bacterial 16S rRNA and Identification of Four Clinically Important Bacteria by Real-Time PCR" PLoS ONE, e48558, 2012.

CLSI. "M07-A10; Methods for Dilution Antimicrobial Susceptibility Testing for Bacteria That Grow Aerobically; Approved Standard-Tenth Edition." Clinical and Laboratory Standards Institute, 950 West Valley Road, Suite 2500, Wayne, Pennsylvania 19087 USA(2015).

CLSI. "M100-S25 Performance Standards for Antimicrobial Susceptibility Testing." CLSI 35,(2015).

Collin F. et al., "Exploiting bacterial DNA gyrase as a drug target: current state and perspectives."*Appl Microbial Biotechnol*,2011. 92(3): p. 479-497.

Communication of European publication number and information on the application of Article 67(3) EPC for EP Application No. 18866873 filed on behalf of California Institute of Technology Mail Date: Jul. 22, 2020.

Conesa, A., et al., "A survey of best practices for RNA-seq data analysis." Genome Biol, 17: p. 13.2016. 19 pages.

Cortegiani A., et al. "Use of Cepheid Xpert Carba-R(R) for Rapid Detection of Carbapenemase-Producing Bacteria in Abdominal Septic Patients Admitted to Intensive Care Unit." PLoS One 11, eQ160643 (2016).

Craw P. et al., "Isothermal nucleic acid amplification technologies for point-of-care diagnostics: a critical review," Lab Chip, 2012, 12, 2469-2486.

Daher R.K. "Recombinase Polymerase Amplification for Diagnostic Applications." Clin Chem 62, 947-958 (2016).

Davidsen T. et al., "Genetic interactions of DNA repair pathways in the pathogen Neisseria meningitidis." *J Bacteriol*,2007. 189(15): p. 5728-5737.

Davidsen T. et al., "Meningococcal genome dynamics"*Nat Rev Microbiol*,2006. 4(1): p. 11-22.

Demchick P. et al., "The permeability of the wall fabric of *Escherichia coli* and Bacillus subtilis." J Bacteriol 178, 768-773 (1996).

Deshayes S, et al. "Designing Hybrid Antibiotic Peptide Conjugates To Cross Bacterial Membranes." Bioconjug Chem 28, 793-804(2017).

Dijkstra A.J. "Peptidoglycan as a barrier to transenvelope transport." Journal of Bacteriology 178, 5555-5562 (1996).

(56) References Cited

OTHER PUBLICATIONS

Dillard J.P. et al., "A peptidoglycan hydrolase similar to bacteriophage endolysins acts as an autolysin in Neisseria gonorrhoeae." Molecular Microbiology 25, 893-901 (1997).
Dona V, et al. "Mismatch Amplification Mutation Assay-Based Real-Time PCR for Rapid Detection of Neisseria gonorrhoeae and Antimicrobial Resistance Determinants in Clinical Specimens." *J Clin Microbiol* 56,(2018).
Elmros, T. et al., "Autolysis of Neisseria gonorrhoeae." Journal of Bacteriology, pp. 969-976 (May 1976).
Etayash, H., et al. "Microfluidic cantilever detects bacteria and measures their susceptibility to antibiotics in small confined volumes." Nat Commun 7: 12947.(2016).
EUCAST. "European Committee on Antimicrobial Susceptibility Testing: Breakpoint Tables for Interpretation of MICs and Zone Diameters" (ver. 7.1). (2017).
Extended European Search Report for EP Application No. 18866873.5 filed on Oct. 11, 2018 on behalf of California Institute of Technology, dated Jul. 13, 2021 9 pages.
Eyre DW, et al. "Gonorrhoea treatment failure caused by a Neisseria gonorrhoeae strain with combined ceftriaxone and high-level azithromycin resistance", England,Feb. 2018. Euro Surveill 23.
Faria-Ramos I, et al. "A novel flow cytometric assay for rapid detection of extended-spectrum beta-lactamases." Clin Microbiol Infect 19, E8-E15 (2013).
FDA. "Evaluation of Automatic Class III Designation for T2Candida Panel and T2Dx Instrument."(2014).
Felix H. "Permeabilized cells." Anal Biochem 120, 211-234(1982).
Fernandez L. et al., "Adaptive and mutational resistance: role of porins and efflux pumps in drug resistance."*Clinical Microbiology Reviews*,2012. 25(4): p. 661-681.
Fifer H, et al. "Failure of Dual Antimicrobial Therapy in Treatment of Gonorrhea." N Engl J Med 374, 2504-2506(2016).
Fingerhuth S M. et al., "Detection of antibiotic resistance is essential for gonorrhoea point-of-care testing: a mathematical modelling study." BMC Med 15, 142 (2017).
Foerster S. et al., "A new rapid resazurin-based microdilution assay for antimicrobial susceptibility testing of Neisseria gonorrhoeae."*J Antimicrob Chemother*72, 1961-1968 (2017).
Foerster S et al., "Time-kill curve analysis and pharmacodynamic modelling for in vitro evaluation of antimicrobials against Neisseria gonorrhoeae." BMC Microbiol 16, 216(2016).
Gao Q. et al., "Gene expression diversity among *Mycobacterium tuberculosis* clinical isolates."*Microbiology*,2005.151(1): p. 5-14.
Garcia, D.L. et al., "AmiC functions as an N-acetylmuramyl-L-alanine amidase necessary for cell separation and can promote autolysis in Neisseria gonorrhoeae." Journal of Bacteriology, vol. 188, No. 20, pp. 7211-7221 (Oct. 2006).
Gaydos CA, et al. "Performance of the Cepheid CT/NG Xpert Rapid PCR Test for Detection of Chlamydia trachomatis and Neisseria gonorrhoeae."*J Clin Microbiol* 51, 1666-1672 (2013).
Gelband, H., et al. "State of the World's Antibiotics." CDDEP: Washington, D.C, HHS (2015).
Gianecini RA, et al. "Genome-based epidemiology and antimicrobial resistance determinants of Neisseria gonorrhoeae isolates with decreased susceptibility and resistance to extended-spectrum cephalosporins in Argentina in 2011-16." J Antimicrob Chemother, (2019).
Gomez J.E. et al., "Ribosomal mutations promote the evolution of antibiotic resistance in a multidrug environment."*Elife*,2017. 6. e20420. 25 pages.
Gootenberg, J.S., et al., "Multiplexed and portable nucleic acid detection platform with Cas13, Cas12a, and Csm6." Science, 360(6387): p. 439-444.Apr. 2018.
Gootenberg, U.S., et al., "Nucleic acid detection with CRISPR-Cas13a/C2c2." Science, 356(6336): p. 438-442.Apr. 2017.
Grad YH, et al. "Genomic Epidemiology of Gonococcal Resistance to Extended-Spectrum Cephalosporins, Macrolides, and Fluoroquinolones in the United States, 2000-2013." J Infect Dis 214, 1579-1587(2016).

Guh A.Y et al. "Epidemiology of Carbapenem-Resistant Enterobacteriaceae in 7 US Communities," 2012-2013. JAMA 314, 1479-1487(2015).
Hamilton, H.L. et al., "Natural transformation of Neisseria gonorrhoeae: From DNA donation to homologous recombination." Molecular Microbiology, 59(2), pp. 376-385 (2006).
Hansen, et al., "A Real-Time PCR-Based Semi-Quantitative Breakpoint to Aid in Molecular Identification of Urinary Tract Infections" PLoS ONE, e61439, 2013.
Harrison ST. "Bacterial cell disruption: a key unit operation in the recovery of intracellular products." Biotechnol Adv 9, 217-240 (1991).
Hawkey PM et al., "Carbapenem antibiotics for serious infections." BMJ 344, e3236 (2012).
Hebeler B.H. "Autolysis of Neisseria gonorrhoeae." J Bacteriol 122, 385-392(1975).
Hicks J.M. et al., "Recommendations and opinions for the use of point-of-care testing for hospitals and primary care: summary of a 1999 symposium." Clinica Chimica Acta 303, 1-17 (2001).
Honda S. et al., "Four-leaf clover qRT-PCR: A convenient method for selective quantification of mature tRNA."*RNA Biol*,2015. 12(5): p. 501-508.
Hou, et al. "Direct detection and drug-resistance profiling of bacteremias using inertial microfluidics" Lab Chip, vol. 15,2015, pp. 2297-2307.
Hu C, et al. "Ultra-fast electronic detection of antimicrobial resistance genes using isothermal amplification and Thin Film Transistor sensors." Biosens Bioelectron 96, 281-287 (2017).
International Preliminary Report on Patentability for International PCT Application No. PCT/US2019/044748 filed on Aug. 1, 2019 on behalf of California Institute of Technology, dated Feb. 11, 2021. 7 pages.
International Report on Patentability for International Application No. PCT/US2018/055501 filed Oct. 11, 2018, on behalf of California Institute of Technology, dated Apr. 23, 2020. 10 pages.
International Search Report for International Application No. PCT/US2018/055501 filed Oct. 11, 2018, on behalf of California Institute of Technology, dated Jan. 31, 2019. 4 pages.
International Search Report for International Application No. PCT/US2019/044748 filed on Aug. 1, 2019 on behalf of California Institute Of Technology, dated Nov. 29, 2019 5 pages.
Iovleva A. et al., "Carbapenem-Resistant Enterobacteriaceae." Clin Lab Med 37, 303-315(2017).
Jackman, J.E. et al., "Transfer RNA modifications: Nature's combinatorial chemistry playground." Wiley interdisciplinary reviews. RNA, 4(1): p. 35-48.2013.
Johnson L.S. et al., "Hidden Markov model speed heuristic and iterative HMM search procedure."*BMC Bioinformatics*,2010.11: p. 431.8 pages.
Kang, W., et al.. "Ultrafast Parallelized Microfluidic Platform for Antimicrobial Susceptibility Testing of Gram Positive and Negative Bacteria." Analytical Chemistry 91(9): 6242-6249. (2019).
Katz AR, et al. "Cluster of Neisseria gonorrhoeae Isolates With High-level Azithromycin Resistance and Decreased Ceftriaxone Susceptibility," Hawaii, 2016. Clin Infect Dis 65, 918-923 (2017).
Khazaei T. et al., "RNA markers enable phenotypic test of antibiotic susceptibility in Neisseria gonorrhoeae after 10 minutes of ciprofloxacin exposure"*Nature*,2018, pp. 1-10.
Kirkcaldy RD, et al. "Antimicrobial Drug Prescription and Neisseria gonorrhoeae Susceptibility, United States, 2005-2013." Emerg Infect Dis 23, 1657-1663(2017).
Kirkcaldy RD, et al. "Neisseria gonorrhoeae Antimicrobial Susceptibility Surveillance—The Gonococcal Isolate Surveillance Project, 27 Sites, United States, 2014." MMWR Surveill Summ 65, 1-19(2016).
Kohanski M.A et al., "How antibiotics kill bacteria: from targets to networks." Nat Rev Microbiol 8, 423-435 (2010).
Lange C. et al., "Quantitative matrix-assisted laser desorption ionization-time of flight mass spectrometry for rapid resistance detection." J Clin Microbiol 52, 4155-4162 (2014).
Lasserre C, et al. "Efficient Detection of Carbapenemase Activity in Enterobacteriaceae by Matrix-Assisted Laser Desorption Ionization-Time of Flight Mass Spectrometry in Less Than 30 Minutes." J Clin Microbiol 53, 2163-2171 (2015).

(56) References Cited

OTHER PUBLICATIONS

Lee SG, et al. "Various penA mutations together with mtrR, porB and ponA mutations in Neisseria gonorrhoeae isolates with reduced susceptibility to cefixime or ceftriaxone." J Antimicrob Chemother 65, 669-675 (2010).
Lee, S.R. et al., "Rapid one step detection of pathogenic bacteria in urine with sexually transmitted disease (STD) and prostatitis patient by multiplex PCR assay (mPCR)." J Microbiol, 45(5): p. 453-459. Oct. 2007.
Li et al., "Molecular beacons: An optimal multifunctional biological probe" Biochem Biophys Res Comm 373(4):457-61, 2008.
Li L. et al., "User-loaded SlipChip for equipment-free multiplexed nanoliter-scale experiments." J Am Chem Soc 132, 106-111 (2010).
Li Z. et al., "Rapid detection of quinolone resistanceassociated gyrA mutations in Neisseria gonorrhoeae with a LightCycler." J Infect Chemother 8, 145-150 (2002).
Liu, T., et al. "Rapid antimicrobial susceptibility testing with electrokinetics enhanced biosensors for diagnosis of acute bacterial infections." Ann Biomed Eng 42(11): 2314-2321. (2014).
Longo, G., et al. "Rapid detection of bacterial resistance to antibiotics using AFM cantilevers as nanomechanical sensors." Nat Nanotechnol 8(7): 522-526. (2013).
"M 100: Performance Standards for Antimicrobial Susceptibility Testing,"*Clinical and Laboratory Standards*Institute. 28th Edition. Jan. 2018. Excerpt, 2 Pages.
Magill SS, et al. "Prevalence of antimicrobial use in US acute care hospitals, May-Sep. 2011." JAMA 312, 1438-1446 (2014).
Marin M.A. et al., "The invasive Neisseria meningitidis MenC CC103 from Brazil is characterized by an accessory gene repertoire." *Sci Rep*,2017. 7(1): p. 1617. 11 pages.
Matsuda, K., et al., "Sensitive quantitative detection of commensal bacteria by rRNA targeted reverse transcription-PCR." Appl Environ Microbiol, 73(1): p. 32-39. Jan. 2007.
Mo, M., et al. "Rapid Antimicrobial Susceptibility Testing of Patient Urine Samples Using Large Volume Free Solution Light Scattering Microscopy." Analytical Chemistry 91(15): 10164-10171. (2019).
Morse, S. A. and B. H. Hebeler "Effect of pH on the growth and glucose metabolism of Neisseria gonorrhoeae." Infect Immun 21(1): 87-95. (1978).
Mu X, et al."Loop-mediated isothermal amplification: Rapid and sensitive detection of the antibiotic resistance gene ISAba1-blaOXA-51-like in Acinetobacter baumannii." J Microbiol Methods 121, 36-40 (2016).
Murata-Kamiya, N., et al. "Helicobacter pylori exploits host membrane phosphatidylserine for delivery, localization, and pathophysiological action of the CagA oncoprotein." Cell Host Microbe 7(5): 399-411.(2010).
Musta, A. C., et al. "Vancomycin MIC plus heteroresistance and outcome of methicillin-resistant *Staphylococcus aureus* bacteremia: trends over 11 years." J Clin Microbiol 47(6): 1640-1644. (2009).
Myhrvold, C., et al., "Field-deployable viral diagnostics using CRISPR-Cas13." Science, . 360(6387): p. 444-448.Apr. 2018.
Nadkarni, et al., "Determination of bacterial load by real-time PCR using a broad-range (universal) probe and primers set" Microbiology, 257-266, 2002.
Nakano R, et al. "Rapid detection of the Klebsiella pneumoniae carbapenemase (KPC) gene by loop-mediated isothermal amplification (LAMP)." J Infect Chemother 21, 202-206(2015).
Newman L, et al. "Global Estimates of the Prevalence and Incidence of Four Curable Sexually Transmitted Infections in 2012 Based on Systematic Review and Global Reporting."PLoSOne 10, e0143304(2015).
Newman L. M. et al., "Update on the management of gonorrhea in adults in the United States."*Clin Infect Dis* 44 Suppl3, S84-101 (2007).
Nikaido H. "Molecular basis of bacterial outer membrane permeability revisited." Microbiol Mol Biol Rev 67, 593-656 (2003).
O'Neill J. "Tackling Drug-Resistant Infections Globally: Final Report and Recommendations." (2016).
Ota Y, et al. "A rapid and simple detection method for phenotypic antimicrobial resistance in *Escherichia coli* by loop mediated isothermal amplification." J Med Microbiol, (2019).
Papp JR, et al. "Azithromycin Resistance and Decreased Ceftriaxone Susceptibility in Neisseria Gonorrhoeae," Hawaii, USA. Emerg Infect Dis 23, 830-832 (2017).
Park K et al., "FRET probe-based antibacterial susceptibility testing (F-AST) by detection of bacterial nucleases released by antibiotic-induced lysis." Biosensors and Bioelectronics,(2019).
Pearson W.R. et al., "Improved tools for biological sequence comparison."*Proc Natl Acad Sci USA*,1988. 85(8): p. 2444-2448.
Pearson W.R. "Searching protein sequence libraries: comparison of the sensitivity and selectivity of the Smith-Waterman and FASTA algorithms."*Genomics*, 1991. 11 (3): p. 635-650.
Phaneuf C.R. et al., "Rapid, Portable, Multiplexed Detection of Bacterial Pathogens Directly from Clinical Sample Matrices." Biosensors (Basel) 6, (2016).
Phillips E.A. "Strand Displacement Probes Combined with Isothermal Nucleic Acid Amplification for Instrument-Free Detection from Complex Samples." Anal Chern 90, 6580-6586 (2018).
Piddock LJ. "Assess drug-resistance phenotypes, not just genotypes." Nat Microbiol 1, 16120 (2016).
Pidgeon S.E. et al., "Vancomycin-Dependent Response in Live Drug-Resistant Bacteria by Metabolic Labeling." Angew Chern Int Ed Engl 56, 8839-8843 (2017).
Pink D. et al., "On the architecture of the gram-negative bacterial murein sacculus." J Bacteriol 182, 5925-5930 (2000).
Pollett S et al., "Phenotypic and molecular characteristics of carbapenem-resistant Enterobacteriaceae in a health care system in Los Angeles, California, from 2011 to 2013." J Clin Microbiol 52, 4003-4009(2014).
Poritz MA, et al. "FilmArray, an automated nested multiplex PCR system for multi-pathogen detection: development and application to respiratory tract infection." PLoS One 6, e26047 (2011).
Premasiri, W. R., et al. "Rapid urinary tract infection diagnostics by surface-enhanced Raman spectroscopy (SERS): identification and antibiotic susceptibilities." Anal Bioanal Chem 409(11): 3043-3054. (2017).
Qian et al., "Scaling Up Digital Circuit Computation with DNA Strand Displacement Cascades," Science2011; 6034: 1196-1201.
Quillin S.J. et al., "Neisseria gonorrhoeae host adaptation and pathogenesis"Nature Reviews Microbiology,2018. vol. 16, 226-240.
Rahimi F, et al. "Direct urine polymerase chain reaction for chlamydia and gonorrhoea: a simple means of bringing high-throughput rapid testing to remote settings?" Sex Health 10, 299-304 (2013).
Raja B. et al., "Development of a Panel of Recombinase Polymerase Amplification Assays for Detection of Common Bacterial Urinary Tract Infection Pathogens." J Appl Microbiol,(2017).
Reid M.S. "Exponential Isothermal Amplification of Nucleic Acids and Assays for Proteins, Cells, Small Molecules, and Enzyme Activities: An EXPAR Example." Angew Chern Int Ed Engl 57, 11856-11866 (2018).
Renner LD, et al. "Detection of ESKAPE Bacterial Pathogens at the Point of Care Using Isothermal DNA-Based Assays in a Portable Degas-Actuated Microfluidic Diagnostic Assay Platform." Appl Environ Microbiol 83,(2017).
Restriction Requirement for U.S. Appl. No. 16/158,233, filed Oct. 11, 2018 on behalf of California Institute of Technology, dated Oct. 22, 2020. 9 Pages.
Rizzo K. et al., "Carbapenem and Cephalosporin Resistance among Enterobacteriaceae in Healhcare-Associated Infections" *Emerging Infectious Diseases*,vol. 25, No. 7,Jul. 2019, pp. 1389-1393.
Robinson A.M. et al., "The rapid detection of cefotaxime-resistant Enterobacteriaceae by HPLC." Future Sci OA 2, FSQ142 (2016).
Rojas E.R. et al. "The outer membrane is an essential load-bearing element in Gram-negative bacteria." Nature 559, 617-621(2018).
Rolando J.C. "Real-Time, Digital LAMP with Commercial Microfluidic Chips Reveals the Interplay of Efficiency, Speed, and Background Amplification as a Function of Reaction Temperature and Time." Anal Chern, (2018).

(56) References Cited

OTHER PUBLICATIONS

Rowley, J., et al. "Chlamydia, gonorrhoea, trichomoniasis and syphilis: global prevalence and incidence estimates, 2016." Bulletin of the World Health Organization (2019).
Rui P. et al., "National Ambulatory Care Survey: 2015 State and National Summary Tables." (2015).
Sadiq S.T. et al., "Rapid accurate point-of-care tests combining diagnostics and antimicrobial resistance prediction for Neisseria gonorrhoeae and Mycoplasma genitalium." Sex Transm Infect 93, S65-S68(2017).
Santiso R. et al., "A rapid in situ procedure for determination of bacterial susceptibility or resistance to antibiotics that inhibit peptidoglycan biosynthesis." BMC Microbiol 11, 191(2011).
Satlin MJ, et al. "Multicenter Clinical and Molecular Epidemiological Analysis of Bacteremia Due to Carbapenem-Resistant Enterobacteriaceae (CRE) in the CRE Epicenter of the United States." Antimicrob Agents Chemother 61, e02349-02316 (2017).
Schoepp N.G. "Differential Accessibility to Polymerase During Isothermal Nucleic Acid Amplification Enables 30-Minute Phenotypic Beta-lactam Antibiotic Susceptibility Testing of Carbapenem-resistant Enterobacteriaceae (CRE)." In Preparation,(2018).
Schoepp, N.G., et al., "Rapid pathogen-specific phenotypic antibiotic susceptibility testing using digital LAMP quantification in clinical samples." Sci Transl Med, 9(410) eaal3693.Oct. 2017. 13 pages.
Schoepp NG et al., Differential DNA accessibility to polymerase enables 30-minute phenotypic β-lactam antibiotic susceptibility testing of carbapenem-resistant Enterobacteriaceae. PLoS Biol 18(3): e3000652, 22 pages (2020).
Schook P.O. et al., "The DNA-binding activity of the Neisseria gonorrhoeae LexA orthologue NG1427 is modulated by oxidation."*Molecular Microbiology*,2011. 79(4): p. 846-860.
Selck D.A et al., "Instrument for Real-Time Digital Nucleic Acid Amplification on Custom Microfluidic Devices." PLoS One 11, eQ163060 (2016).
Shawar, R. "510(k) Premarket Notification for K160901 Cepheid Xpert Carba-R Assay." Silver Spring, MD, USA Food and Drug Administration, Department of Health and Human Services. (2016).
Shen F, et al. "Multiplexed quantification of nucleic acids with large dynamic range using multivolume digital RT-PCR on a rotational SlipChip tested with HIV and hepatitis C viral load." J Am Chern Soc 133, 17705-17712(2011).
Siedner MJ, et al. "Real-time PCR assay for detection of quinolone-resistant Neisseria gonorrhoeae in urine samples." J Clin Microbiol 45, 1250-1254 (2007).
Silhavy T.J. et al., "The bacterial cell envelope." Cold Spring Harbor perspectives in biology 2, a000414 (2010).
Singh V. et al., "Comparative assessment of CDS, CLSI disc diffusion and E-test techniques for antimicrobial susceptibility testing of Neisseria gonorrhoeae: a 6-year study."*BMJ Open2*, e000969 (2012).
Smith T.F. et al., "Identification of common molecular subsequences."*J Mol Biol*,1981. 147(1): p. 195-197.
Song, J. et al., "Chemical Modifications to RNA: A New Layer of Gene Expression Regulation." ACS Chem Biol 12(2): p. 316-325. 2017.
Spilker, et al., "PCR-Based Assay for Differentiation of Pseudomonas aeruginosa from Other *Pseudomonas* Species Recovered from Cystic Fibrosis Patients" Journal of Clinical Microbiology, 2074-2079, 2004.
Stohl E.A et al., "Purification and characterization of the RecA protein from Neisseria gonorrhoeae"PloS One,2011. 6(2): p. e17101. 13 pages.
Stone M.R.L. "Fluorescent Antibiotics: New Research Tools to Fight Antibiotic Resistance." Trends Biotechnol,(2018).
Su Ih, et al. "A dielectrophoresis system for testing antimicrobial susceptibility of Gram-negative bacteria to betalactam antibiotics." Anal Chem, (2017).

Tamma PD, et al. "Comparing the Outcomes of Patients With Carbapenemase-Producing and Non-Carbapenemase-Producing Carbapenem-Resistant Enterobacteriaceae Bacteremia." Clin Infect Dis 64, 257-264 (2017).
Tapsall J. "Antimicrobial Resistance in Neisseria gonorhoeae"*World Health Organization*, WHO/CDS/CSR/DRS/2001.32001, 65 pages.
Tatusova T.A et al., "BLAST 2 Sequences, a new tool for comparing protein and nucleotide sequences."*FEMS Microbiol Lett*, 1999,174. 247-250.
*The European Committee on Antimicrobial Susceptibility Testing*"Ciprofloxacin/Neisseria gonorrhoeas International MIC Distribution-Reference Database"Apr. 2, 2018 https://mic.eucast.org/Eucast2/regShow.jsp?Id=35702.
Tobiason, D. M. et al., "The obligate human pathogen, Neisseria gonorrhoeae, is polyploid." PLoS Biology 4(6): 1069-1078. (2006).
Toley BJ, et al. "Isothermal strand displacement amplification (iSDA): a rapid and sensitive method of nucleic acid amplification for point-of-care diagnosis." Analyst 140, 7540-7549 (2015).
Tsongalis, Branched DNA Technology in Molecular Diagnostics, Am J Clin Pathol 2006; 126:448-453.
Tuite A.R. et al., "Impact of Rapid Susceptibility Testing and Antibiotic Selection Strategy on the Emergence and Spread of Antibiotic Resistance in Gonorrhea." J Infect Dis 216, 1141-1149 (2017).
Turner KM, et al. "Analysis of the potential for point-of-care test to enable individualised treatment of infections caused by antimicrobial-resistant and susceptible strains of Neisseria gonorrhoeae: a modelling study." BMJ Open 7, e015447 (2017).
Tyagi et al., "Multicolor molecular beacons for allele discrimination" Nature Biotechnology 16:49-53(1998).
UCLA Health System. "Antimicrobial Susceptibility Summary 2019;." Clinical Microbiology; Department of Pathology & Laboratory Medicine,(2019).
Unemo M. et al., "Antimicrobial resistance in Neisseria gonorrhoeae in the 21st century: past, evolution, and future." Clin Microbiol Rev 27, 587-613(2014).
Valiadi, M., et al. "Simple and rapid sample preparation system for the molecular detection of antibiotic resistant pathogens in human urine." Biomedical Microdevices 18(1). (2016).
van Belkum A, et al. "Developmental roadmap for antimicrobial susceptibility testing systems." Nature Reviews Microbiology,(2018).
Van Boeckel T.P et al., "Global antibiotic consumption 2000 to 2010: an analysis of national pharmaceutical sales data." The Lancet Infectious Diseases 14, 742-750 (2014).
van den Bogaart G. et al., "Protein mobility and diffusive barriers in *Escherichia coli*: consequences of osmotic stress." Mol Microbiol 64, 858-871(2007).
Vazquez-Laslop N. et al., "Molecular sieve mechanism of selective release of cytoplasmic proteins by osmotically shocked *Escherichia coli*." J Bacteriol 183, 2399-2404(2001).
Versporten A, et al. "Antimicrobial consumption and resistance in adult hospital inpatients in 53 countries: results of an internet-based global point prevalence survey." Lancet Glob Health 6, e619-e629 (2018).
Wade J.J. et al., "A fully defined, clear and protein-free liquid medium permitting dense growth of Neisseria gonorrhoeae from very low inocula." FEMS Microbiol Lett 273, 35-37 (2007).
Wadsworth C.B. et al., "Impact of population structure in the design of RNA-based diagnostics for antibiotic resistance in Neisseria gonorrhoeae." bioRxiv (2019).
Wagner, G.P et al., "Measurement of mRNA abundance using RNA-seq data: RPKM measure is inconsistent among samples." Theory Biosci, 131(4): p. 281-2855.2012.
Waldeisen J. R. et al., "A Real-Time PCR Antibiogram for Drug-Resistant Sepsis" PLoS ONE, Dec. 2011, vol. No. 12, pp. 1-6.
Wang et al., "Molecular Engineering of DNA: Molecular Beacons" Angew Chem Int Ed Engl, 48(5):856-870 2009.
Wegener, W. et al. "Cell envelope of Neisseria gonorrhoeae: relationship between autolysis in buffer and the hydrolysis of peptidoglycan." Infection and Immunity, vol. 18, No. 1, pp. 210-219 (Oct. 1977).

(56) References Cited

OTHER PUBLICATIONS

Wegener W.S .et al., "Cell envelope of Neisseria gonorrhoeae: penicillin enhancement of peptidoglycan hydrolysis." Infect Immun 18, 717-725(1977).
Weiner LM, et al. "Antimicrobial-Resistant Pathogens Associated With Healthcare-Associated Infections: Summary of Data Reported to the National Healthcare Safety Network at the Centers for Disease Control and Prevention, 2011-2014." Infection Control & Hospital Epidemiology 37, 1288-1301 (2016).
Weston E.J et al.,. "Strengthening Global Surveillance for Antimicrobial Drug-Resistant Neisseria gonorrhoeae through the Enhanced Gonococcal Antimicrobial Surveillance Program."*Emerg Infect Dis*23,(2Q17).
Whiley D.M. et al., "Genetic characterisation of Neisseria gonorrhoeae resistant to both ceftriaxone and azithromycin." Lancet Infectious Diseases 18, 717-718 (2018).
White House. "National Action Plan for Combating Antibiotic-Resistant Bacteria." (2015).
WHO—Antimicrobrial Resistance in Neisseria gonorrhoeae. In: World Health Organization, Department of Communicable Disease Surveillance and Response (2001).
WHO—Global Action Plan on Antimicrobial Resistance.(2015).
WHO—Global Action Plan to Control the Spread of and Impact of Antimicrobial Resistance in Neisseria gonorrhoeae. (2012).
WHO—Global Priority List of Antibiotic-resistant Bacteria to Guide Research, Discovery, and Development of New Antibiotics. (2017).
WHO—"No time to wait: Securing the future from drug-resistant infections Report to the Secretary-General of the United Nations." (2019).
WHO—WHO Guidelines for the treatment of Neisseria gonorrhoeae. (2016).
Wi T, et al. "Antimicrobial resistance in Neisseria gonorrhoeae: Global surveillance and a call for international collaborative action." PLoS Med 14, e1002344 (2017).
Wiesinger-Mayr et al. "Establishment of a semi-automated pathogen DNA isolation from whole blood and comparison with commercially available kits" J Microbial Methods, vol. 85,2011, pp. 206-213.
Wong L.K. et al., "Real-Time PCR Targeting the penA Mosaic XXXIV Type for Prediction of Extended-Spectrum-Cephalosporin Susceptibility in Clinical Neisseria gonorrhoeae Isolates. "*Antimicrob Agents Chemother*61 ,(2017).
Written Opinion for International Application No. PCT/US2018/055501 filed Oct. 11, 2018, on behalf of California Institute of Technology, dated Jan. 31, 2019. 8 pages.
Written Opinion for International Application No. PCT/US2019/044748 filed on Aug. 1, 2019 on behalf of California Institute of Technology dated Nov. 29, 2019 5 pages.
Ye, J., et al., "Primer-BLAST: a tool to design target-specific primers for polymerase chain reaction." BMC bioinformatics, 13(1): p. 134.2012. 11 pages.
Zankari E, et al. "Identification of acquired antimicrobial resistance genes." J Antimicrob Chemother 67, 2640-2644 (2012).
Zgurskaya H.I. et al., "Permeability Barrier of Gram-Negative Cell Envelopes and Approaches To Bypass It." ACS Infect Dis 1,512-522(2015).
Zhang Y, et al. "Epidemiology of Carbapenem-Resistant Enterobacteriaceae Infections: Report from the China CRE Network." Antimicrob Agents Chemother 62, e01882-01817 (2018).
Zhang Y, et al. "Label-Free Visualization of Carbapenemase Activity in Living Bacteria." Angew Chern Int Ed Engl 57, 17120-17124 (2018).
Zhao S. et al., "Genetics of chromosomally mediated intermediate resistance to ceftriaxone and cefixime in Neisseria gonorrhoeae." Antimicrob Agents Chemother 53, 3744-3751(2009).
Zheng G. et al., "Efficient and quantitative high-throughput tRNA sequencing."*Nat Methods*,2015, 12(9): p. 835-837. 5 pages.
Zou K.H. et al., "Receiver-operating characteristic analysis for evaluating diagnostic tests and predictive models." Circulation 115, 654-657 (2007).
Savela ES et al., Surfactant-enhanced DNA accessibility to nuclease accelerates phenotypic 62 -lactam antibiotic susceptibility testing of Neisseria gonorrhoeae. PLoS Biol 18(3): e3000651, 31 pages (2020).

\* cited by examiner

DIGITAL QUANTIFICATION OF DNA REPLICATION AND/OR CHROMOSOME SEGREGATION BASED DETERMINATION OF ANTIMICROBIAL SUSCEPTIBILITY

CROSS-REFERENCE TO RELATED APPLICATIONS

This application claims the benefit of U.S. Provisional Patent Application No. 62/399,196, filed Sep. 23, 2016, and U.S. Provisional Patent Application No. 62/460,625, filed Feb. 17, 2017, the disclosures of which are incorporated herein by reference.

STATEMENT AS TO FEDERALLY SPONSORED RESEARCH

This invention was made with government support under Grant No. EB012946 awarded by the National Institutes of Health and Grant No. HR0011-11-2-0006 awarded by the Defense Advanced Research Projects Agency. The government has certain rights in the invention.

SEQUENCE LISTING

The instant application contains a Sequence Listing which has been submitted in ASCII format via EFS-Web and is hereby incorporated by reference in its entirety. Said ASCII copy, created on Dec. 26, 2017, is named 38504US_CRF_sequencelisting.txt and is 2,221 bytes in size.

FIELD OF THE INVENTION

The present invention relates to methods of using digital isothermal amplification to detect subtle responses to environmental stimuli, such as detecting antibiotic susceptibility using digital quantification of DNA replication and/or chromosome segregation.

BACKGROUND OF THE INVENTION

Rapid antimicrobial susceptibility testing (AST) is urgently needed for informing treatment decisions and preventing the spread of antimicrobial resistance resulting from the misuse and overuse of antibiotics. To date, no phenotypic AST exists that can be performed within a single patient visit (30 min) directly from clinical samples. In existing AST tests using amplification reactions, the signal from the reaction is not read until the reaction is complete, which alone can be more than the duration of a standard patient visit.

What is needed therefore, are improved methods to increase the speed of determination of antibiotic susceptibility from sample to answer within the timeframe of a single patient visit.

SUMMARY OF THE INVENTION

In some embodiments, provided herein is a method of comparing two samples, comprising: distributing a first sample comprising a first amplifiable target molecule into a plurality of analysis regions to create a first population of digital samples; distributing a second sample comprising a second amplifiable target molecule into a plurality of analysis regions to create a second population of digital samples; initiating and performing an amplification reaction on the first population of digital samples and the second population of digital samples; detecting the presence or absence of amplification reaction in the first population and second population at a series of timepoints ($t_n$), said detection comprising identifying a number of analysis regions comprising a detectable signal in the first population ($^1P_n$) and identifying a number of analysis regions comprising a detectable signal in the second population ($^2P_n$) at each timepoint; and determining the ratio of $^1P_n$ to $^2P_n$ at a timepoint wherein ($^1P_n$-$^1P_{n-1}$)<($^1P_{n-1}$-$^1P_{n-2}$) or ($^2P_n$-$^2P_{n-1}$)<($^2P_{n-1}$-$^2P_{n-2}$), wherein the ratio of $^1P_n$ to $^2P_n$ is reflective of the relative concentration of first target molecule in the first sample to that of the second target molecule in the second sample, thereby comparing the two samples.

In some embodiments, the amplification reactions on the first population of digital samples and the second population of digital samples are performed simultaneously. In some embodiments, the amplification reactions on the first population of digital samples and the second population of digital samples are performed sequentially and under substantially identical conditions.

In some embodiments, less than 80%, less than 60%, less than 40%, or less than 20% of the plurality of analysis regions in said first population comprise said first amplifiable target molecule. In some embodiments, less than 80%, less than 60%, less than 40%, or less than 20% of the plurality of analysis regions in said second population comprise said second amplifiable target molecule.

In some embodiments, the first amplifiable target molecule is from a first population of microorganisms not exposed to an antibiotic, and wherein said second amplifiable target molecule is from a second population of said microorganisms exposed to said antibiotic. In some embodiments, the ratio is indicative of whether said microorganisms are resistant or susceptible to said antibiotic. In some embodiments, the ratio of $^1P_n$ to $^2P_n$ greater than a predetermined threshold is indicative of said microorganisms being susceptible to said antibiotic. In some embodiments, the microorganisms are E. coli, and said threshold is 1.10.

In some embodiments, the first and second populations of microorganisms are from a single source sample partitioned into said first and second populations. In some embodiments, the first and second populations of microorganisms are substantially similar except for said exposure to said antibiotic. In some embodiments, the first and second populations of microorganisms comprises a mixed population of microorganisms. In some embodiments, less than 90%, 80%, 70%, 60%, 50%, 40%, 30%, 20%, or 10% of the microorganisms in said first and second populations of microorganisms comprise said amplifiable target molecule.

In some embodiments, the microorganisms are bacteria. In some embodiments, the microorganisms are Enterobacteriaceae bacteria. In some embodiments, the exposure of said antibiotic to said second population of microorganisms was for a period of no more than 30 minutes, no more than 20 minutes, no more than 15 minutes, or no more than 10 minutes.

In some embodiments, the first amplifiable target molecule and said second amplifiable target molecule are the same. In some embodiments, the first amplifiable target molecule and said second amplifiable target molecule are different.

In some embodiments, the series of timepoints ($t_n$) are separated by 15 seconds, 30 seconds, 60 seconds, 90 seconds, 120 seconds, or 150 seconds.

In some embodiments, the step of determining the ratio is made when less than 95%, less than 90%, less than 80%, less than 70%, less than 60%, less than 50%, less than 40%, less than 30%, or less than 20% of said plurality of analysis regions in said first population of digital samples or said second population of digital samples emit said detectable signal.

In some embodiments, the amplification reaction is an isothermal reaction. In some embodiments, the isothermal reaction is selected from the group consisting of: strand displacement amplification (SDA), transcription mediated amplification, nucleic acid sequence based amplification (NASBA), recombinase polymerase amplification (RPA), rolling circle amplification, ramification amplification, helicase-dependent isothermal DNA amplification, and loop mediated isothermal amplification (LAMP).

In some embodiments, $(^1P_n\text{-}^1P_{n-1})<(^1P_{n-1}\text{-}^1P_{n-2})$ or $(^2P_n\text{-}^2P_{n-1})<(^2P_{n-1}\text{-}^2P_{n-2})$ occurs less than 10 minutes, less than 9 minutes, less than 8 minutes, less than 7 minutes, or less than 6 minutes after initiating said amplification reaction. In some embodiments, the step of detecting the presence or absence of amplification reaction at said timepoint at which said ratio of $^1P_n$ to $^2P_n$ is reflective of the relative concentration of first target molecule in the first sample to that of the second target molecule in the second sample is performed less than 10 minutes, less than 9 minutes, less than 8 minutes, less than 7 minutes, or less than 6 minutes after initiating said amplification reaction. In some embodiments, the ratio of $^1P_n$ to $^2P_n$ is determined at each of said series of timepoints.

In some embodiments, the amplifiable target molecule is a nucleic acid. In some embodiments, the nucleic acid comprises DNA or RNA. In some embodiments, the amplifiable target molecule is less than 50 kb, less than 100 kb, less than 200 kb, or less than 400 kb from an origin of replication. In some embodiments, the analysis regions are wells. In some embodiments, the distribution of the first and second sample into the plurality of analysis regions is performed in parallel.

In some embodiments, the plurality of analysis regions comprising the first sample or the second sample comprises at least 10, 20, 30, 40, or 50 analysis regions. In some embodiments, the plurality of analysis regions comprising the first sample or the second sample comprises at least 100, 200, 500, or 1,000 analysis regions.

Also provided herein, according to some embodiments of the invention, is a method of assessing an antibiotic susceptibility in a population of microorganisms, comprising: distributing a first sample comprising an amplifiable target molecule from a first portion of a population of microorganisms among a plurality of analysis regions to create a first population of digital samples, wherein the first portion has not been exposed to an antibiotic; distributing a second sample comprising said amplifiable target molecule from a second portion of the population of microorganisms among a plurality of analysis regions to create a second population of digital samples, wherein the second portion has been exposed to said antibiotic; initiating and performing an amplification reaction on the first population of digital samples and the second population of digital samples, wherein said amplification reaction is capable of generating a detectable signal due to amplification of said amplifiable target molecule; detecting the presence or absence of said detectable signal in the first and second populations at a series of timepoints ($t_n$), said detection comprising identifying a number of analysis regions in the first population comprising said detectable signal ($^1P_n$) and identifying a number of detectable analysis regions in the second population comprising said detectable signal ($^2P_n$) at each timepoint; and determining the ratio of $^1P_n$ to $^2P_n$ at a timepoint wherein said detectable signals are still being generated in some of said plurality of analysis regions by said amplification reaction, wherein the ratio of $^1P_n$ to $^2P_n$ is reflective of the susceptibility of the population of microorganisms to said antibiotic.

In some embodiments, the method of assessing an antibiotic susceptibility in a population of microorganisms further comprises comparing the ratio of $^1P_n$ to $^2P_n$ to a threshold. In some embodiments, a ratio of $^1P_n$ to $^2P_n$ above said threshold is indicative of susceptibility of said population of microorganisms to said antibiotic. In some embodiments, a ratio of $^1P_n$ to $^2P_n$ below said threshold is indicative of resistance of said population of microorganisms to said antibiotic.

In some embodiments, the threshold is 1.10. In some embodiments, the microorganisms are bacteria. In some embodiments, the microorganisms are Enterobacteriaceae bacteria.

In some embodiments, the amplification reactions on the first population of digital samples and the second population of digital samples are performed simultaneously. In some embodiments, the amplification reactions on the first population of digital samples and the second population of digital samples are performed sequentially and under substantially identical conditions.

In some embodiments, less than 80%, less than 60%, less than 40%, or less than 20% of the plurality of analysis regions in said first population comprise said amplifiable target molecule. In some embodiments, less than 80%, less than 60%, less than 40%, or less than 20% of the plurality of analysis regions in said second population comprise said amplifiable target molecule.

In some embodiments, the ratio is determined at a timepoint wherein $(^1P_n\text{-}^1P_{n-1})<(^1P_{n-1}\text{-}^1P_{n-2})$ or $(^2P_n\text{-}^2P_{n-1})<(^2P_{n-1}\text{-}^2P_{n-2})$. In some embodiments, $(^1P_n\text{-}^1P_{n-1})<(^1P_{n-1}\text{-}^1P_{n-2})$ or $(^2P_n\text{-}^2P_{n-1})<(^2P_{n-1}\text{-}^2P_{n-2})$ at a timepoint less than 10 minutes, less than 9 minutes, less than 8 minutes, less than 7 minutes, or less than 6 minutes after initiating said amplification reaction. In some embodiments, the step of detecting the presence or absence of amplification reaction at said timepoint at which said ratio of $^1P_n$ to $^2P_n$ is reflective of the susceptibility of the population of microorganisms to said antibiotic is performed less than 10 minutes, less than 9 minutes, less than 8 minutes, less than 7 minutes, or less than 6 minutes after initiating said amplification reaction.

In some embodiments, the ratio of $^1P_n$ to $^2P_n$ is determined at each of said series of timepoints. In some embodiments, the series of timepoints ($t_n$) are separated by 15 seconds, 30 seconds, 60 seconds, 90 seconds, 120 seconds, or 150 seconds.

In some embodiments, the step of determining the ratio is made when less than 95%, less than 90%, less than 80%, less than 70%, less than 60%, less than 50%, less than 40%, less than 30%, or less than 20% of said plurality of analysis regions in said first population of digital samples or said second population of digital samples emit said detectable signal.

In some embodiments, the reaction is an isothermal amplification reaction. In some embodiments, the isothermal amplification is selected from the group consisting of: strand displacement amplification (SDA), transcription mediated amplification, nucleic acid sequence based amplification (NASBA), recombinase polymerase amplification (RPA), rolling circle amplification, ramification amplification, helicase-dependent isothermal DNA amplification, and loop mediated isothermal amplification (LAMP).

In some embodiments, the amplifiable target molecule is a nucleic acid. In some embodiments, the nucleic acid comprises DNA. In some embodiments, the analysis regions are wells. In some embodiments, the amplifiable target molecule is less than 50 kb, less than 100 kb, less than 200 kb, or less than 400 kb from an origin of replication.

In some embodiments, the exposure of said second portion of the population of microorganisms to said antibiotic was for a period of no more than 30 minutes, no more than 20 minutes, no more than 15 minutes, or no more than 10 minutes.

In some embodiments, the plurality of analysis regions comprising the first sample or the second sample comprises at least 10, 20, 30, 40, or 50 analysis regions. In some embodiments, the plurality of analysis regions comprising the first sample or the second sample comprises at least 100, 200, 500, or 1,000 analysis regions. In some embodiments, the distribution of the first and second sample into the plurality of analysis regions is performed in parallel.

In some embodiments, the population of microorganisms comprises a mixed population of microorganisms. In some embodiments, less than 90%, 80%, 70%, 60%, 50%, 40%, 30%, 20%, or 10% of the microorganisms in said population of microorganisms comprise said amplifiable target molecule.

Also provided herein, according to some embodiments, is a method of assessing antibiotic susceptibility, comprising: providing an initial sample from a patient comprising a population of microorganisms; separating said initial sample into a first sample and a second sample, wherein said first sample is not exposed to an antibiotic, and wherein said second sample is exposed to said antibiotic; isolating an amplifiable target molecule from the population of microorganisms from said first and second samples to generate first and second populations of said amplifiable target molecule; distributing the first population of said amplifiable target molecule among a first plurality of analysis regions to create a first population of digital samples; distributing the second population of said amplifiable target molecule among a second plurality of analysis regions to create a second population of digital samples; initiating and performing an amplification reaction on the first population of digital samples and the second population of digital samples, wherein said amplification reaction is capable of generating a detectable signal due to amplification of said amplifiable target molecule; detecting the presence or absence of said detectable signal in the first and second populations at a series of timepoints ($t_n$), said detection comprising identifying a number of analysis regions in the first population comprising said detectable signal ($^1P_n$) and identifying a number of detectable analysis regions in the second population comprising said detectable signal ($^2P_n$) at each timepoint; and determining the ratio of $^1P_n$ to $^2P_n$ at a timepoint wherein said detectable signals are still being generated in some of said plurality of analysis regions by said amplification reaction, wherein the ratio of $^1P_n$ to $^2P_n$ is reflective of the susceptibility of the population of microorganisms to said antibiotic.

In some embodiments, the method further comprises comparing the ratio of $^1P_n$ to $^2P_n$ to a threshold to determine the susceptibility of the population of microorganisms to said antibiotic. In some embodiments, a ratio of $^1P_n$ to $^2P_n$ above said threshold is indicative of susceptibility of said population of microorganisms to said antibiotic. In some embodiments, a ratio of $^1P_n$ to $^2P_n$ below said threshold is indicative of resistance of said population of microorganisms to said antibiotic.

In some embodiments, said exposure to said antibiotic is performed in 30 minutes or less, 20 minutes or less, or 15 minutes or less. In some embodiments, said method is performed in 60 minutes or less, 50 minutes or less, 45 minutes or less, 40 minutes or less, 35 minutes or less, or 30 minutes or less.

Also provided herein, according to some embodiments, is a method of assessing antibiotic susceptibility in a population of microorganisms, comprising: providing a preliminary sample comprising a first target molecule from a population of microorganisms; distributing the preliminary sample into a first preliminary quantification analysis region; initiating and performing an amplification reaction in said first preliminary quantification analysis region to generate a preliminary quantification signal; determining from said preliminary quantification signal a preliminary quantification of said first target molecule in said population of microorganisms; distributing a first sample comprising an amplifiable target molecule from a first portion of said population of microorganisms among a plurality of analysis regions to create a first population of digital samples, wherein the first portion has not been exposed to an antibiotic; distributing a second sample comprising said amplifiable target molecule from a second portion of the population of microorganisms among a plurality of analysis regions to create a second population of digital samples, wherein the second portion has been exposed to said antibiotic; initiating and performing an amplification reaction on the first population of digital samples and the second population of digital samples, wherein said amplification reaction is capable of generating a detectable signal due to amplification of said amplifiable target molecule; detecting the presence or absence of said detectable signal in the first and second populations at a series of timepoints ($t_n$), said detection comprising identifying a number of analysis regions in the first population comprising said detectable signal ($^1P_n$) and identifying a number of detectable analysis regions in the second population comprising said detectable signal ($^2P_n$) at each timepoint; and determining the ratio of $^1P_n$ to $^2P_n$ at a timepoint wherein said detectable signals are still being generated in some of said plurality of analysis regions by said amplification reaction, wherein the ratio of $^1P_n$ to $^2P_n$ is reflective of the susceptibility of the population of microorganisms to said antibiotic.

In some embodiments, the method of assessing antibiotic susceptibility in a population of microorganisms further comprises: providing a control sample comprising a known quantity of said first target molecule; distributing said control sample into a second preliminary quantification analysis region; and initiating and performing an amplification reaction in said second preliminary quantification analysis region to generate a standard signal, wherein said preliminary quantification of said target molecule is determined by comparing the standard signal with the preliminary quantification signal.

In some embodiments, the preliminary quantification of said target molecule is determined by comparing the preliminary quantification signal with a standard curve.

In some embodiments, the method of assessing antibiotic susceptibility in a population of microorganisms further comprises comparing the ratio of $^1P_n$ to $^2P_n$ to a threshold.

Also provided herein is a method of determining a concentration of a target molecule in a sample, comprising: distributing a first sample comprising a first amplifiable target molecule into a plurality of analysis regions to create a first population of digital samples; distributing a second sample comprising a second amplifiable target molecule into a plurality of analysis regions to create a second population of digital samples, wherein the concentration of said second target molecule is known; initiating and performing an amplification reaction on the first population of digital samples and the second population of digital samples, wherein said amplification reaction is capable of generating a detectable signal due to amplification of said amplifiable target molecule; detecting the presence or absence of said detectable signal in the first and second populations at a series of timepoints ($t_n$), said detection comprising identifying a number of analysis regions in the first population comprising said detectable signal ($^1P_n$) and identifying a number of detectable analysis regions in the second population comprising said detectable signal ($^2P_n$) at each timepoint; and determining the ratio of $^1P_n$ to $^2P_n$ at a timepoint wherein said detectable signals are still being generated in some of said plurality of analysis regions by said amplification reaction, wherein the ratio of $^1P_n$ to $^2P_n$ is reflective of the concentration of the said first amplifiable target molecule in said first sample.

In some embodiments, the first sample is from a population of microorganisms, and wherein said ratio of $^1P_n$ to $^2P_n$ is reflective of a quantity of microorganisms in said population of microorganisms.

In some embodiments, the ratio is determined at a timepoint wherein ($^1P_n$-$^1P_{n-1}$)<($^1P_{n-1}$-$^1P_{n-2}$) or ($^2P_n$-$^2P_{n-1}$)<($^2P_{n-1}$-$^2P_{n-2}$). In some embodiments, ($^1P_n$-$^1P_{n-1}$)<($^1P_{n-1}$-$^1P_{n-2}$) or ($^2P_n$-$^2P_{n-1}$)<($^2P_{n-1}$-$^2P_{n-2}$) at a timepoint less than 10 minutes, less than 9 minutes, less than 8 minutes, less than 7 minutes, or less than 6 minutes after initiating said amplification reaction.

In some embodiments, the step of detecting the presence or absence of amplification reaction at said timepoint at which said ratio of $^1P_n$ to $^2P_n$ is reflective of the concentration of the said first amplifiable target molecule in said first sample is performed less than 10 minutes, less than 9 minutes, less than 8 minutes, less than 7 minutes, or less than 6 minutes after initiating said amplification reaction.

In some embodiments, the method of determining a concentration of a target molecule in a sample further comprises comparing the ratio of $^1P_n$ to $^2P_n$ to a threshold to determine the concentration of the said first amplifiable target molecule in said first sample.

In some embodiments, the amplification reactions on the first population of digital samples and the second population of digital samples are performed simultaneously.

In some embodiments, the amplification reactions on the first population of digital samples and the second population of digital samples are performed sequentially and under substantially identical conditions.

In some embodiments, less than 80%, less than 60%, less than 40%, or less than 20% of the plurality of analysis regions in said first population comprise said amplifiable target molecule. In some embodiments, less than 80%, less than 60%, less than 40%, or less than 20% of the plurality of analysis regions in said second population comprise said amplifiable target molecule.

Also provided herein is a method of assessing antibiotic susceptibility in mixed sample, comprising: providing an initial sample from a patient comprising a mixed population of microorganisms; separating said initial sample into a first sample and a second sample, wherein said first sample is not exposed to an antibiotic, and wherein said second sample is exposed to said antibiotic; isolating an amplifiable target molecule from the mixed population of microorganisms from said first and second samples to generate first and second populations of said amplifiable target molecule; distributing the first population of said amplifiable target molecule among a first plurality of analysis regions to create a first population of digital samples; distributing the second population of said amplifiable target molecule among a second plurality of analysis regions to create a second population of digital samples; initiating and performing an amplification reaction on the first population of digital samples and the second population of digital samples, wherein said amplification reaction is capable of generating a detectable signal due to amplification of said amplifiable target molecule; detecting the presence or absence of said detectable signal in the first and second populations at a series of timepoints ($t_n$), said detection comprising identifying a number of analysis regions in the first population comprising said detectable signal ($^1P_n$) and identifying a number of detectable analysis regions in the second population comprising said detectable signal ($^2P_n$) at each timepoint; and determining the ratio of $^1P_n$ to $^2P_n$ at a timepoint wherein said detectable signals are still being generated in some of said plurality of analysis regions by said amplification reaction, wherein the ratio of $^1P_n$ to $^2P_n$ is reflective of the susceptibility of the population of microorganisms to said antibiotic.

In some embodiments, less than 90%, 80%, 70%, 60%, 50%, 40%, 30%, 20%, or 10% of the microorganisms in said mixed populations of microorganisms comprise said amplifiable target molecule. In some embodiments, the method of assessing antibiotic susceptibility in mixed sample further comprises comparing the ratio of $^1P_n$ to $^2P_n$ to a threshold.

INCORPORATION BY REFERENCE

All publications, patents, and patent applications mentioned in this specification are herein incorporated by reference to the same extent as if each individual publication, patent, or patent application was specifically and individually indicated to be incorporated by reference.

Described herein are a number of devices and methods that can be used individually or in various combinations for applications including but not limited to those listed herein. Furthermore, they can be used in various combinations with previously disclosed devices and methods for previously described applications.

The present application incorporates the following applications by reference in their entireties for any and all purposes: U.S. Application 61/516,628, "Digital Isothermal Quantification of Nucleic Acids Via Simultaneous Chemical Initiation of Recombinase Polymerase Amplification (RPA) Reactions on Slip Chip," filed on Apr. 5, 2011; U.S. Application 61/518,601, "Quantification of Nucleic Acids With Large Dynamic Range Using Multivolume Digital Reverse Transcription PCR (RT-PCR) On A Rotational Slip Chip Tested With Viral Load," filed on May 9, 2011; U.S. application Ser. No. 13/257,811, "Slip Chip Device and Methods," filed on Sep. 20, 2011; International Application No. PCT/US2010/028361, "Slip Chip Device and Methods," filed on Mar. 23, 2010; U.S. Application 61/262,375, "Slip Chip Device and Methods," filed on Nov. 18, 2009; U.S. Application 61/162,922, "Slip Chip Device and Methods," filed on Mar. 24, 2009; U.S. Application 61/340,872, "Slip Chip Device and Methods," filed on Mar. 22, 2010; U.S. application Ser. No. 13/440,371, "Analysis Devices, Kits, And Related Methods For Digital Quantification Of Nucleic Acids And Other Analytes," filed on Apr. 5, 2012; U.S. application Ser. No. 13/467,482, "Multivolume Devices, Kits, Related Methods for Quantification and Detection of Nucleic Acids and Other Analytes," filed on May 9, 2012; U.S. application Ser. No. 13/868,028, "Fluidic Devices and Systems for Sample Preparation or Autonomous Analysis," filed on Apr. 22, 2013; U.S. application Ser. No. 13/868,009, "Fluidic Devices for Biospecimen Preservation," filed on Apr. 22, 2013; International Application PCT/US2013/037658, "Fluidic Devices for Biospecimen Preservation," filed on Apr. 22, 2013; International Application PCT/US2013/037660, "Fluidic Devices and Systems for Sample Preparation or Autonomous Analysis," filed on Apr. 22, 2013; U.S. application Ser. No. 13/869,856, "Slip-Induced Compartmentalization," filed Apr. 24, 2013; International Application PCT/US2013/063594, "Methods and Systems for Microfluidics Imaging and Analysis," filed on Oct. 4, 2013; international application PCT/US2014/034728, "Parallelized Sample Handling," filed on Apr. 18, 2014; International Application PCT/US2014/047092, "Digital Assay for Quantifying and Concentrating Analytes," filed on Jul. 17, 2014; U.S. Application 62/038,036, "The Pumping Lid: Devices and Methods for Programmable Generation of Positive and Negative Pressures," filed on Aug. 15, 2014; U.S. Application 62/050,647, "Digital Microfluidics Methods for Optimizing Isothermal Amplification Reactions," filed on Sep. 15, 2014; international application PCT/US2014/056401, "System and Method for Movement and Timing Control," filed on Sep. 18, 2014; International Application No. PCT/US2014/060977 "Enhanced Nucleic Acid Identification and Detection" filed on Oct. 16, 2014; U.S. Application 62/075,648, "Microfluidic Measurements of the Responses of an Organism to a Drug," filed on Nov. 5, 2014; and International Application No. PCT/US2015/059344 "Microfluidic Measurements of the Responses of an Organism to a Drug," filed on Nov. 5, 2015.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead placed upon illustrating the principles of various embodiments of the invention.

DETAILED DESCRIPTION

Figure 1:
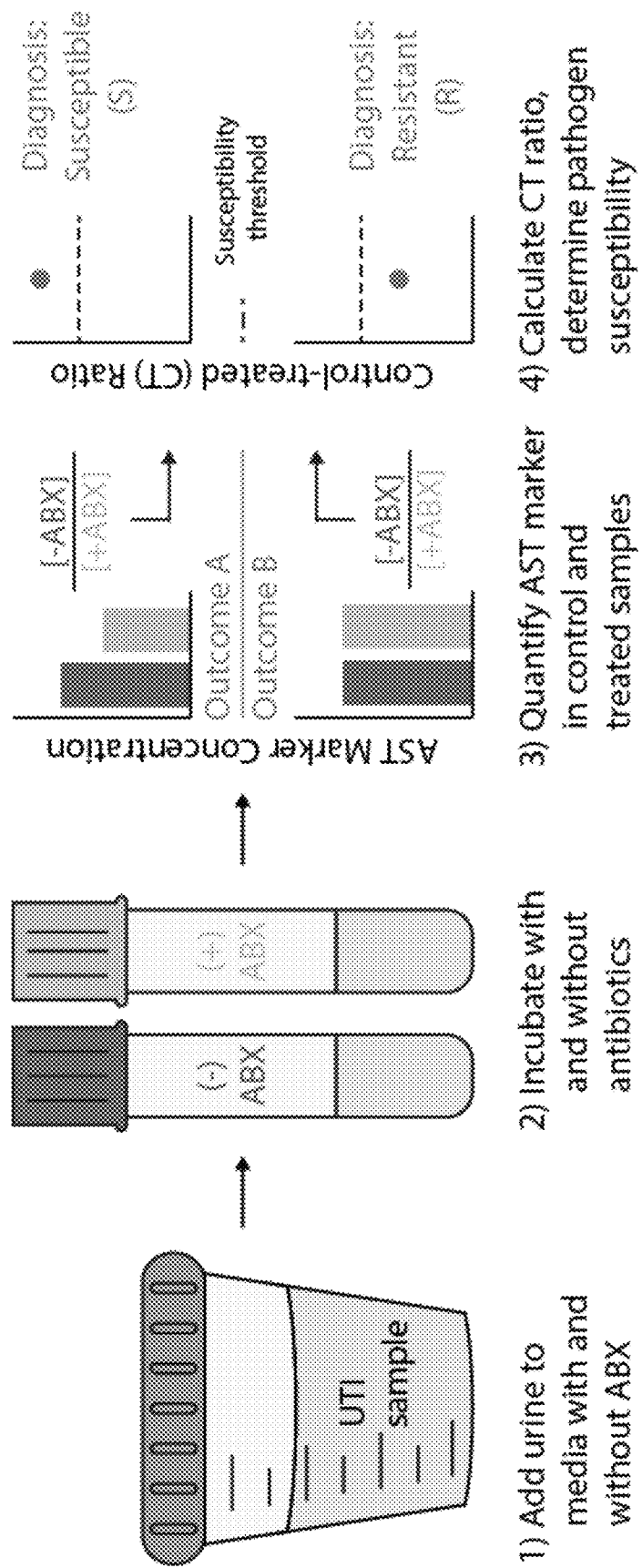
FIG. 1 shows an example of an experimental workflow of a dAST method, according to an embodiment of the invention.

The details of various embodiments of the invention are set forth in the description below. Other features, objects, and advantages of the invention will be apparent from the description and the drawings, and from the claims.

Unless defined otherwise, all technical and scientific terms used herein have the same meaning as is commonly understood by one of skill in the art to which the claimed subject matter belongs. All patents, patent applications, published applications and publications, GENBANK sequences, websites and other published materials referred to throughout the entire disclosure herein, unless noted otherwise, are incorporated by reference in their entirety. In the event that there is a plurality of definitions for terms herein, those in this section prevail. Where reference is made to a URL or other such identifier or address, it is understood that such identifiers can change and particular information on the internet can come and go, but equivalent information is known and can be readily accessed, such as by searching the internet and/or appropriate databases. Reference thereto evidences the availability and public dissemination of such information.

As used herein, the singular forms "a," "an" and "the" include plural referents unless the context clearly dictates otherwise. In this application, the use of the singular includes the plural unless specifically stated otherwise. As used herein, the use of "or" means "and/or" unless stated otherwise. Furthermore, use of the term "including" as well as other forms (e.g., "include", "includes", and "included") is not limiting.

As used herein, ranges and amounts can be expressed as "about" a particular value or range. About also includes the exact amount. Hence "about 10 degrees" means "about 10 degrees" and also "10 degrees." Generally, the term "about" can include an amount that would be expected to be within experimental error.

Assays

Described herein is a method to use fast signal amplification of digital samples with high resolution and the ability to calculate the relative abundance of an amplifiable target molecule in a sample. The method includes the detection of time-to-positive (TTP), i.e., the number of digital samples in a population of digital samples with a detectable signal due to, e.g., isothermal amplification of the amplifiable target molecule. The relative TTP between two populations of digital samples (or ratio) can be used to determine a relative abundance of the amplifiable target molecule. This method is broadly applicable to determining relative concentrations of markers. In some embodiments, this method also can be used to identify characteristics of a sample based on the relative concentration of markers, including but not limited to, a concentration of amplifiable target analytes, a quantity and/or identity of microorganisms present in a sample, a susceptibility/resistance of a microorganism to a drug, and a minimum inhibitory concentration of an antimicrobial agent (e.g., an antibiotic) for a microorganism in a sample.

In some embodiments, the method provides a complete phenotypic sample-to-answer antibiotic susceptibility test (AST) that can be performed in less than 30 minutes from clinical samples. In this embodiment, the amplifiable target molecule is a marker that increases or decreases as a function of antibiotic susceptibility in a population of microorganisms exposed to the antibiotic (i.e., an AST marker) in each sample. The method provided herein can be used to determine the concentration of one or more AST markers in samples untreated with one or more antibiotics and samples treated with one or more antibiotics using TTP values from digital samples and digital isothermal amplification. In some embodiments, the TTP values of the digital samples are monitored in real-time.

In some embodiments, fast signal amplification is performed using digital LAMP on SlipChips. Although LAMP was used in the examples, another fast nucleic acid amplification technique can be used and can include the use of different and/or additional devices or technologies other than SlipChips that provide the ability to calculate the concentration of an AST marker in each sample (e.g. the concentration of one or more AST markers in samples untreated with one or more antibiotics and samples treated with one or more antibiotics) during the amplification reaction in real-time.

In some embodiments, digital isothermal amplification is used and time-to-positive (TTP) of digital samples are monitored in real-time. In some embodiments, concentrations of amplifiable target molecules are calculated and the relative difference in the amplifiable target molecule concentration between samples are calculated in real-time without waiting for an endpoint readout. The comparison can be between treated and untreated populations of microorganisms, or can be between an unknown amplifiable target molecule concentration and a known amplifiable target molecule amplification. By monitoring the TTP of the digital samples in real time, a relative quantification for e.g., AST determination or quantification can be made prior to completing amplification of all positive wells. In some embodiments, the method includes detecting the presence or absence of amplification reaction in the first population and second population at a series of timepoints ($t_n$), the detection comprising identifying a number of analysis regions comprising a detectable signal in the first population ($^1P_n$) and identifying a number of analysis regions comprising a detectable signal in the second population ($^2P_n$) at each timepoint, and determining the ratio of $^1P_n$ to $^2P_n$. In some embodiments, the ratio is determined at a timepoint wherein ($^1P_n$-$^1P_{n-1}$)<($^1P_{n-1}$-$^1P_{n-2}$) or ($^2P_n$-$^2P_{n-1}$)<($^2P_{n-1}$-$^2P_{n-2}$), wherein the ratio of $^1P_n$ to $^2P_n$ is reflective of the relative concentration of first target molecule in the first sample to that of the second target molecule in the second sample, thereby comparing the two samples.

In some embodiments, the ratio is indicative of the minimum inhibitory concentration of an antibiotic for a population of microorganisms. In some embodiments, the ratio is indicative of the absolute concentration of an amplifiable target molecule in a sample. In some embodiments, the ratio is indicative of the absolute concentration of a species whose quantity is correlated with the amplifiable target molecule, such as the quantity of a microorganism present in a sample.

In some embodiments, quantification of RNA as an amplifiable target molecule can be performed, e.g., by adding reverse transcriptase to the isothermal amplification reaction. This enables reverse transcription and subsequent amplification of resulting DNA in addition to any DNA originally present. This method can be used to perform AST using RNA markers. This method can be used to rapidly quantify RNA. In some embodiments, RNA is used to determine susceptibility with or without DNA also being quantified. In some embodiments, susceptibility is quantified using a 16S rRNA target.

The devices and methods described herein can be applied for assays for detection of drug susceptibility or resistance in a microorganism. The detection can be detection of a signal generated by an assay, for example, an assay to detect a nucleic acid or quantification of a nucleic acid associated with a resistance or susceptibility to a drug in a microorganism.

An assay can comprise conducting a reaction (e.g., amplification) on a nucleic acid from a microorganism exposed to a drug and comparing the results of the reaction (e.g., reaction outcome, positive or negative signal generation) to a reaction conducted on a nucleic acid from a microorganism that has not been exposed to the drug. This can reveal a susceptibility or a resistance of the microorganism to the drug.

In certain embodiments, the method comprises exposing a portion of a sample containing a microorganism to a drug. In some embodiments, the method further comprises extracting nucleic acid from the microorganism. In some embodiments, the method comprises performing a sequence-specific quantification of a nucleic acid from the microorganism. The quantification information is then used for determining or quantifying a resistance or susceptibility of a microorganism to a drug.

Assays can be conducted in a digital format, that is, assays can be conducted on a sample divided into partitions (i.e., analysis regions) such that some of the partitions provide no signal, while other partitions provide a signal, thereby creating digital samples. In some embodiments, the partitions contain one or zero detectable amplifiable target molecules (e.g., nucleic acid molecules such as DNA or RNA). In some cases, some partitions can contain more than one amplifiable target molecule. In some embodiments, the reaction efficiency is such that a threshold number of amplifiable target molecules is required to achieve a positive signal. In these cases, the format is digital and the analysis regions comprise a population of digital samples if some of the partitions contain a number of amplifiable target molecules above the threshold, and some of the partitions contain a number of amplifiable target molecules below the threshold. In some embodiments, the threshold can vary between partitions, such that some partitions with fewer amplifiable target molecules generate a signal, while some partitions with more amplifiable target molecules do not generate signal. In these cases, digital detection using digital samples can still be performed based on a probabilistic threshold applied over a plurality of wells, as long as some partitions do not produce a signal, and some do. This digital format, including the use of one or more populations of digital samples can be used in conjunction with assays described herein, including identification, detection, genotyping, SNP detection, rare allele detection, and quantification of nucleic acids.

An assay can be conducted in less than or equal to about 180 minutes, 120 minutes, 110 minutes, 100 minutes, 90 minutes, 80 minutes, 70 minutes, 60 minutes, 50 minutes, 40 minutes, 30 minutes, 20 minutes, 15 minutes, 10 minutes, 9 minutes, 8 minutes, 7 minutes, 6 minutes, 5 minutes, 4 minutes, 3 minutes, 2 minutes, or 1 minute. An assay can have an accuracy of at least about 70%, 80%, 90%, 95%, 96%, 97%, 98%, 99%, 99.9%, or 99.99%. The rates of false positives can be below 10%, below 1%, below 0.1%, below 0.01%, below 0.001%, or below 0.0001%. The rates of false negatives can be below 10%, below 1%, below 0.1%, below 0.01%, below 0.001%, or below 0.0001%.

Assays can be used for detecting copy number variations (CNVs). CNVs are a form of structural variation, alterations of the DNA of a genome that changes the number of copies of one or more sections of the DNA. CNVs can correspond to relatively large regions of the genome that have been deleted or duplicated on certain chromosomes. Like other types of genetic variation, some CNVs have been associated with susceptibility or resistance to disease. Gene copy number can be elevated in cancer cells.

Antibiotic susceptibility testing method through measuring DNA replication (e.g., by detecting CNV) is applicable to evaluation of response to antibiotics, and other agents impairing cell growth and genomic DNA replication in all the unicellular and multicellular organisms, including eukaryotes. The measurement of "relative chromosomal DNA replication rate" is a useful measurable parameter to distinguish between susceptible cells growing in the presence versus absence of a drug (e.g., an antibiotic) and resistant cells growing in the presence versus absence of a drug. In some embodiments, differences in these markers can be observed using the devices and methods disclosed herein within a time period that is shorter than the average time of division of a cell, enabling the detection of cellular replication in that cell earlier than methods of detection that are dependent on cell-division. Therefore, methods and devices described herein enable one to rapidly distinguish between cells that are drug resistant and drug susceptible. The methods and devices provided herein can also be applied to any drug-screening, including screening of human cells (such as e.g. in the monitoring of a tumor biopsy in response to treatment).

In one embodiment, copy number of rDNA within cells is measured after cells are incubated for short periods of time, with and without the presence of antibiotics, and the difference in the magnitude of this change is used to determine drug resistance and susceptibility of the cells. In some embodiments, the change in rDNA copy is determined using a nucleic acid amplification technique (such as for example qPCR or digital PCR or digital isothermal amplification), and the results used to determine resistance or susceptibility to the drug. In some embodiments, the method for determining drug susceptibility uses digital quantification. In some embodiments, average DNA fragments copies originated from individual cells, are digitally quantified to measure proximal to origin/distant to origin selected gene rates.

In some embodiments, drug susceptibility testing is based on RNA, such as by comparing transcription levels. In some embodiments, drug susceptibility testing is based on RNA, such as by comparing transcription levels using digital quantification. In some embodiments, quantification strategies (such as e.g. NASBA, qRT-PCR, sequencing, nanostring, among others) can be appropriate. In some embodiments RNA from cells obtained from samples is quantified in a digital format. In some embodiments gene target expression levels in each individual cell are quantified through single cell measurements on a device, such as the devices described herein.

An assay can be used for quantitative detection of nucleic acids, such as recA mRNA. For example, a method can be used comprising the steps of taking a sample from the patient, accessing RNA in the sample or extracting RNA from the sample, using at least one RT-LAMP primer to reverse transcribe and amplify the mRNA in a qualitative and/or in a quantitative format, and testing for amplification to confirm presence of nucleic acids including but not limited to recA mRNA.

In some embodiments, relative RNA and/or DNA amplification is used. In some embodiments, relative RNA and/or DNA quantification is used. In some embodiments digital detection is used for RNA and/or DNA quantification. In some embodiments, multiple reliable RNA and/or DNA targets are used simultaneously in multiplex format. In some embodiments, RNA targets and/or their genes involved in the same physiological process or antibiotic response mechanism can be used.

In some embodiments, this invention could be applied to drug resistance testing of tumor cells. In some embodiments, this invention be applied to drug resistance testing of cancerous cells. The devices describe herein are applicable for use with a variety of sample types, including clinical sample types, (such as, for example, in-patient vs out-patient, pre-treated vs treatment-naïve), infection levels (such as, for example, negative vs positive vs contaminated), and sample storage/handling (such as, for example, fresh vs borate-preserved vs refrigerated).

In some embodiments, a slow growing microorganism's drug resistance is possible to assess through a combination of staining and genetic markers using the devices and methods described herein. In some embodiments, a combination of genetic markers of cell growth and genetic markers of antibiotic susceptibility can be used to determine the genetic antibiotic resistance of slow-growing cells.

The assays, reactions, and techniques described herein can be performed on any suitable platform, including but not limited to tubes, capillary tubes, droplets, microfluidic devices (e.g., SlipChip devices), wells, well plates, microplates, microfluidic wells, microfluidic droplets, emulsions, solid supports (e.g., beads or microarrays), microchips, or gels (e.g., 2D gels, 3D gels) and reactions inside gels including "polonies" as in polony PCR on surfaces and in gels.

Samples

Disclosed herein are methods, devices and systems related to analysis of samples. In some embodiments, methods of the invention comprises obtaining a sample from an organism. A sample can be obtained from a subject (e.g., a patient or a pet) and can include blood, feces, urine, saliva or other bodily fluid. The sample can be obtained by the patient or by a medical professional. Examples of medical professionals include, but are not limited to, physicians, emergency medical technicians, nurses, first responders, psychologists, medical physics personnel, nurse practitioners, surgeons, dentists, and any other medical professional. The sample can be obtained from any bodily fluid, for example, amniotic fluid, aqueous humor, bile, lymph, breast milk, interstitial fluid, blood, blood plasma, cerumen (earwax), Cowper's fluid (pre-ejaculatory fluid), chyle, chyme, female ejaculate, menses, mucus, saliva, urine, vomit, tears, vaginal lubrication, sweat, serum, semen, sebum, pus, pleural fluid, cerebrospinal fluid, synovial fluid, intracellular fluid, and vitreous humour. In an example, the sample is obtained by a blood draw, where the medical professional draws blood from a subject, such as by a syringe.

Samples can be collected in a sample collection container. In some embodiments the sample collection container is coded with information that can be detected. For example a detector can recognize a barcode. The barcode can have information about where a sample was collected or from which individual a sample was collected. A detector can take this information and use it to process or transmit data generated regarding a sample. For example a camera-phone can take a photo of a sample collection container. The camera-phone can recognize a barcode on the container which identifies a patient. The camera-phone can then link date generated regarding the sample to the patient from which the sample was obtained. The linked data can then be transmitted to the patient or to the patient's physician. In some embodiments a single image is generated of the sample collection container and a sample analysis unit.

Food samples can also be analyzed. Samples can be any composition potentially comprising a target a microorganism. Sources of samples include, but are not limited to, geothermal and hydrothermal fields, acidic soils, sulfotara and boiling mud pots, pools, hot-springs and geysers where the enzymes are neutral to alkaline, marine actinomycetes, metazoan, endo and ectosymbionts, tropical soil, temperate soil, arid soil, compost piles, manure piles, marine sediments, freshwater sediments, water concentrates, hypersaline and super-cooled sea ice, arctic tundra, Sargasso sea, open ocean pelagic, marine snow, microbial mats (such as whale falls, springs and hydrothermal vents), insect and nematode gut microbial communities, plant endophytes, epiphytic water samples, industrial sites and ex situ enrichments. Additionally, a sample can be isolated from eukaryotes, prokaryotes, myxobacteria (epothilone), air, water, sediment, soil or rock, a plant sample, a food sample, a gut sample, a salivary sample, a blood sample, a sweat sample, a urine sample, a spinal fluid sample, a tissue sample, a vaginal swab, a stool sample, an amniotic fluid sample, a fingerprint, aerosols, including aerosols produced by coughing, skin samples, tissues, including tissue from biopsies, and/or a buccal mouthwash sample. Other sample types include samples for clinical testing (such as, for example, in-patient vs out-patient, pre-treated vs treatment-naïve), infection level testing (such as, for example, negative vs positive vs contaminated), and storage/handling testing (such as, for example, fresh vs borate-preserved vs refrigerated).

Samples can comprise organisms. Samples can comprise microorganisms. The number of microorganisms in a sample can be less than 10, less than 100, less than 1,000, less than $10^4$, less than $10^5$, or less than $10^6$. In some embodiments, the sample is a processed sample (e.g., concentrated, filtered, etc.).

Samples can comprise amplifiable target molecules from the microorganisms. Amplifiable target molecules can comprise, for example, nucleic acids, such as DNA or RNA. Nucleic acids can be cell-free nucleic acids. Nucleic acids can be isolated from cells. Nucleic acids can be single or double stranded. The DNA can be ssDNA, dsDNA, cDNA, or any combination thereof. In some cases, the RNA comprises mRNA. In some cases, the RNA comprises noncoding RNA (ncRNA). The noncoding RNA can comprise transfer RNA (tRNA), ribosomal RNA (rRNA), transfer-messenger RNA (tmRNA), small nucleolar RNA (snoRNA), microRNA (miRNA), small interfering RNA (siRNA), small nuclear RNA (snRNA), piwi-interacting RNA (piRNA), long ncRNA (lncRNA), and/or other types of ncRNA. In some cases, the RNA is from bacteria or viruses. In some cases, the RNA is collected from a cell. In some examples, the RNA is intracellular. In some cases, the RNA is extracellular.

The terms "nucleic acid" and "nucleic acid molecule" as used interchangeably herein, refer to a molecule comprised of nucleotides, i.e., ribonucleotides, deoxyribonucleotides, or both. The term includes monomers and polymers of ribonucleotides and deoxyribonucleotides, with the ribonucleotide and/or deoxyribonucleotides being connected together, in the case of the polymers, via 5' to 3' linkages. Nucleic acids can be detected from a sample.

Amplifiable target molecules can comprise genetic markers of cell growth and genetic markers of antibiotic susceptibility. Amplifiable target molecules can include markers for drug resistance or susceptibility of tumor cells. Amplifiable target molecules can include markers for oxidative stress that can be detected with, e.g., oxidation-sensitive dyes to assay cell viability in response to treatment with a drug. In some embodiments, amplifiable target molecules comprise nucleic acids, such as DNA or RNA.

Many clinical and other samples contain multiple microbes (e.g. microorganisms that contaminate the sample during processing or commensals that are present in the sample). The contaminating/commensal species can be bacteria, or other living microorganisms that could be resistant or susceptible to an antibiotic and thus could confound AST results. In some embodiments, preferably, AST should specifically assess the response of the pathogen(s) of interest and not detect markers from contaminating or commensal microorganisms.

In some embodiments, the digital AST method shown here can also be used in the presence of commensal bacteria. This is because the present method uses sequence-specific primers that detect the pathogen(s) of interest without substantial interference from other cells or their genetic material. This demonstrates an advantage of this dAST methodology vs non-specific AST methods such as microscopy (observing cell shape or monitoring optical density), or metabolic dyes, which can yield a signal as a result of the presence of other microorganisms.

Microorganisms

The term "microorganism" refers to any microscopic organism, and typically consists of only a single cell. Microorganisms include bacteria, yeast, fungi, viruses, protists (protozoan, micro-algae), archaebacteria, and eukaryotes, such as a single-celled eukaryotic cell. Bacteria include gram-positive and gram-negative bacteria. The term "microorganism" refers to living matter and viruses comprising nucleic acid that can be detected and identified by the methods of the invention. Different microorganisms can be different strains, different varieties, different species, different genera, different families, different orders, different classes, different phyla, and/or different kingdoms.

Microorganisms can include bacterial pathogens such as: *Aeromonas hydrophila* and other species (spp.); *Bacillus anthracis*; *Bacillus cereus*; Botulinum neurotoxin producing species of *Clostridium*; *Brucella abortus*; *Brucella melitensis*; *Brucella suis*; *Burkholderia mallei* (formally *Pseudomonas mallei*); *Burkholderia pseudomallei* (formerly *Pseudomonas pseudomallei*); *Campylobacter jejuni*; *Chlamydia psittaci*; *Clostridium botulinum*; *Clostridium botulinum*; *Clostridium perfringens*; *Coccidioides immitis*; *Coccidioides posadasii*; *Cowdria ruminantium* (Heartwater); *Coxiella burnetii*; Enterovirulent *Escherichia coli*/group (EEC Group) such as *Escherichia coli*-enterotoxigenic (ETEC), *Escherichia coli*-enteropathogenic (EPEC), *Escherichia coli*-O157:H7 enterohemorrhagic (EHEC), and *Escherichia coli*-enteroinvasive (EIEC); *Ehrlichia* spp. such as *Ehrlichia chaffeensis*; *Francisella tularensis*; *Legionella pneumophilia*; *Liberobacter africanus*; *Liberobacter asiaticus*; *Listeria monocytogenes*; miscellaneous enterics such as *Klebsiella*, *Enterobacter*, *Proteus*, *Citrobacter*, *Aerobacter*, *Providencia*, and *Serratia*; *Mycobacterium bovis*; *Mycobacterium tuberculosis*; *Mycoplasma capricolum*; *Mycoplasma mycoides* ssp *mycoides*; *Peronosclerospora philippinensis*;

*Phakopsora pachyrhizi; Plesiomonas shigelloides; Ralstonia solanacearum* race 3, biovar 2; *Rickettsia prowazekii; Rickettsia rickettsii; Salmonella* spp.; *Schlerophthora rayssiae varzeae; Shigella* spp.; *Staphylococcus aureus; Streptococcus; Synchytrium endobioticum; Vibrio cholerae* non-O1; *Vibrio cholerae* O1; *Vibrio parahaemolyticus* and other *Vibrios; Vibrio vulnificus; Xanthomonas oryzae; Xylella fastidiosa* (citrus variegated chlorosis strain); *Yersinia enterocolitica* and *Yersinia pseudotuberculosis*; and *Yersinia pestis*.

A non-limiting list of pathogens with known drug-resistance properties that can be detected and analyzed with the methods and devices disclosed herein include *Clostridium difficile*, carbapenem-resistant Enterobacteriaceae (CRE), drug-resistant *Neisseria gonorrhoeae*, multidrug-resistant *Acinetobacter*, drug-resistant *Campylobacter*, fluconazole-resistant *Candida* (a fungus), extended spectrum β-lactamase producing Enterobacteriaceae (ESBLs), vancomycin-resistant *Enterococcus* (VRE), multidrug-resistant *Pseudomonas aeruginosa*, drug-resistant Non-typhoidal *Salmonella*, drug-resistant *Salmonella Typhi*, drug-resistant *Shigella*, methicillin-resistant *Staphylococcus aureus* (MRSA), drug-resistant *Streptococcus pneumoniae*, drug-resistant *M. tuberculosis*, vancomycin-resistant *Staphylococcus aureus* (VRSA), erythromycin-resistant Group A *Streptococcus*, and clindamycin-resistant Group B *Streptococcus*.

Antimicrobial/Antibiotic Compounds

Samples comprising a population of microorganisms are incubated with a drug to determine a response to indicate the microorganisms' resistance or susceptibility to the drug. In some embodiments, the drug includes compounds for the treatment of a tumor. In some embodiments, the drug is an antibiotic compound or an antimicrobial compound. As used herein, the term antimicrobial is meant to include any substance of natural, semisynthetic or synthetic origin that is used to kill or inhibit the growth of a microorganism. In preferred embodiments, antimicrobials do not harm a host of the microorganism. As used herein, the term "antimicrobial" and the term "antibiotic" are interchangeable. Examples of antimicrobial or antibiotic compounds include, but are not limited to: Amikacin, Gentamicin, Kanamycin, Neomycin, Netilmicin, Tobramycin, Paromomycin, Streptomycin, Spectinomycin(Bs), Geldanamycin, Herbimycin, Rifaximin, Loracarbef, Ertapenem, Doripenem, Imipenem/Cilastatin, Meropenem, Cefadroxil, Cefazolin, Cefalotin/Cefalothin, Cefalexin, Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone, Cefepime, Ceftaroline fosamil, Ceftobiprole, Teicoplanin, Vancomycin, Telavancin, Dalbavancin, Oritavancin, Clindamycin, Lincomycin, Daptomycin, Azithromycin, Clarithromycin, Dirithromycin, Erythromycin, Roxithromycin, Troleandomycin, Telithromycin, Spiramycin, Aztreonam, Furazolidone, Nitrofurantoin (nit), Linezolid, Posizolid, Radezolid, Torezolid, Amoxicillin, Ampicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Temocillin, Ticarcillin, Amoxicillin/clavulanate (amc), Ampicillin/sulbactam, Piperacillin/tazobactam, Ticarcillin/clavulanate, Bacitracin, Colistin, Polymyxin B, Ciprofloxacin (cip), Enoxacin, Gatifloxacin, Gemifloxacin, Levofloxacin, Lomefloxacin, Moxifloxacin, Nalidixic acid, Norfloxacin, Ofloxacin, Trovafloxacin, Grepafloxacin, Sparfloxacin, Temafloxacin, Mafenide, Sulfacetamide, Sulfadiazine, Silver sulfadiazine, Sulfadimethoxine, Sulfamethizole, Sulfamethoxazole, Sulfanilimide (archaic), Sulfasalazine, Sulfisoxazole, Trimethoprim-Sulfamethoxazole (sxt) (Co-trimoxazole) (TMP-SMX), Sulfonamidochrysoidine (archaic), Demeclocycline, Doxycycline, Minocycline, Oxytetracycline, Tetracycline, Clofazimine, Dapsone, Capreomycin, Cycloserine, Ethambutol(Bs), Ethionamide, Isoniazid, Pyrazinamide, Rifampicin (Rifampin in US), Rifabutin, Rifapentine, Streptomycin, Arsphenamine, Chloramphenicol(Bs), Fosfomycin, Fusidic acid, Metronidazole, Mupirocin, Platensimycin, Quinupristin/Dalfopristin, Thiamphenicol, Tigecycline(Bs), Tinidazole, and Trimethoprim(Bs).

Different antibiotics or antimicrobials may have different mechanisms of action and can affect replication propagation and replication re-initiation differently. Some bacteriostatic antibiotics (such as aminoglycosides, cephalosporins, tetracyclines, sulfonamides, and macrolides) inhibit protein synthesis, while bactericidal antibiotics can act on the cell wall (eg, vancomycin and β-lactams), or bacterial DNA (e.g., fluoroquinolones). Some antibiotics, such as trimethoprim and sulfamethoxazole interfere with a metabolic pathways and affect DNA replication indirectly, and some (nitrofurantoin) affect multiple process in a cell, including DNA replication. Some antibiotics, such as β-lactams, inhibit cell wall biosynthesis in a microorganism, which reduces cell growth and division.

In some embodiments, treatment conditions are adjusted to intensify an effect of antibiotics on DNA replication for every antibiotics group. In some embodiments, treatment conditions are adjusted to speed up observation of an effect of antibiotics on DNA replication for every antibiotics group. In some embodiments, the method described in this disclosure tests for antibiotic susceptibility though relative gene quantification.

Target Molecules

In some embodiments the methods and devices provided herein amplifiable target molecules (e.g., markers) indicative of growth of the microorganism in response to the presence or absence of an antimicrobial. Examples of amplifiable target molecules for use with the assays described herein are disclosed in International Application No. PCT/US2015/059344, "Microfluidic Measurements of the Response of an Organism to a Drug," incorporated by reference in its entirety.

In some embodiments, the amplifiable target molecule of interest is DNA. In some embodiments, DNA regions, such as those represented in multiple copies in published bacterial genomes, are selected as targets (such as rDNA). In some embodiments, more than one target (such as a DNA fragment or gene) is selected for simultaneous quantification; these targets can be located close to the origin of replication and/or can involve both directions of replication. In some embodiments, more than one target (such as a DNA fragment or gene) is selected for simultaneous quantification; one or more of these targets is located close to the origin of replication and one or more targets is far from the origin of replication. By measuring the ratio of these targets at certain times (in some cases, before replication is complete), replication can be detected rapidly in some embodiments without the need to measure the number of cells independently. This becomes valuable when very few cells are present in the sample, and or when very few cells are analyzed, and or when the accuracy with which the number of cells present in each part of a split sample is limited by Poisson statistics.

In some embodiments, detecting gene duplications due to antimicrobial treatment allows detection of susceptible strains. In some embodiments, the relative quantification of these targets with and/or without treatment with antibiotics are used to determine antibiotic susceptibility. This can enable the very rapid differentiation between resistant and susceptible strains.

By using targets close to the origin of replication, the relative copy number of those genes in total genetic material in the cells can be quantified to identify susceptible and resistant cells under antibiotic treatment earlier, e.g. prior to completion of DNA replication or prior to completion of cell division. In some embodiments, the copy number of the target genes of the susceptible microorganism treated with a drug is less than the copy number of the target genes of the resistant microorganism or the non-treated microorganism as exposure to the drug in a susceptible microorganism decreases replication. However, some antibiotics cause certain regions of chromosomal DNA to increase in copy number in susceptible cells. For example, some antibiotics (such as quinolones) induce a replication fork stalling. As a direct consequence of replication fork stalling while DNA replication initiation continues, all antibiotics targeting DNA replication up-regulate origin-proximal genes copy number and induce a global changes in transcription in bacteria. This produces a result contrary to those antibiotics that slow DNA replication in susceptible microorganisms treated with a drug, providing an increase in the number of positive results.

In some embodiments, changes in gene expression are used as markers of antimicrobial susceptibility or resistance in a microorganism. In some embodiments, drug susceptibility testing is based on RNA, such as by comparing transcription levels. In some embodiments, drug susceptibility testing is based on RNA, such as by comparing transcription levels using digital quantification. In some embodiments, markers associated with a resistance or susceptibility in response to an antimicrobial can be measured.

In some embodiments, genes differently regulated in response to a drug or antibiotic can be used. The genes can include for example, the recA and lexA (Barczak et al., 2012, Proceedings of the National Academy of Sciences, 6217-6222) genes induced by OxyR and SoxS in response to antibiotic-induced oxidative stress (Dwyer, et al., 2014, Proceedings of the National Academy of Sciences, E2100-E2109).

In susceptible bacteria, many RNA targets have been shown to be either upregulated or downregulated in response to drug exposure over a short time. Many such genes also show significant changes in expression level as a response to variations in culture conditions and from isolate to isolate. Some genes expression (e.g., recA, involved in the SOS response) are up-regulated in several species in response to multiple antibiotics, whereas other transcriptional changes are microorganism and/or mechanism specific.

Changes in RNA targets RNA levels can be difficult to detect using existing methods after a short time of drug/antibiotic treatment in bulk (such as by routine reverse transcription, qPCR, microarray analysis, RNAseq, and/or isothermal or PCR amplification) due to the presence of non-specific nucleic acids from the host's cells or from other microorganisms, as well as due to the presence of inhibitors from the clinical sample, and due to the short time of treatment. In some embodiments, binary, digital and multi-volume digital formats can be used to isolate targets in volumes where local concentration is high, enabling the fast and reliable quantification even in such samples.

In some embodiments, DNA targets with a higher copy number present in cells are quantified to enable the detection of resistance profiles even in very low numbers of cells (such as in blood or cerebral spinal fluid). For example, while in genome of most of the *E. coli* strains and isolates there are ~7 copies of rDNA. Additionally, due to the presence of at least two, but potentially numerous replication forks, one could expect to have, in some cases, from 12 to 35 rDNA copies per cell, depending on its growth rate (*E. coli* and *Salmonella*, cellular and molecular biology. Frederic C. Neidhardt, editor in Chief. v2. ASM press, Washington D.C. 1996). In some embodiments, genes with higher copy number in the cell are quantified to enable the increased statistical resolution of quantification to determine antibiotic resistance when very low numbers of cells are present. In some embodiments, this is quantification is performed by amplification. In some embodiments, this quantification makes use of digital amplification methods.

In some embodiments, additional targets are evaluated from publically available studies. In some embodiments, targets for analysis are generated from analysis of DNA/RNA-seq data. In some embodiments, quantification strategies (such as e.g. NASBA, qRT-PCR, sequencing, nanostring, among others) can be used. In some embodiments RNA from cells obtained from samples in a digital format is quantified. In some embodiments gene target expression levels in each individual cell is quantified through single cell measurements.

Sample Processing

In some embodiments, the microorganism is exposed to a drug to assay its response to the drug and determine whether the microorganism is resistant or susceptible to the drug. In some embodiments, microorganisms can be pre-cultured in or pre-exposed to a variety of matrices (such as for example bacterial culture media or human urine, among others), and can be subsequently incubated in the presence or absence of various drugs (e.g. antibiotics, such as ciprofloxacin, nitrofurantoin, trimethoprim, tetracycline, and sulfamethoxazole, and others.) where exposure to multiple drugs and/or multiple additives is performed on the same device substantially simultaneously. In some embodiments, microorganisms do not substantially divide during exposure to a drug. In some embodiments, microorganisms confined as single cells, or being in the small group and/or aggregate of cells, respond to a drug faster than an average population.

Devices and methods described herein can include those when some of the microorganisms confined as single cells, or as a small group and/or aggregate of cells, such as for example fewer than 3 cells, fewer than 10 cells, fewer than 30 cells, fewer than 100 cells in the same compartment. The volume of the compartment can be in the range of 100 fL to 1 nL, 1 nL to 100 nL, or 100 nL to 500 nL.

In some embodiments, digital assays can use the confinement of single cells from a sample into clonal isolation regions. In some embodiments, each of the isolated cells are cultured in the clonal isolation regions to generate a plurality of clonal populations from the sample. In some embodiments, the isolated cells are treated with a drug before or after expansion. In some embodiments, after culture and expansion from an isolated cell, the clonal population is divided into two or more treatment regions. As such, at least one portion of the clonal population can be treated with a drug, while another portion of the clonal population is not treated with a drug. Then, the assays described herein can be performed to determine whether the cells in the clonal population are susceptible or resistant to one or more drugs.

In some embodiments, specific culturing conditions are used to speed up a microorganism's response to a drug (e.g. quorum sensing molecules, gas partial pressures, temperature, etc.). In some embodiments, the microorganism is exposed gases or gas mixtures, e.g., containing $H_2S$, CO, and NO. Such gases are known, for example, to affect susceptibility of microorganisms to antibiotics. Such gases can be diluted with a gas mixture which could be anaerobic, aerobic, or microoxic. Such gas mixture can contain $CO_2$.

In some embodiments, co-culturing of the microorganism with eukaryotic cells and/or other microorganisms can speed up a microorganism's response to a drug.

In some embodiments, measures to control the average number and/or location and/or time of initiation of replication in culture are performed. For example, cells can be placed into high- or low-nutrient conditions prior to exposure to antibiotics. In some embodiments, the acclimatization of cells to changes in growing conditions (such as, for example, mixing infected blood with nutrient rich media) will cause variation in the rate of DNA replication or RNA expression. In some embodiments, this effect can be mitigated by the modification of growth media. In some embodiments, data analyses can allow the capture of changes in replication rates over this noise. In some embodiments, the effects of media on replication can be used to enhance the effect of a drug treatment.

In some embodiments, cells are exposed to drugs as follows: Cells are pre-cultured at 37° C. to a density of up to $10^9$ cells/mL in various matrices including Bacto Brain-Heart Infusion broth (BHI), a mix of BHI and pooled human urine, and whole human urine before being diluted and incubated with or without antibiotics, such as ciprofloxacin, nitrofurantoin, trimethoprim, tetracycline, or sulfamethoxazole. Incubations can be performed at 37° C. at starting concentrations ranging from $10^2$-$10^8$ cells/mL, and then treated with concentrations of antibiotics ranging from 0.9 µg/mL-500 µg/mL depending on the treatment. Cells are incubated with and without drugs for a period of time including 10 minutes, 15 minutes, 20 minutes, 30 minutes, 45 minutes, or 60 minutes before an aliquot of the culture is used for analysis, e.g., by nucleic acid extraction and amplification.

In some embodiments, the microorganism is exposed to a drug for a time less than 4 hours, less than 3 hours, less than 2 hours, less than 1 hour, less than 30 minutes, less than 15 minutes, less than 10 minutes, less than 5 minutes, less than 3 minutes, or less than 1 minute.

The nucleic acids can be extracted before analysis. The exact protocol used to extract nucleic acids depends on the sample and the exact assay to be performed. Extracting nucleic acids from target bacteria usually involves a cell lysis step often, but not always, followed by nucleic acid purification. The cell lysis step disrupts the cell and nuclear membranes, releasing the genetic material. This is often accomplished using a lysis detergent, such as sodium dodecyl sulfate, which also denatures the large amount of proteins present in the cells.

The nucleic acids can then be purified with an alcohol precipitation step, usually ice-cold ethanol or isopropanol, or via a solid phase purification step, typically on a silica matrix in a column, resin or on paramagnetic beads in the presence of high concentrations of a chaotropic salt, prior to washing and then elution in a low ionic strength buffer. An optional step prior to nucleic acid precipitation is the addition of a protease which digests the proteins in order to further purify the sample.

In some embodiments, nucleic acids are extracted using standard methods including a one-step DNA extraction buffer or a one-step RNA extraction buffer (available from Epicentre). Following extraction, nucleic acids were quantified using nucleic acid amplification techniques including quantitative PCR and digital PCR.

In some embodiments, the microorganisms of the sample are lysed. In some embodiments, inhibitors are removed from the sample. In some embodiments, inhibitors in the sample are inactivated. In some embodiments, the sample is exposed to conditions or reagents for preventing degradation of the nucleic acid. In some embodiments, the sample undergoes ribosomal RNA depletion. In some embodiments, unwanted RNA is removed from the sample. In some embodiments, microorganisms in the sample are treated with a reagent, such as PMA and EMA, that binds to and prevents amplification of free nucleic acids. In some embodiments, the sample is irradiated to initiate a photochemical reaction to prevent unwanted amplification of certain nucleic acids. In some embodiments, extracted nucleic acids are further purified prior to quantification.

In some embodiments sample preparation before the quantification reaction takes less than two hours, less than one hour, less than 30 minutes, less than 15 minutes, less than 10 minutes, less than 5 minutes, less than 3 minutes, less than 2 minutes, less than 1 minute, or less than 30 seconds In some embodiments techniques, such as denaturation, restriction digestion, fragmentation, digestion of replicated DNA fragments, digestion of RNA, or digestion of DNA, are used before digital quantification. This enables enhanced isolation of individual genes into individual volumes for detection and amplification. In some embodiments, a restriction digest in between genes can be used to facilitate isolation into individual volumes of DNA molecules carrying target genes. For example, in some embodiments, when rDNA in *E. coli* is used as the target with 7 copies per genome, a digital experiment can only show one positive volume per large genome fragment. When the genome is denatured, fragmented, and/or digested, each gene could be isolated into individual volumes, giving 24 to 70 template-positive volumes for analyses in a device from a single genome.

In some embodiments agents inhibiting amplification of nucleic acids from dead cells are used (e.g., propidium monoazide (PMA) or ethidium monoazide). In some embodiments, cells are treated with such agents inhibiting amplification of nucleic acids from dead cells prior to incubation with antibiotics. In some embodiments, cells are treated with such agents inhibiting amplification of nucleic acids from dead cells after incubation with antibiotics.

In some embodiments, a restriction digest of chromosomal DNA is done prior to quantification, such as to separate fragments of DNA containing multiple replicated copies of the target gene while preserving the fragments of interest to be suitable for detection and quantification.

In some embodiments, one or more denaturation steps are done, such as to duplicate the number of positive templates (for example if in a given sample *E. coli* cells could have from 12 to 35 copies of rDNA genes under certain conditions (depending on a growth rate, individual ages and individual states)—and yield for example 24-70 fragments after denaturation; this can in some cases improve visualization in digital approaches.)

In some embodiments, denaturation or digestion can be used to separate DNA at replication forks—pieces of newly replicated DNA can partition into different wells—such as to increase the resolution between inhibited cells and actively replicating cells.

In some embodiments, digital assays can use the confinement of a few or single target nucleic acid molecules into individual reaction volumes. Prior to the completion of replication, denaturing agents (such as e.g. heat, urea, Guanidinium Chloride, acids, bases, mechanical strain, enzymes, restriction enzymes, among others) can be used to enhance the separation of target DNA strands into independent volumes. This can be of particular use for example in cases where multiple target regions are present within a single genome.

In some embodiments, denaturation of a whole chromosomal DNA is performed before performing digital quantification.

Amplification

In some embodiments, a nucleic acid amplification reaction is performed to amplify the amplifiable target molecule (e.g., a target nucleic acid). Amplification reaction can include polymerase chain reaction (PCR), nucleic acid sequence based amplification (NASBA), self-sustained sequence replication (3SR), loop mediated isothermal amplification (LAMP), strand displacement amplification (SDA), whole genome amplification, multiple displacement amplification, strand displacement amplification, helicase dependent amplification, nicking enzyme amplification reaction, recombinant polymerase amplification, reverse transcription PCR or ligation mediated PCR. Amplification or detection methods for nucleic acids can include but are not limited to PCR, RT-PCR, or other methods including isothermal amplification methods. Isothermal nucleic acid amplification methods can include but are not limited to strand displacement amplification (SDA), transcription mediated amplification, nucleic acid sequence based amplification (NASBA), recombinase polymerase amplification (RPA), rolling circle amplification, ramification amplification, helicase-dependent isothermal DNA amplification, loop mediated isothermal amplification (LAMP), methods based on both signal amplification and target amplification such as branched-DNA-based detection methodologies, hybridization chain reaction, or nucleic acid-based logic gates and DNA circuits (see, e.g., Qian and Winfree, Scaling Up Digital Circuit Computation with DNA Strand Displacement Cascades, Science 2011; 6034: 1196-1201). Further examples of such amplification chemistries are described in, for example, ("Isothermal nucleic acid amplification technologies for point-of-care diagnostics: a critical review, Pascal Craw and Wamadeva Balachandrana Lab Chip, 2012, 12, 2469-2486, DOI: 10.1039/C2LC40100B,") incorporated here in its entirety by reference. Isothermal amplification methods that operate at temperatures lower than PCR operating temperatures can be used, e.g., to improve compatibility of restriction enzymes with the amplification process if the restriction enzyme is not sufficiently stable under typical PCR operating temperatures.

The amplification reaction assay can be PCR. PCR is well known in this field and comprehensive description of this type of reaction is provided in E. van Pelt-Verkuil et al., Principles and Technical Aspects of PCR Amplification, Springer, 2008.

In embodiments using PCR, the components of the reaction can be in contact with sample. The components of the reaction can be added to a container that holds the sample. The components of the reaction can be present in a container, and the sample can be added. In some embodiments, a kit can comprise a plurality of small containers, at least one container holding the components of a PCR reaction. A kit can comprise a SlipChip and the components of the reaction.

PCR typically involves placing these reactants in a small tube (~10-50 microliters) containing the extracted nucleic acids. The tube is placed in a thermal cycler; an instrument that subjects the reaction to a series of different temperatures for varying amounts of time. The standard protocol for each thermal cycle involves a denaturation phase, an annealing phase, and an extension phase. The extension phase is sometimes referred to as the primer extension phase. In addition to such three-step protocols, two-step thermal protocols can be employed, in which the annealing and extension phases are combined. The denaturation phase typically involves raising the temperature of the reaction to 90-95° C. to denature the DNA strands; in the annealing phase, the temperature is lowered to ~50-60° C. for the primers to anneal; and then in the extension phase the temperature is raised to the optimal DNA polymerase activity temperature of 60-72° C. for primer extension. This process is repeated cyclically around 20-40 times, the end result being the creation of millions of copies of the target sequence between the primers.

The amplification reaction assay can be a variant of PCR. The amplification reaction assay can be selected from the group of variants to the standard PCR protocol such as multiplex PCR, linker-primed PCR, direct PCR, tandem PCR, real-time PCR and reverse-transcriptase PCR, amongst others, which have been developed for molecular diagnostics.

The amplification reaction assay can be multiplex PCR. Multiplex PCR uses multiple primer sets within a single PCR mixture to produce amplicons of varying sizes that are specific to different DNA sequences. By targeting multiple genes at once, additional information can be gained from a single test-run that otherwise would require several experiments.

In some embodiments, a multiplexed PCR reaction is performed where a plurality of primer sets are added to a reaction mixture and each amplify their specified target within the same volume, for example. In other embodiments a sample is split into a plurality of smaller volumes into which single primer sets are introduced.

The amplification reaction assay can be linker-primed PCR, also known as ligation adaptor PCR. Linker-primed PCR is a method used to enable nucleic acid amplification of essentially all DNA sequences in a complex DNA mixture without the need for target-specific primers. The method firstly involves digesting the target DNA population with a suitable restriction endonuclease (enzyme). Double-stranded oligonucleotide linkers (also called adaptors) with a suitable overhanging end are then ligated to the ends of target DNA fragments using a ligase enzyme. Nucleic acid amplification is subsequently performed using oligonucleotide primers which are specific for the linker sequences. In this way, all fragments of the DNA source which are flanked by linker oligonucleotides can be amplified.

The amplification reaction assay can be direct PCR. Direct PCR describes a system whereby PCR is performed directly on a sample without any, or with minimal, nucleic acid extraction. With appropriate chemistry and sample concentration it is possible to perform PCR with minimal DNA purification, or direct PCR. Adjustments to the PCR chemistry for direct PCR include increased buffer strength, the use of polymerases which have high activity and processivity, and additives which chelate with potential polymerase inhibitors.

The amplification reaction assay can be tandem PCR. Tandem PCR utilizes two distinct rounds of nucleic acid amplification to increase the probability that the correct amplicon is amplified. One form of tandem PCR is nested PCR in which two pairs of PCR primers are used to amplify a single locus in separate rounds of nucleic acid amplification. The amplification reaction assay can be nested PCR. The first pair of primers hybridize to the nucleic acid sequence at regions external to the target nucleic acid sequence. The second pair of primers (nested primers) used in the second round of amplification bind within the first PCR product and produce a second PCR product containing the target nucleic acid, that can be shorter than the first one. The logic behind this strategy is that if the wrong locus were amplified by mistake during the first round of nucleic acid amplification, the probability is very low that it would also be amplified a second time by a second pair of primers and thus increases specificity.

The amplification reaction assay can be real-time PCR. The amplification reaction assay can be quantitative PCR. Real-time PCR, or quantitative PCR, is used to measure the quantity of a PCR product in real time. By using a fluorophore-containing probe or fluorescent dyes along with a set of standards in the reaction, it is possible to quantify the starting amount of nucleic acid in the sample. This is particularly useful in molecular diagnostics where treatment options can differ depending on the pathogen load in the sample.

The amplification reaction assay can be reverse-transcriptase PCR (RT-PCR). Reverse-transcriptase PCR (RT-PCR) is used to amplify DNA from RNA. Reverse transcriptase is an enzyme that reverse transcribes RNA into complementary DNA (cDNA), which is then amplified by PCR. RT-PCR can be used in expression profiling, to determine the expression of a gene or to identify the sequence of an RNA transcript, including transcription start and termination sites. It can be used to amplify RNA viruses such as human immunodeficiency virus or hepatitis C virus.

Furthermore, detection methods based on both signal amplification and target amplification, such as branched-DNA-based detection methodologies, can be used in this approach. For example, for branched-DNA-based detection methodologies, using an enzyme that can cleave the target in a position located between two positions used for binding of the capture extender and the label extender (e.g., as described in Tsongalis, Branched DNA Technology in Molecular Diagnostics, *Am J Clin Pathol* 2006; 126: 448-453), can reduce the signal obtained in the assay when a restriction enzyme recognizes and cleaves the target.

The amplification reaction assay can be Strand Displacement Amplification (SDA). Strand Displacement Amplification (SDA) can rely on the ability of certain restriction enzymes to nick the unmodified strand of hemi-modified DNA and the ability of a 5'-3' exonuclease-deficient polymerase to extend and displace the downstream strand. Exponential nucleic acid amplification can then achieved by coupling sense and antisense reactions in which strand displacement from the sense reaction serves as a template for the antisense reaction. The use of nickase enzymes which do not cut DNA in the traditional manner but produce a nick on one of the DNA strands, such as N. Alwl, N. BstNB 1 and Mlyl, for example, can be used in this reaction. SDA has been improved by the use of a combination of a heat-stable restriction enzyme (Aval) and heat-stable Exo-polymerase (Bst polymerase). This combination has been shown to increase amplification efficiency of the reaction from 108 fold amplification to 1010 fold amplification so that it is possible using this technique to amplify unique single copy molecules.

The amplification reaction assay can be Transcription Mediated Amplification (TMA). The amplification reaction assay can be Nucleic Acid Sequence Based Amplification (NASBA). Transcription Mediated Amplification (TMA) and Nucleic Acid Sequence Based Amplification (NASBA) can use an RNA polymerase to copy RNA sequences but not corresponding genomic DNA. The technology can use two primers and two or three enzymes, RNA polymerase, reverse transcriptase and optionally RNase H (if the reverse transcriptase does not have RNase activity). One primer can contain a promoter sequence for RNA polymerase. In the first step of nucleic acid amplification, this primer hybridizes to the target ribosomal RNA (rRNA) at a defined site. Reverse transcriptase can create a DNA copy of the target rRNA by extension from the 3' end of the promoter primer. The RNA in the resulting RNA:DNA duplex can be degraded by the RNase activity of the reverse transcriptase if present or the additional RNase H. Next, a second primer binds to the DNA copy. A new strand of DNA is synthesized from the end of this primer by reverse transcriptase, creating a double-stranded DNA molecule. RNA polymerase recognizes the promoter sequence in the DNA template and initiates transcription. Each of the newly synthesized RNA amplicons re-enters the process and serves as a template for a new round of replication.

The amplification reaction assay can be Recombinase Polymerase Amplification (RPA). In Recombinase Polymerase Amplification (RPA), the isothermal amplification of specific DNA fragments is achieved by the binding of opposing oligonucleotide primers to template DNA and their extension by a DNA polymerase. Heat is not always required to denature the double-stranded DNA (dsDNA) template. Instead, RPA can employ recombinase-primer complexes to scan dsDNA and facilitate strand exchange at cognate sites. The resulting structures are stabilized by single-stranded DNA binding proteins interacting with the displaced template strand, thus preventing the ejection of the primer by branch migration. Recombinase disassembly leaves the 3' end of the oligonucleotide accessible to a strand displacing DNA polymerase, such as the large fragment of *Bacillus subtilis* Pol I (Bsu), and primer extension ensues. Exponential nucleic acid amplification is accomplished by the cyclic repetition of this process.

The amplification reaction assay can be Helicase-dependent amplification (HDA). Helicase-dependent amplification (HDA) mimics the in vivo system in that it uses a DNA helicase enzyme to generate single-stranded templates for primer hybridization and subsequent primer extension by a DNA polymerase. In the first step of the HDA reaction, the helicase enzyme traverses along the target DNA, disrupting the hydrogen bonds linking the two strands which are then bound by single-stranded binding proteins. Exposure of the single-stranded target region by the helicase allows primers to anneal. The DNA polymerase then extends the 3' ends of each primer using free deoxyribonucleoside triphosphates (dNTPs) to produce two DNA replicates. The two replicated dsDNA strands independently enter the next cycle of HDA, resulting in exponential nucleic acid amplification of the target sequence.

The amplification reaction assay can be Rolling Circle Amplification (RCA). Other DNA-based isothermal techniques include Rolling Circle Amplification (RCA) in which a DNA polymerase extends a primer continuously around a circular DNA template, generating a long DNA product that consists of many repeated copies of the circle. By the end of the reaction, the polymerase generates many thousands of copies of the circular template, with the chain of copies tethered to the original target DNA. This allows for spatial resolution of target and rapid nucleic acid amplification of the signal. Up to 1012 copies of template can be generated in 1 hour. Ramification amplification is a variation of RCA and utilizes a closed circular probe (C-probe) or padlock probe and a DNA polymerase with a high processivity to exponentially amplify the C-probe under isothermal conditions.

The amplification reaction assay can be Loop-mediated isothermal amplification (LAMP). LAMP offers high selectivity and employs a DNA polymerase and a set of four specially designed primers that recognize a total of six distinct sequences on the target DNA. An inner primer containing sequences of the sense and antisense strands of the target DNA initiates LAMP. The following strand displacement DNA synthesis primed by an outer primer releases a single-stranded DNA. This serves as template for DNA synthesis primed by the second inner and outer primers that hybridize to the other end of the target, which produces a stem-loop DNA structure. In subsequent LAMP cycling one inner primer hybridizes to the loop on the product and initiates displacement DNA synthesis, yielding the original stem-loop DNA and a new stem-loop DNA with a stem twice as long. The cycling reaction continues with accumulation of many copies of target in less than an hour. The final products are stem-loop DNAs with several inverted repeats of the target and cauliflower-like structures with multiple loops formed by annealing between alternately inverted repeats of the target in the same strand.

In some embodiments, the amplification is a one-step digital reverse-transcription loop-mediated isothermal amplification (dRT-LAMP) reaction for quantifying mRNA with all reactions performed. LAMP produces a bright fluorescence signal through replacement of manganese with magnesium in calcein. In some embodiments, this fluorescence can then be detected and counted using a commercial cell phone camera.

Nucleic acid-based logic gates and DNA circuits can be used for nucleic acid amplification. The use of restriction enzymes with nucleic acid-based logic gates and DNA circuits can reduce or stop the intrinsic leakage problem for DNA networks. Combining the molecular recognition ability of both restriction enzymes and DNA networks, restriction enzyme logic gates can be highly active components for the design and construction of biocomputational devices (see e.g., Qian and Winfree, Scaling Up Digital Circuit Computation with DNA Strand Displacement Cascades, Science 2011; 6034: 1196-1201).

In some embodiments the amplification employed can take place in a variety of different mediums, such as for example, aqueous solution, polymeric matrix, solid support, etc.

Isothermal Amplification for AST Determination

In some embodiments, LAMP primers specific to the target pathogen are designed. In some embodiments, the target pathogen is *E. coli*. In some embodiments, other amplification chemistries are employed to specifically detect the pathogen, such as PCR, NASBA, HDA, MDA, or RPA.

In some embodiments, pathogen identification and initial quantification of one or more AST markers are performed using quantitative real-time NA amplification methods, where the fluorescence intensity is tracked in real-time and a standard curve is used to calculate the relative concentration.

In some embodiments, one or more of (i) pathogen identification, (ii) initial quantification of one or more AST markers, and (iii) AST marker quantification are performed using binary quantification methods, e.g., digital NA amplification.

FIG. 1 shows an example of an experimental workflow of the dAST method. Urine samples are incubated without and with antibiotics (ABX) (steps 1-2). AST markers are quantified in control (−ABX) and treated (+ABX) samples (step 3); and control-treated (CT) ratios are analyzed (step 4). Antibiotic susceptibility is determined by measuring the quantity of a specific nucleic acid sequence (AST marker) in the control and treated samples to generate a CT ratio. In some embodiments, the different samples are loaded into their respective reaction areas simultaneously.

In some embodiments, a value other than the CT ratio could be used to determine the susceptibility of a pathogen. In some embodiments, the CT ratio and AST determination could be measured and calculated only using a set endpoint of the reaction.

In some embodiments, if there is a small delay in time-to-positives (TTP) from one chip relative to the other, the TTP peak of the control and treated chip are aligned to normalize the data. This gives a more accurate representation of the concentrations at each time point and the control and treated concentrations can be compared to calculate a CT ratio.

In some embodiments, inefficient amplification on a chip can be detected if there is a greater than 4× difference in the control and treated chips. When measuring *E. coli* DNA concentration after 15 minutes of antibiotic exposure, the control sample should not have more than 3 times the DNA concentration of the treated sample. For example, if the DNA of the treated sample is quantified as 100 copies/μL and the DNA of the control sample is quantified as 500 copies/μL, then this would be evidence that there was an abnormality or inefficient amplification occurring and the experiment can be excluded.

Detection

Assay results can comprise a readout or detection mechanism chosen from a range of readouts used to detect progress or results of reactions, including but not limited to optical techniques, electrical techniques or magnetic techniques. Examples include but are not limited to electrochemical readouts, optical readouts, including for example fluorescence readouts, colorimetric readouts, chemiluminescence, electrical signals, quenching, probe binding, probe hybridization, metal labeling, contrast agent labeling, absorbance, mass spectrometry, sequencing, lateral flow strips, and the generation of a heterogeneous substance (e.g., precipitation, gas bubble).

A readout mechanism can comprise fluorescence. For example fluorescent dye can be used to label nucleic acids; reactions with more nucleic acid product can yield more fluorescence signal. Fluorescent dyes can include but are not limited to ethidium bromide, berberine, proflavine, daunomycin, doxorubicin, thalidomide, YOYO-1, SYBR Green I, SYBR Green II, oxazole yellow (YO), thiazole orange (TO), PicoGreen (PG), TOTO, TO-PRO, SYTOX, SYTO, other cyanine dyes, and calcein. The fluorescence intensity can be measured at an end-point or in real-time, allowing measurement of the reaction progress. For example, a given level of fluorescence can be set as the threshold for a positive signal from a digital or quasi-digital compartment.

In some cases, signal can be generated from molecules with reporter moieties and affinity moieties that are applied to digital units to bind to amplified target molecules. The reporter molecule or reporter moiety can be fluorescent. The digital units or capture regions can be washed to remove unbound reporter. In some cases, the reporter molecule can be calcein or calcein with cetyl trimethyl ammonium bromide (calcein-CTAB). In some cases, the reporter can be an intercalating dye. In some embodiments, a fluorescent probe (e.g., molecular beacon, TaqMan, or Fluorescence Resonance Energy Transfer (FRET) probe) is employed to generate a sequence-specific fluorescent signal. Fluorescent probes can be designed to hybridize specifically to the amplification product to generate a detectable signal. In some embodiments, the fluorophore is covalently attached to the termini of a polynucleotide. In some embodiments, the probe is a molecular beacon comprising a quencher.

As used herein, "molecular beacon" refers to a single stranded hairpin-shaped oligonucleotide probe designed to report the presence of specific nucleic acids in a solution. A molecular beacon consists of four components; a stem, hairpin loop, end labelled fluorophore and opposite end-labelled quencher (Tyagi et al., (1998) Nature Biotechnology 16:49-53). When the hairpin-like beacon is not bound to a target, the fluorophore and quencher lie close together and fluorescence is suppressed. In the presence of a complementary target nucleotide sequence, the stem of the beacon opens to hybridize to the target. This separates the fluorophore and quencher, allowing the fluorophore to fluoresce. Alternatively, molecular beacons also include fluorophores that emit in the proximity of an end-labelled donor. "Wavelength-shifting Molecular Beacons" incorporate an additional harvester fluorophore enabling the fluorophore to emit more strongly. Current reviews of molecular beacons include Wang et al., 2009, *Angew Chem Int Ed Engl*, 48(5):856-870; Cissell et al., 2009, *Anal Bioanal Chem* 393(1):125-35; Li et al., 2008, *Biochem Biophys Res Comm* 373(4):457-61; and Cady, 2009, *Methods Mol Biol* 554:367-79.

Amplifiable target molecules can be labeled with enzymes which can produce an electrical signal, for example by electro-activating a substrate molecule which can be oxidized and reduced. Labeling can occur by binding with an affinity agent, for example as in a sandwich assay. Labeling can occur by intercalating dyes.

A readout mechanism can comprise mass spectrometry. For example, nucleic acids of different sizes (e.g. from restriction digestion or ligation) can be distinguished and/or counted by mass spectrometry. Alternatively, a readout mechanism can operate without mass spectrometry.

A readout mechanism can comprise electrophoresis, including gel electrophoresis. For example, nucleic acids of different sizes (e.g. from restriction digestion or ligation) can be identified or distinguished by electrophoresis. Alternatively, a readout mechanism can operate without electrophoresis.

A readout mechanism can comprise sequencing. Sequencing, or sequence determination techniques, can be performed by methods including but not limited to Sanger sequencing, Illumina (Solexa) sequencing, pyrosequencing, next generation sequencing, Maxam-Gilbert sequencing, chain termination methods, shotgun sequencing, or bridge PCR; next generation sequencing methodologies can comprise massively parallel signature sequencing, polony sequencing, SOLiD sequencing, Ion Torrent semiconductor sequencing, DNA nanoball sequencing, Heliscope single molecule sequencing, single molecule real time (SMRT) sequencing, nanopore DNA sequencing, tunneling currents DNA sequencing, sequencing by hybridization, sequencing with mass spectrometry, microfluidic Sanger sequencing, microscopy-based techniques, RNA polymerase sequencing or in vitro virus high-throughput sequencing.

The signal can be electromagnetic. The signal can comprise the presence or absence of a physical object, such as a bead. Amplified target molecules can be labeled with a fluorescent agent or a contrast agent. Amplified target molecules can be labeled with enzymes which can produce a fluorescent signal. Amplified target molecules can be labeled with enzymes which can produce a color change in a substrate, producing a colorimetric signal. In some cases, signal can be generated from reporter molecules that are bound to affinity molecules and applied to digital units to bind to the amplified target molecules.

Sequencing reads can be used to identify reaction products, and the number of sequencing reads generated for a given nucleic acid product can be used to evaluate the reaction. For example, a given number of sequencing reads can be set as the threshold for a positive signal from a digital or quasi-digital compartment. Alternatively, a readout mechanism can operate without sequencing.

Multiplexed signal detection ensure that in multiplexed signal detection there is the ability to distinguish the amplification of many signals within the same volume as well as the ability to distinguish different signals from different volumes.

Binary Quantification/Digital Amplification

In some embodiments, the methods and assays described herein use binary quantification methods, including digital methods. Digital methods, such as digital amplification of one or more populations of digital samples, enable quantification of targets in samples containing low concentrations of cells (such as for example, when a sample (e.g. blood) has low concentrations of a pathogen (e.g. 1 bacterial cell per mL or 10 cells/mL) in a range that is still clinically relevant or even represent a life threatening illness). In some embodiments, the digital methods described herein can be used to ensure reliable quantification for resolution between susceptible and resistant cells.

The process of binary quantification begins with a sample that can contain a target analyte (e.g., an amplifiable target analyte). The target analyte can be a molecule to be quantified or searched for, for instance a particular nucleic acid, a particular nucleic acid sequence, a gene, or a protein, for example. The sample can be partitioned into many separate reaction volumes. In some embodiments, the reaction volumes are separate analysis regions. In some embodiments, the separate reaction volumes are physically separated in separate wells, chambers, areas on the surface of a slide, droplets, beads, or aliquots, for example. In some embodiments, the separate reaction volumes can be in the same container, for instance, the target analyte can be affixed to a substrate or attached to a bead. The reaction volumes can be on beads, on the surface of a slide, or attached to a substrate. The sample is distributed to many separate reaction volumes such that some, but not all of the reaction volumes generate a positive signal.

The sample is distributed to many separate reaction volumes such that each individual reaction volume contains a number of target analytes either below or above the threshold value for generating a positive signal. Generation of a positive signal from a reaction volume can depend on the number or concentration of target analytes captured, trapped, or bound by that reaction volume. In some cases, a threshold number of target analytes captured, trapped, or bound by a reaction volume allows a positive signal to be generated from that reaction volume. The threshold number of target analytes (e.g., amplifiable target molecules) to allow positive signal generation can be at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more target analytes. The threshold number of target analytes to allow positive signal generation can be at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 target analytes. In some cases, the threshold number of target analytes to allow positive signal generation can be from 1 to 19 target analytes. In some cases, the threshold number of target analytes to allow positive signal generation can be from 2 to 19 target analytes. In some cases, the threshold number of target analytes to allow positive signal generation can be from 3 to 19 target analytes. In some cases, the threshold number of target analytes to allow positive signal generation can be from 4 to 19 target analytes. In some cases, the threshold number of target analytes to allow positive signal generation can be from 5 to 19 target analytes. In some cases, the threshold number of target analytes to allow positive signal generation can be from 6 to 19 target analytes. In some cases, the threshold number of target analytes to allow positive signal generation can be from 7 to 19 target analytes. In some cases, the threshold number of target analytes to allow positive signal generation can be from 8 to 19 target analytes. In some cases, the threshold number of target analytes to allow positive signal generation can be from 9 to 19 target analytes. In some cases, the threshold number of target analytes to allow positive signal generation can be from 10 to 19 target analytes. In some cases, a threshold concentration of analytes captured, trapped, or bound by a reaction volume allows a positive signal to be generated from that reaction volume. The threshold concentration of target analytes to allow positive signal generation can be at least about zero zeptomolar (zM), 1 zM, 10 zM, 100 zM, 1 attomolar (aM), 10 aM, 100 aM, 1 femtomolar (fM), 10 fM, 100 fM, 1 pM, 10 pM, 100 pM, 1 nM, 10 nM, 100 nM, 1 µM, 10 µM, 100 µM, 1 mM, 10 mM, 100 mM, 1 M, or more. The threshold concentration of target analytes to allow positive signal generation can be at most about 1, fM, 10 fM, 100 fM, 1 pM, 10 pM, 100 pM, 1 nM, 10 nM, 100 nM, 1 µM, 10 µM, 100 µM, 1 mM, 10 mM, 100 mM, 1 M, or less. The threshold number or concentration of target analytes to allow positive signal generation from a reaction volume can be controlled. Inhibitors can be used with reaction volumes to control the threshold number or concentration. For example, the number or concentration of target analytes can be required to be higher than the number or concentration of inhibitors in a reaction volume in order for a signal to be produced from that reaction volume.

In some cases, the probability of a positive signal being generated from a reaction volume depends on the number or concentration of target analytes captured, trapped, or bound by that reaction volume. The probability of a positive signal being generated from a reaction volume can be controlled. For example, the efficiency of a signal generating reaction can be controlled, thereby controlling the probability of signal generation; a lower efficiency reaction can result in a lower probability of signal generation for a given number or concentration of target analytes.

In some embodiments, the sample is distributed to many separate reaction volumes such that each individual reaction volume contains either zero individual occurrences of the target analyte, or one or more individual occurrences of the target analyte. One or more molecules can mean a non-zero number of molecules. One or more molecules can mean one molecule. In some embodiments, one or more molecules can mean one molecule, two molecules, three molecules, four molecules . . . etc. In some embodiments, each separate reaction volume is contained in a well. In some embodiments, the sample is distributed such that each reaction volume, on average comprises less than one individual molecule of the target analyte. In some embodiments, the sample is distributed such that most reaction volumes comprise either zero or one molecules of the target analyte. Next, a qualitative "yes or no" test can be done to determine whether or not each reaction volume contains one or more target analytes by reading the pattern of discrete positive and negative reaction volumes. A positive reaction volume can be a reaction volume determined to contain one or more target analytes. A positive reaction volume can be a reaction volume determined to have a signal that correlates to the presence of one or more target analytes. A positive reaction volume can be a reaction volume determined to have a signal above a threshold that correlates to the presence of one or more target analyte. In some embodiments, a positive reaction volume is quantified as 1, or a simple multiple of 1 such as 2, 3, etc. while a negative reaction volume is quantified as 0, or less than a threshold. In some embodiments, a positive reaction volume is quantified as 1 and a negative reaction volume is quantified as 0. A negative reaction volume can be a reaction volume determined to contain zero target analyte. A negative reaction volume can be a reaction volume that does not have a signal that correlates to the presence of one or more target analyte. A negative reaction volume can be a reaction volume that does not have a signal above the threshold that correlates to the presence of one or more target analyte. The determination and/or designation of each reaction volume as a positive or a negative reaction volume can be referred to as a binary assay or a digital assay. This "yes or no test" or test like this can be referred to as a binary assay. This qualitative analysis of which reaction volume are negative reaction volume and which reaction volume are positive reaction volume can then be translated into a quantitative concentration of target analyte in the sample using Poisson analysis. A high dynamic range can be achieved through using many reaction volumes. A high dynamic range can be achieved by using a device that has reaction volume of different sizes. A high dynamic range can be achieved by partitioning the sample into many wells and/or into wells of different sizes.

This overall process can be called binary quantification of nucleic acids. This process can be called counting numbers of target analytes (e.g., amplifiable target molecules). In some embodiments, binary quantification is the process of partitioning a sample into a plurality of reaction volume such that each reaction volume contains either zero or a non-zero number of target analyte; determining and/or designating which reaction volume are positive reaction volume and which reaction volume are negative reaction volume with respect to the target analyte; and translating the information about positive and negative reaction volume into information about the quantity or concentration of the target analyte in the sample. In some embodiments, the absolute number of target analyte is determined. In some embodiments, the translation of the information about which reaction volume are positive reaction volume and which reaction volume are negative reaction volume to information about the amount, absolute number of molecules, or concentration of the target analyte in the sample is called digital quantification of the target analyte. In some embodiments, the target analyte is a nucleic acid. In some embodiments, the binary quantification of nucleic acids is achieved. In some embodiments, binary quantification of a nucleic acid target analyte is determined wherein the sample is partitioned into several reaction volumes, wherein the reaction volumes are on a SlipChip.

In some embodiments, a binary quantification of target analyte in a sample can be achieved without spatially separating the sample into multiple reaction volumes. In these embodiments, the target analyte can be counted by informational separation. In some embodiments, target analyte in the sample undergo a binary quantification through a process wherein the target analyte are tagged with a pool of information-carrying molecules, amplified or copied, and the number of distinct information-carrying molecules that were amplified or copied is counted in to get a quantification of the starting number of target analyte (see e.g. WO/2012/148477). In some embodiments, the information-carrying molecule can be a pool of chemical barcodes. In some embodiments, the information-carrying molecule can be a set of nucleic acid sequences.

Digital methods such as digital amplification can be achieved using the polymerase chain reaction (PCR), recombinant polymerase amplification (RPA), and loop mediated amplification (LAMP) as a way of quantifying RNA or DNA concentrations. Amplifications such as RPA and LAMP, which can use isothermal chemistries, can be well suited for home and limited-resource setting use. LAMP chemistry in particular is an attractive candidate for use in a home or limited-resource setting platform as it can have a relatively broad temperature tolerance range, can work with simple and cheap chemical-based heaters and phase-change materials, and can have a fluorescence gain with positive wells.

To explore the tradeoffs among antibiotic exposure time, growth rate of the bacteria in question, and resolution power of quantitative real-time PCR or digital PCR, a simple model informs optimal AST methods when DNA is used as a marker.

Suppose:
1) A bacteria sample with initial concentration of a genetic marker, Co, incubated in media for $t_{inc}$ [min] grows with a doubling time of $t_{double}$ [min].
2) A susceptible bacteria sample incubated in media with antibiotics does not grow at all. (A resistant bacteria sample would grow with the same or similar rate as the untreated sample).

Then, the ratio of the bacteria sample treated with and without antibiotics, f, would be:

$$f = \frac{C_{untreated}(t)}{C_{treated}(t)} = \frac{C_0 \cdot 2^{t_{inc}/t_{double}}}{C_0} 2^{t_{inc}/t_{double}}$$

Figure 3:
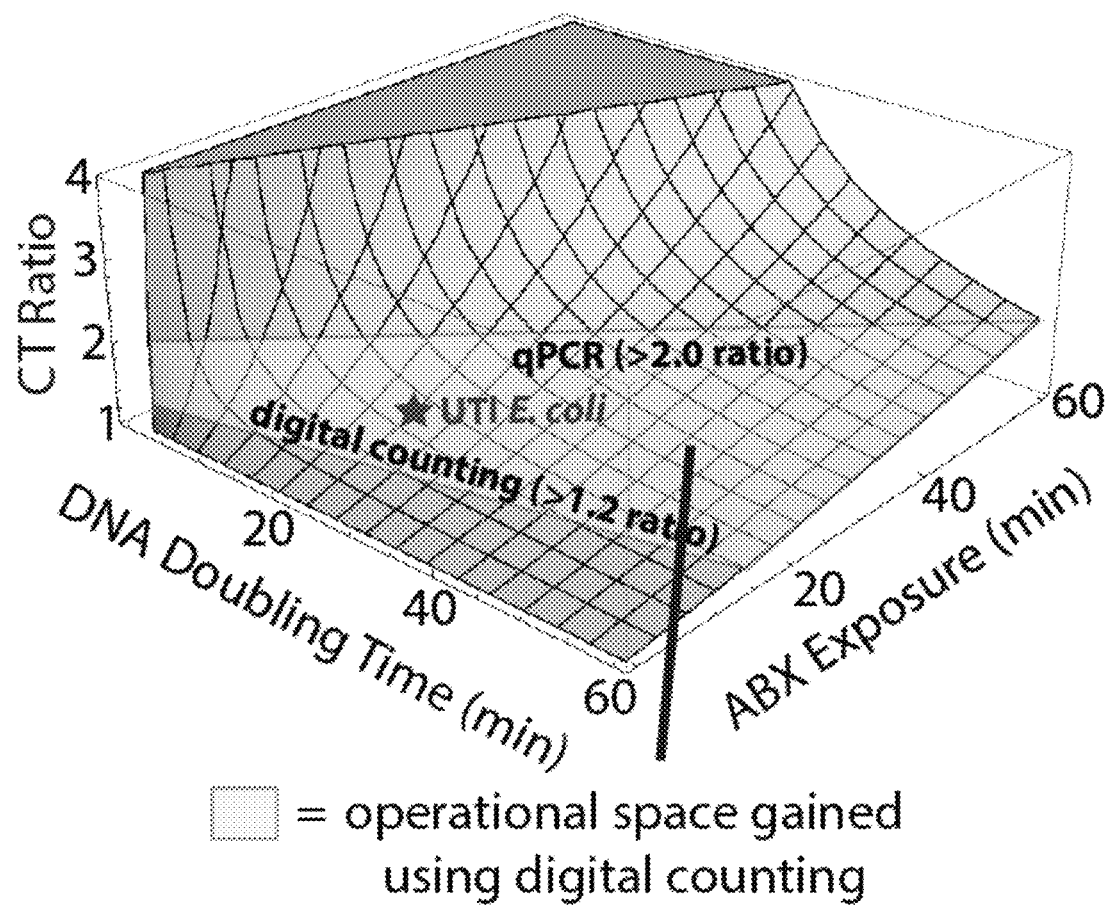
FIG. 3 illustrates a theoretical model that predicts a control-to-treated (CT) ratio as a function of pathogen DNA doubling time and antibiotic (ABX) exposure time. The operational space gained by using digital counting compared with quantitative PCR (qPCR) is highlighted.

Plotting f as a function of $t_{inc}$ and $t_{double}$ yields FIG. 3. FIG. 3 shows a theoretical model that predicts a CT ratio as a function of pathogen DNA doubling time and ABX exposure time. The operational space gained by using digital counting compared with quantitative PCR (qPCR) is highlighted.

Typically, qPCR is capable of resolving 2-fold differences in concentration, whereas digital PCR can resolve as low as 1.2-fold differences in concentration. Due to the higher resolving power of digital PCR, phenotypic AST can be done with shorter antibiotic exposure times. For example, a bacterium with a doubling time of 30 minutes would require 30 minutes to achieve a two-fold difference in concentration and thus be detectable by qPCR. On the other hand, dPCR can resolve 1.2-fold differences and therefore would only require that the bacteria be exposed to antibiotics for 11.4 minutes. Note that this model does not take into account details of chromosome replication and segregation and is provided for DNA markers for illustration purposes only.

Figure 4:
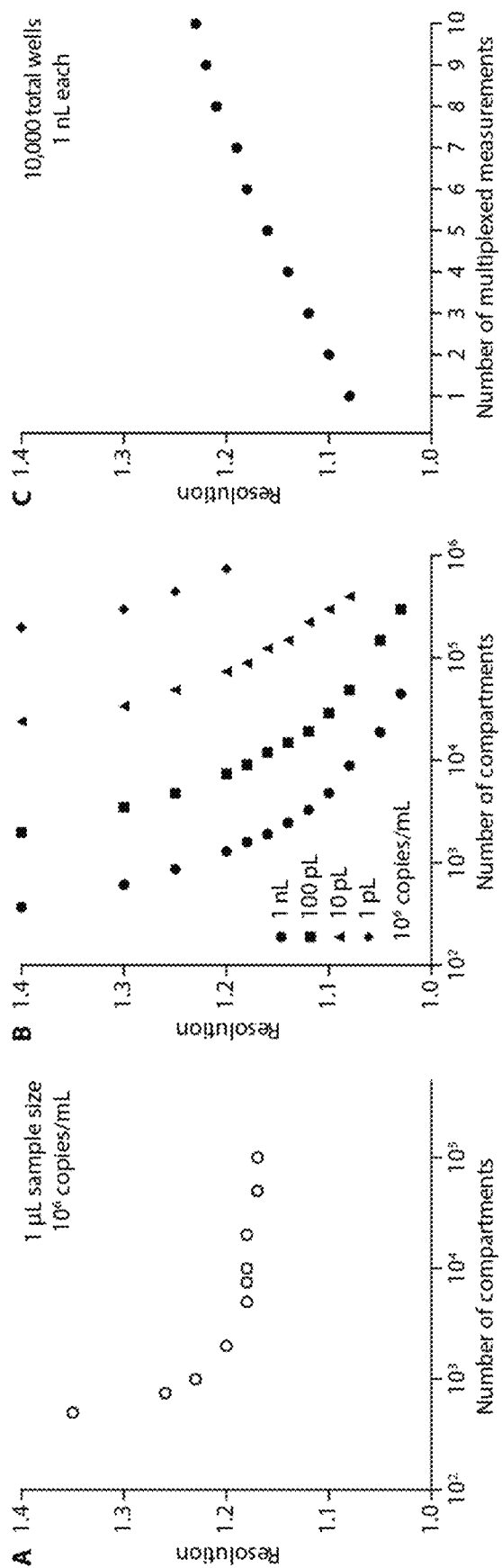
FIG. 4 shows the resolution of digital quantification depends on the number and volume of compartments. Simulations were performed with the methods described in Kreutz et al., *Anal. Chem.* 83, 8158-8168 (2011). A) For a fixed sample size, and fixed input concentration of $10^6$ cop/mL relevant to UTIs, increasing the number of compartments (and reducing the volume of each compartment accordingly) beyond 1,000 does not improve resolution in a useful way. B) For fixed compartment volume, and fixed input concentration of $10^6$ copy/mL relevant to UTIs, the resolution improves with increasing number of compartments, although this increase requires a larger input of sample and amplification reagents. C) Dependence of resolution on the number of multiplexed measurements made for a constant number of total wells. For example, while 10,000 of 1 nL compartments provide 1.08 resolution, 2,000 of 1 nL compartments provide 1.16 resolution each, enabling a 4-plex dAST (1 control and 4 ABX treated samples) to be performed.

The resolution of digital quantification depends on the number and volume of compartments. Simulations were performed with the methods described in Kreutz et al. (2011). FIG. 4 shows the results of those simulations. As shown in FIG. 4, panel A), for a fixed sample size, and fixed input concentration of $10^6$ copies/mL relevant to UTIs, increasing the number of compartments (and reducing the volume of each compartment accordingly) beyond 1,000 does not improve resolution in a useful way. As shown in FIG. 4, panel B), for fixed compartment volume, and fixed input concentration of $10^6$ copy/mL relevant to UTIs, the resolution improves with increasing number of compartments, although this increase requires a larger input of sample and amplification reagents. As shown in FIG. 4, panel C), dependence of resolution on the number of multiplexed measurements made for a constant number of total wells. For example, while 10,000 of 1 nL compartments provide 1.08 resolution, 2,000 of 1 nL compartments provide 1.16 resolution each, enabling a 4-plex dAST (1 control and 4 ABX treated samples) to be performed on a 10,000 well chip.

In some embodiments, the methods described herein include determining a concentration of a target molecule in a sample using a ratio of TTPs between populations of digital samples determined before all digital samples have completed the reaction.

Figure 5:
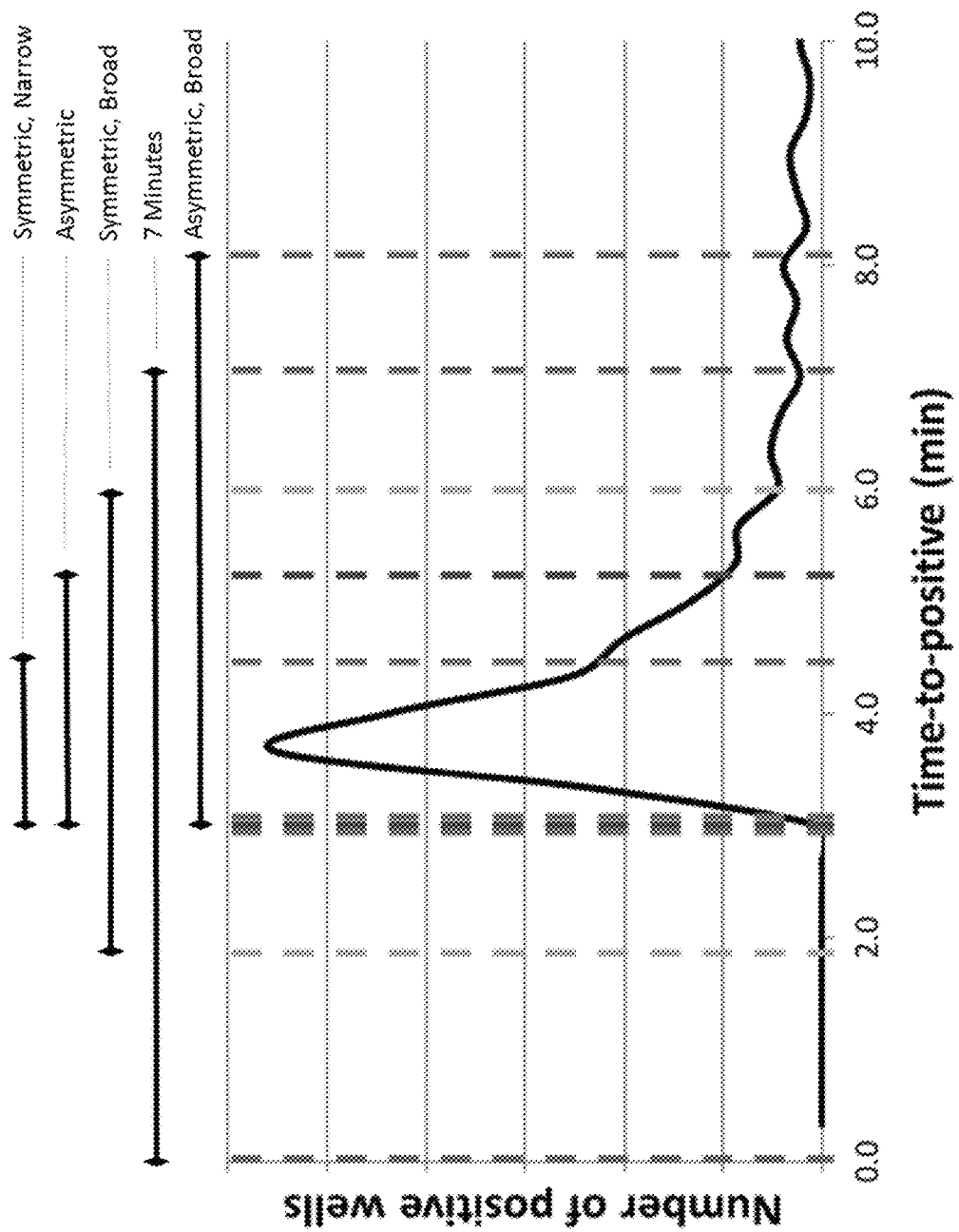
FIG. 5 provides an example time-to-positive (TTP) distribution and methods for predicting endpoint concentration at various TTPs.
Figure 6A:
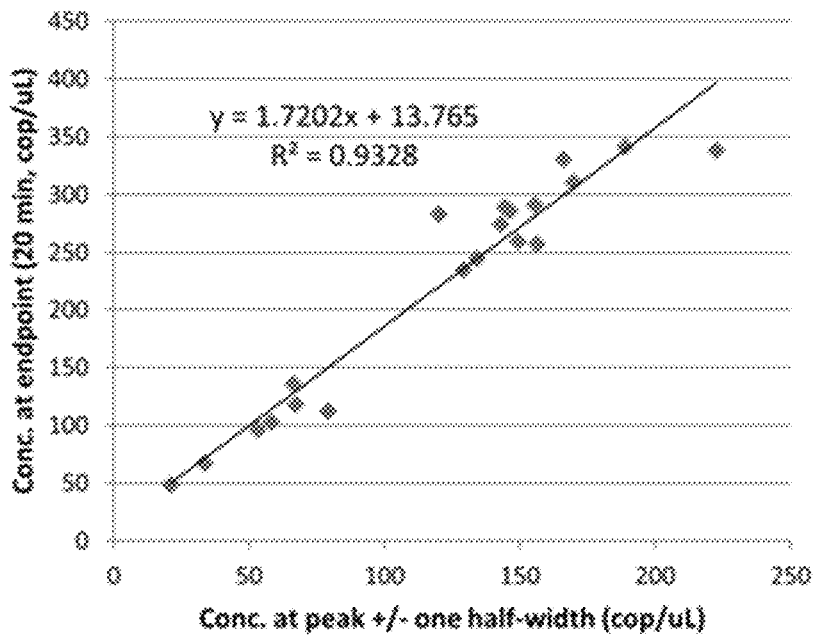
FIGS. 6A, 6B, 6C, 6D and 6E shows plots of correlation between the measured concentration of nucleic acids at different points along the TTP curve before the endpoint of the reaction.

In typical digital nucleic acid amplification reactions, compartments are not counted (and thus concentrations calculated) until the end of the reaction (~20-40 min for digital LAMP, ~40 cycles for digital PCR). In some embodiments of the method described herein, digital samples are imaged in real-time (every 20 seconds). Concentrations at incomplete reaction times can be calculated and used to predict the endpoint concentration. This decreases the necessary reaction time. Data from a set of 20 SlipChips was analyzed to generate a correlation of incomplete reaction times and endpoint (20 min) concentration using five different methods, described below. With a time-to-positive (TTP) distribution of a population of digital samples (FIG. 5, showing a TTP distribution and datapoints along the TTP curve used for endpoint detection (lines above graph extending from start to finish of TTP data used for each method)), the following methods can be used to predict the endpoint concentration:

The maximum of the TTP distribution was used as the midpoint of the distribution. The time elapsed from the first positive to the maximum is defined as a "half-width". The number of positive counts was determined by integrating+/− one half-width from the TTP maximum (FIG. 5 "Symmetric, Narrow"). With the number of positive counts, Poisson statistics were used to calculate concentrations (FIG. 6A).

Figure 6B:
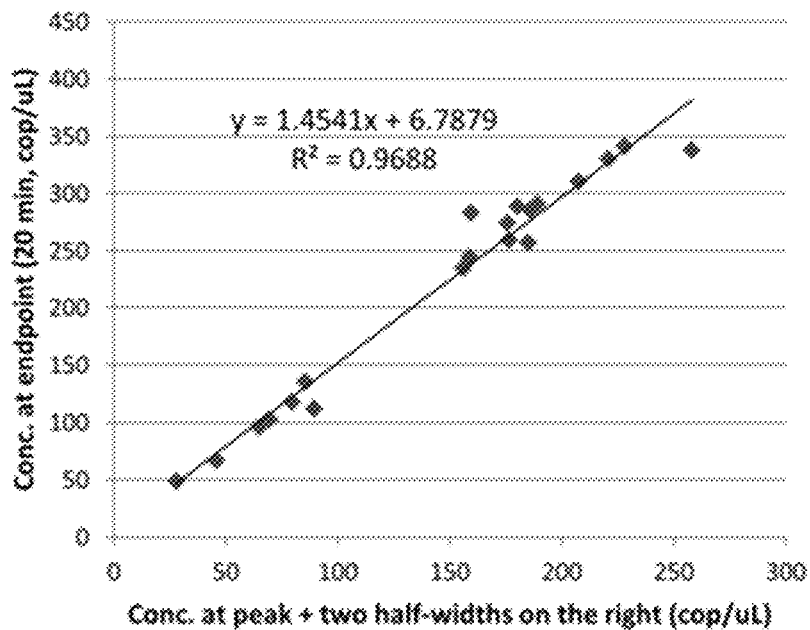

The maximum of the TTP distribution was used as the midpoint of the distribution. The time elapsed from the first positive to the maximum is defined as a "half-width". The number of positive counts was determined by integrating from the first positive count up to two half-widths after the TTP maximum (FIG. 5 "Asymmetric"). With the number of positive counts, Poisson statistics were used to calculate concentrations (FIG. 6B).

Figure 6C:
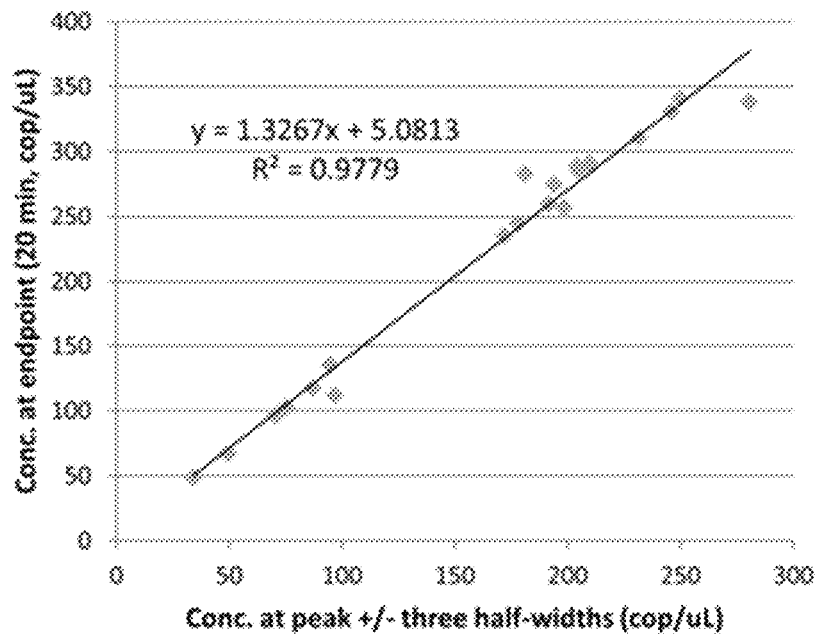

The maximum of the TTP distribution was used as the midpoint of the distribution. The time elapsed from the first positive to the maximum is defined as a "half-width". The number of positive counts was determined by integrating+/− three half-widths from the TTP maximum (FIG. 5, "Symmetric, Broad"). With the number of positive counts, Poisson statistics were used to calculate concentrations (FIG. 6C).

Figure 6D:
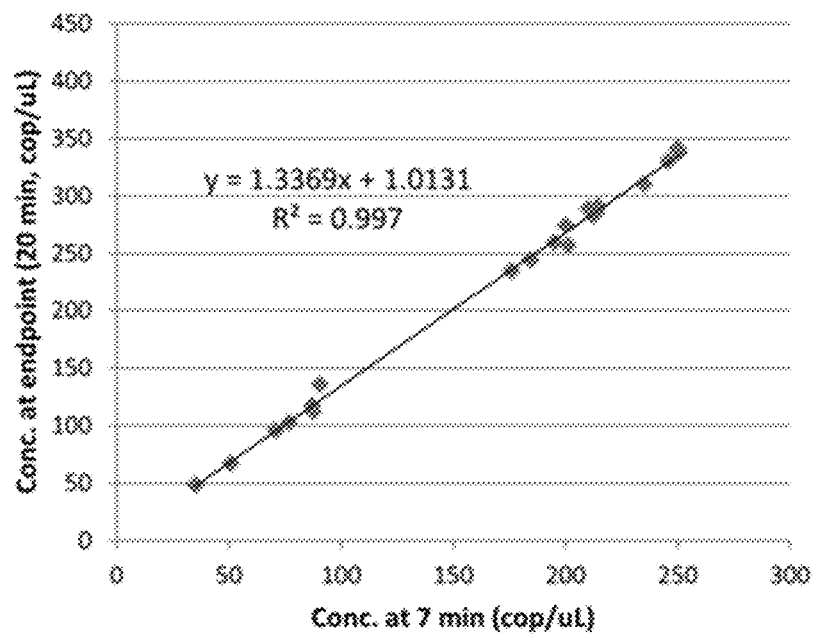

The number of positive counts was determined by integrating all counts from 0 to 7 min (FIG. 5, "7 Minutes"). With the number of positive counts, Poisson statistics were used to calculate concentrations (FIG. 6D). 7 minutes was chosen because, for this digital LAMP assay, >70% of compartments with a target molecule amplify in 7 min or less. For faster or slower digital nucleic acid amplification assays, different time breakpoints can be chosen to include >70% of positive compartments and accurately predict the true endpoint concentration.

Figure 6E:
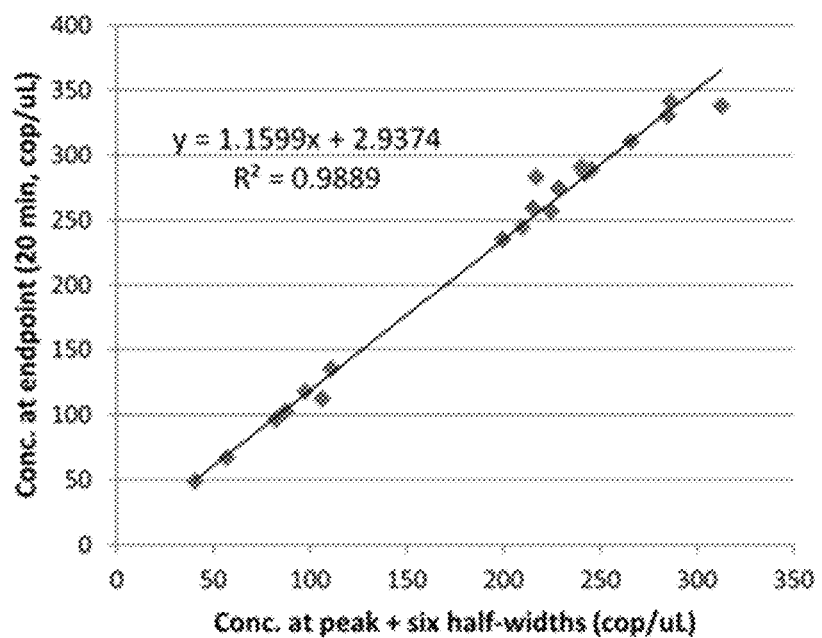

The maximum of the TTP distribution was used as the midpoint of the distribution. The time elapsed from the first positive to the maximum is defined as a "half-width". The number of positive counts was determined by integrating from the first positive count up to six half-widths after the TTP maximum (FIG. 6E). With the number of positive counts, Poisson statistics were used to calculate concentrations (FIG. 5, "Asymmetric, Broad").

In each of the above embodiments, the endpoint prediction (e.g., to determine a concentration of a target analyte such as an amplifiable target molecule) can be reliably achieved using TTP data around the peak TTP generation of a population of digital samples while the population of digital samples continues to generate positive signals from an amplification reaction, or significantly before the population of digital samples has reached an endpoint. Other methods of prediction of endpoint can also be used. For example, the half-width can be defined as the time elapsed from a minimum threshold number of positives (instead of 1) to the TTP maximum. The half-width can be defined as the time elapsed from a minimum number of positives equal to 25% of the TTP maximum to the TTP maximum. Symmetric and asymmetric distributions can be fitted to the TTP distribution and various numbers of half-widths can be used to integrate the cumulative number of positives at a given time point. In all the methods shown above and described here, endpoint digital nucleic acid concentrations can be predicted from incomplete reaction times.

Preliminary Quantification

Figure 2:
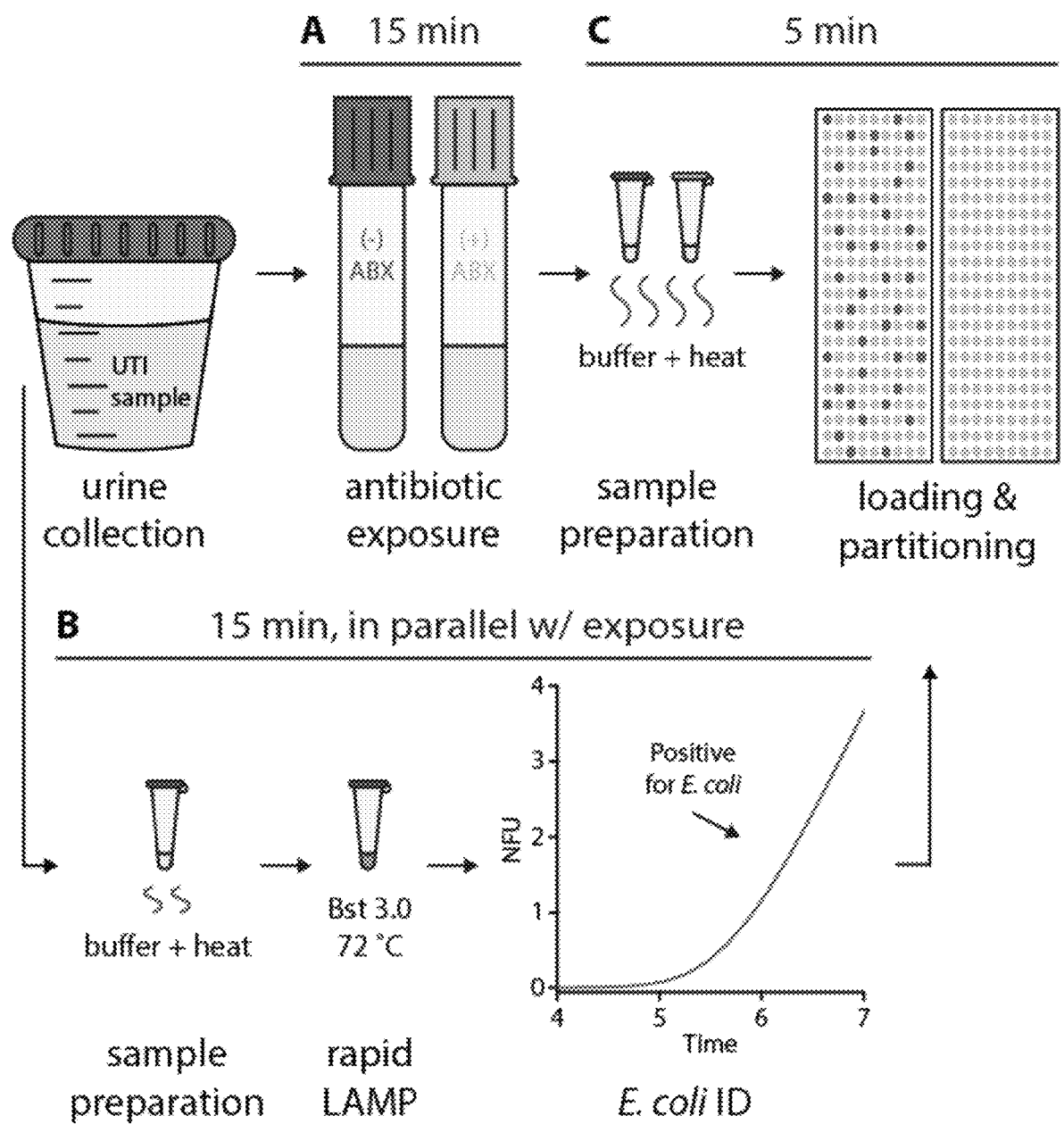
FIG. 2 shows a workflow of a sample-to-answer AST performed in less than 30 min, according to an embodiment of the invention. (A) A clinical UTI sample was added to media with and without ciprofloxacin (cip) and incubated for 15 min. (B) During the antibiotic-exposure step, the optimized bulk LAMP assay was performed on NAs prepared from an aliquot of the urine sample. Amplification indicated the presence of E. coli at clinically-relevant concentrations. (C) Aliquots of the control and antibiotic-treated samples were added to extraction buffer; nucleic acids (NAs) were prepared for quantification using dLAMP; and samples were rapidly partitioned using SlipChips.

Semi-quantification (also sometimes referred to as a "preliminary quantification") describes an estimate of the AST marker in a sample prior (or in parallel) to performing a quantification that is used to make a final AST determination. In some cases, the semi-quantification results can inform the method (e.g. necessary sample dilution) for determining the final quantification of AST markers for the final AST results. In some embodiments, real-time quantitative LAMP (qLAMP) for semi-quantification of AST markers is performed before and/or while samples are being exposed to an antibiotic in order to know how much to dilute for digital quantification In some embodiments, the AST is performed with the aid of quantitative or semi-quantitative analysis. A part of the sample (such as e.g. human clinical sample, contrived sample, animal sample, environmental sample) is used to quantify at least one AST marker or some other marker indicating the concentration of the AST markers of the pathogen in the sample (for example, a quantification marker could be bacterial DNA or RNA). FIG. 2 shows an example of an experimental workflow of the dAST method using preliminary quantification performed simultaneously with antibiotic exposure. Portions of urine samples are incubated without and with antibiotics (ABX) (part A). Simultaneously, a quantitative assay, such as a LAMP assay, are performed on other portions of the urine samples to determine a quantity of AST markers present in the urine sample (part B). This quantification is used to ensure that distribution of the sample into analysis regions generates digital samples such that some samples have a threshold level of AST markers sufficient to generate a detectable signal, and some do not. AST markers are distributed onto a plurality of analysis regions to generate a control (−ABX) population of digital samples and a treated (+ABX) population of digital samples (part C). AST markers are then quantified in the control (−ABX) and treated (+ABX) samples (part C). Control-treated (CT) ratios are analyzed. Antibiotic susceptibility is determined by measuring the quantity of a specific nucleic acid sequence (AST markers) in the control and treated samples to generate a CT ratio. In some embodiments, the different samples are loaded into their respective reaction areas simultaneously.

This quantification can be performed by a rapid real time method, for example such as real time LAMP, or a rapid digital method, such as dLAMP. This quantification is preferably specific to the pathogen or pathogens which are targets of AST.

In some embodiments, this quantification is performed prior to the exposure of the sample (by this we mean at least one part of the sample) to at least one antibiotic. Also, this quantification can be performed in conjunction with identification, using for example target-specific primers. For example, a pathogen identification step may be performed on one or more portions of the sample, followed or in parallel to exposing one or more portions of the sample to at least one antibiotic. In some embodiments, pathogen identification may be performed concurrently with exposing the sample to at least one antibiotic. In some embodiments, pathogen identification and pathogen semi-quantification (and/or AST marker quantification) may be performed simultaneously.

In some embodiment, pathogen quantification (and/or AST marker quantification) is used to guide the methodology used for quantifying at least one AST marker in a sample exposed to an antibiotic. For example, an initial quantification of one or more AST markers may be used to guide dilutions of the antibiotic-exposed sample in which one or more AST marker(s) would be further quantified. As another example, an initial quantification of one or more AST markers may be used to guide mixing ratio of the antibiotic-exposed sample in which one or more AST marker(s) would be further quantified with the quantification solution (e.g. amplification mix). As another example, an initial quantification of one or more AST markers may be used to guide the choice of the amplification device (e.g. a digital device and its dynamic range) used to quantify one or more AST marker(s) in the antibiotic-exposed sample.

Robustness

Robustness can be the degree to which a series of repeated quantitative measurements provides a set of similar measurements under varying experimental conditions. For example a cell phone camera can be used to successfully perform similar measurements on a SlipChip under a variety of conditions found in the real world. Similar measurements can be identical measurements. Similar measurements can be the same diagnosis. Similar measurements can be the same answer. Similar measurements can mean more than one measurement within experimental error of each other. Similar measurements can yield a consistent outcome with statistical significance. Similar measurements can be of similar numerical size, for instance within 5%, 10%, 15%, 20%, 25%, 30%, 40%, 50%, 60%, 70%, 80%, 90%, 100%, 200%, 1,000% of each other. Robust assays can produce similar measurements more often than 25%, 30%, 40%, 50%, 60%, 70%, 80%, 85%, 90%, 95%, 96%, 97%, 98%, 99%, 99.5%, 99.9%, 99.99%, for example, of instances measured under a given set of conditions.

Different types of assays can be robust assays. A nucleic acid amplification and quantification assay can be robust. An assay to detect a protein or other target such as a cell, exosome, liposome, bacteria, virus, etc. can be robust. A LAMP assay can be robust. A RT-LAMP assay can be robust. A dRT-LAMP assay can be robust. A binary LAMP reaction can be robust. A binary, two-step LAMP reaction can be robust. A PCR reaction can be robust. A qPCR assay can be robust. A quantitative nucleic acid amplification reaction can be robust. A qualitative nucleic acid amplification reaction can be robust. A method to diagnosis a health outcome based on the amplification of a nucleic acid sequence can be robust. A process within a SlipChip can be robust. The imaging and analysis of a SlipChip after a LAMP reaction can be a robust process.

The absolute efficiency of dRT-LAMP can be increased over 10-fold, e.g. from ~2% to ~28%, by i) using a more efficient reverse transcriptase, ii) introducing RNase H to break up the DNA-RNA hybrid, and iii) adding only the BIP primer during the RT step. dRT-LAMP can be compatible with a plastic SlipChip device and used this two-step method to quantify HIV RNA. The dRT-LAMP quantification results were in some cases very sensitive to the sequence of the patient's HIV RNA.

Assays can be robust with respect to experimental variables. An assay can be robust with respect to a given temperature range. An assay can be robust of over a temperature range. Some non-limiting ranges, over which an assay can be robust include 1° C., 2° C., 3° C., 4° C., 5° C., 6° C., 7° C., 8° C., 9° C., 10° C., 11° C., 12° C., 16° C., 20° C., 24° C., 28° C., 32° C., 40° C., 50° C., 60° C., 80° C., 100° C., 150° C., 200° C., 250° C., or 300° C., for example. The temperature range of which an assay is robust can be centered on temperature on an absolute temperature scale. Some non-limiting temperatures that could be the center of the temperature range that an assay is robust to include −40° C., −30° C., −20° C., −10° C., 0° C., 10° C., 20° C., room temperature, 25° C., 30° C., 35° C., body temperature, 37° C., 40° C., 45° C., 50° C., 55° C., 60° C., 65° C., 70° C., 80° C., 90° C., 100° C., 110° C., 150° C., or 200° C., for example. In some embodiments, a binary LAMP assay is used to amplify and subsequently image and quantify a nucleic acid sequence in a sample. In these embodiments, the assay can be a robust quantification of a nucleic acid sequence with over a temperature range of 9° C. centered at about 60° C. A binary LAMP assay used to amplify and subsequently image and quantify a nucleic acid sequence in a sample can be robust over the temperature range from about 55° C. to about 66° C. In some embodiments, a SlipChip can be imaged and the data can be processed to give robust findings over a range of a temperature from about 5° C. to about 70° C.

An assay can be robust with respect to time. An assay can give consistent results over a range of time points. An assay can give consistent results at a readout time before the end-point. A binary DNA amplification experiment can require only a readout before the end-point. A binary DNA amplification experiment can be observed in real time until a time at which consistent results can be obtained. The endpoint read out can be obtained at a time before the completion of the amplification reaction in the separate reaction volumes. A robust DNA amplification assay can give consistent results at a time point significantly before the end of the reaction. A non-limiting range of reaction time that an assay could be robust over includes times less than 4 min, 4.5 min 5 min, 5.5 min, 6 min, 6.5 min, 7 min, 7.5 min, 8 min, 9 min, 10 min, 12 min, 14 min, 16 min, 20 min, 24 min, 28 min, 32 min, 40 min, 45 min, 50 min, or 1.0 hour, for example. In some embodiments, a digital LAMP assay on a SlipChip is robust over a time period less than 6 minutes, less than 7 minutes, less than 8 minutes, less than 9 minutes, less than 10 minutes, or less than 15 minutes after the LAMP reaction begins, for example. In some embodiments, the assay is a comparative assay, such two or more binary DNA amplification experiments are performed, and the assay is robust with respect to the relative concentrations of a target analyte being amplified from two or more samples.

In some embodiments, a digital amplification assay of two or more samples provides a relative concentration by determining the relative rate of time to a positive signal in separate reaction volumes. In some embodiments, the assay provides a quantitative analytical measurement. For instance, the invention can measure and display the amount and/or the concentration of a nucleic acid sequence within a sample as a quantitative amount. This measurement can be robust with respect to the experimental conditions present during the chemical amplification of the nucleic acid sequence, during the measurement of the optical data, and/or during the processing of the data, for instance.

In some embodiments, small differences in the concentration of a target can be resolved with greater statistical significance by quantifying the response of two or more genes to antibiotic treatment. For example, in a scenario in which two genes experience a 1.2-fold change in concentration when comparing samples treated with a drug versus samples that are untreated. If quantification yields this 1.2-fold difference with a p-value of around 0.10, then the difference will not be statistically significant when analyzed independently. However, using Fisher's method to combine the results from several independent tests that have the same overall null hypothesis (that the treated and untreated bacterial nucleic acids are the same) will result in a lower p-value than each individual test. The test statistic used to combine the p-values from separate tests is $\chi^2$ and the formula is $$\chi^2_{2k} = -2\sum_{i=1}^{k} \ln(p_i)$$

For example, if two independent tests with p-values of 0.10 each are combined using this method, the overall p-value will now be 0.05, which is significant at the 95% confidence level. In some embodiments, digital NA (nucleic acid) quantification is more amenable to POC diagnostics In some embodiments, a ratio of the RNA from multiple genes is used to determine drug susceptibility. In some embodiments, this approach can include the use of housekeeping genes to measure relative changes in gene expression. In some embodiments, this includes the use of a ratio between genes upregulated and genes downregulated in response to drug treatment. In some embodiments, ratios of genes are used to enable higher sensitivity of quantification of responses when few cells are present in the sample, in some embodiments as few as 1 cells.

In some embodiments, the method involves the use of PrimerExplorer, LAMP Designer, or other primer design software packages to design multiple sets of primers against the same AST marker(s). These primer sets are then screened for specificity and speed using a temperature gradient to determine the maximum speed of each set and eliminate sets that show non-specific or off target amplification.

In some embodiments, this process involves optimization of isothermal (e.g., LAMP) conditions including detection dye (e.g., Syto-9) concentration, concentration of additives to reduce background, choice of polymerase (e.g. Bst-2 or Bst-3), and primer concentration Analysis It is to be understood that the exemplary methods and systems described herein can be implemented in various forms of hardware, software, firmware, special purpose processors, or a combination thereof. These instructions and programs can be executed by and/or stored on non-transitory computer readable media. Methods herein can be implemented in software as an application program tangibly embodied on one or more program storage devices. The application program can be executed by any machine, device, or platform comprising suitable architecture. It is to be further understood that, because some of the systems and methods described herein are implemented in software, the actual connections between the system components (or the process steps) can differ depending upon the manner in which the present invention is programmed.

The number or concentration of target analytes in a sample can be calculated based on the signal generated from the reaction volumes. The number, location, type, or a combination thereof of positive reaction volumes can be used to calculate the number or concentration of target analytes in a sample. The number, location, type, or a combination thereof of positive capture regions can be used to calculate the number or concentration of target analytes in a sample.

Assay results can be determined by comparison of results to theoretical models. For example, Poisson statistical analysis can be applied to quantify the number of fluorescent and non-fluorescent regions. Combining the results from wells of different volumes fully minimizes the standard error and provides high-quality analysis across a very large dynamic range.

The computer components, software modules, functions, data stores and data structures described herein can be connected directly or indirectly to each other in order to allow the flow of data needed for their operations. It is also noted that the meaning of the term module includes but is not limited to a unit of code that performs a software operation, and can be implemented for example as a sub-routine unit of code, or as a software function unit of code, or as an object (as in an object-oriented paradigm), or as an applet, or in a computer script language, or as another type of computer code. The software components and/or functionality can be located on a single computer or distributed across multiple computers depending upon the situation at hand. In yet another aspect, a computer readable medium is provided including computer readable instructions, wherein the computer readable instructions instruct a processor to execute the methods described herein. The instructions can operate in a software runtime environment. In yet another aspect, a data signal is provided that can be transmitted using a network, wherein the data signal includes data calculated in a step of the methods described herein. The data signal can further include packetized data that is transmitted through wired or wireless networks. In an aspect, a computer readable medium comprises computer readable instructions, wherein the instructions when executed carry out a calculation of the probability of a medical condition in a patient based upon data obtained from the sample. The computer readable instructions can operate in a software runtime environment of the processor. In some embodiments, a software runtime environment provides commonly used functions and facilities required by the software package. Examples of a software runtime environment include, but are not limited to, computer operating systems, virtual machines or distributed operating systems although several other examples of runtime environment exist. The computer readable instructions can be packaged and marketed as a software product, app, or part of a software package. For example, the instructions can be packaged with an assay kit. The computer readable medium can be a storage unit. Computer readable medium can also be any available media that can be accessed by a server, a processor, or a computer. The computer readable medium can be incorporated as part of the computer-based system, and can be employed for a computer-based assessment of a medical condition.

In some embodiment, the calculations described herein can be carried out on a computer system. The computer system can comprise any or all of the following: a processor, a storage unit, software, firmware, a network communication device, a display, a data input, and a data output. A computer system can be a server. A server can be a central server that communicates over a network to a plurality of input devices and/or a plurality of output devices. A server can comprise at least one storage unit, such as a hard drive or any other device for storing information to be accessed by a processor or external device, wherein the storage unit can comprise one or more databases. In an embodiment, a database can store hundreds to millions of data points corresponding to a data from hundreds to millions of samples. A storage unit can also store historical data read from an external database or as input by a user. In an embodiment, a storage unit stores data received from an input device that is communicating or has communicated with the server. A storage unit can comprise a plurality of databases. In an embodiment, each of a plurality of databases corresponds to each of a plurality of samples. An individual database can also comprise information for a plurality of possible sample containment units. Further, a computer system can comprise multiple servers. A processor can access data from a storage unit or from an input device to perform a calculation of an output from the data. A processor can execute software or computer readable instructions as provided by a user, or provided by the computer system or server. The processor can have a means for receiving patient data directly from an input device, a means of storing the subject data in a storage unit, and a means for processing data. The processor can also include a means for receiving instructions from a user or a user interface. The processor can have memory, such as random access memory. In one embodiment, an output that is in communication with the processor is provided. After performing a calculation, a processor can provide the output, such as from a calculation, back to, for example, the input device or storage unit, to another storage unit of the same or different computer system, or to an output device. Output from the processor can be displayed by data display. A data display can be a display screen (for example, a monitor or a screen on a digital device), a print-out, a data signal (for example, a packet), an alarm (for example, a flashing light or a sound), a graphical user interface (for example, a webpage), or a combination of any of the above. In an embodiment, an output is transmitted over a network (for example, a wireless network) to an output device. The output device can be used by a user to receive the output from the data-processing computer system. After an output has been received by a user, the user can determine a course of action, or can carry out a course of action, such as a medical treatment when the user is medical personnel. In some embodiments, an output device is the same device as the input device. Example output devices include, but are not limited to, a telephone, a wireless telephone, a mobile phone, a PDA, a flash memory drive, a light source, a sound generator, a computer, a computer monitor, a printer, and a webpage. The user station can be in communication with a printer or a display monitor to output the information processed by the server.

A client-server, relational database architecture can be used in embodiments of the invention. A client server architecture is a network architecture in which each computer or process on the network is either a client or a server. Server computers are typically powerful computers dedicated to managing disk drives (file servers), printers (print servers), or network traffic (network servers). Client computers include PCs (personal computers), cell phones, or workstations on which users run applications, as well as example output devices as disclosed herein. Client computers rely on server computers for resources, such as files, devices, and even processing power. In some embodiments of the invention, the server computer handles all of the database functionality. The client computer can have software that handles all the front-end data management and can also receive data input from users.

Subject data can be stored with a unique identifier for recognition by a processor or a user. In another step, the processor or user can conduct a search of stored data by selecting at least one criterion for particular patient data. The particular patient data can then be retrieved. Processors in the computer systems can perform calculations comparing the input data to historical data from databases available to the computer systems. The computer systems can then store the output from the calculations in a database and/or communicate the output over a network to an output device, such as a webpage, a text, or an email. After a user has received an output from the computer system, the user can take a course of medical action according to the output. For example, if the user is a physician and the output is a probability of cancer above a threshold value, the physician can then perform or order a biopsy of the suspected tissue. A set of users can use a web browser to enter data from a biomarker assay into a graphical user interface of a webpage. The webpage is a graphical user interface associated with a front end server, wherein the front end server can communicate with the user's input device (for example, a computer) and a back end server. The front end server can either comprise or be in communication with a storage device that has a front-end database capable of storing any type of data, for example user account information, user input, and reports to be output to a user. Data from each user can be then be sent to a back end server capable of manipulating the data to generate a result. For example, the back end server can calculate a corrections for similar cell phones or compile data generated from similar sample collection units. The back end server can then send the result of the manipulation or calculation back to the front end server where it can be stored in a database or can be used to generate a report. The results can be transmitted from the front end server to an output device (for example, a computer with a web browser or a cell phone) to be delivered to a user. A different user can input the data and receive the data. In an embodiment, results are delivered in a report. In another embodiment, results are delivered directly to an output device that can alert a user.

The information from the assay can be quantitative and sent to a computer system of the invention. The information can also be qualitative, such as observing patterns or fluorescence, which can be translated into a quantitative measure by a user or automatically by a reader or computer system. In an embodiment, the subject can also provide information other than sample assay information to a computer system, such as race, height, weight, age, gender, eye color, hair color, family medical history, identity, location and any other information that can be useful to the user.

In some embodiments additional information is provided by sensors associated with the device. For example global positioning data, acceleration data, air pressure, or moisture levels can be measured by a device comprising the image sensor. This additional information can be used by the computer systems of the invention.

Information can be sent to a computer system automatically by a device that reads or provides the data from image sensor. In another embodiment, information is entered by a user (for example, the subject or medical professional) into a computer system using an input device. The input device can be a personal computer, a mobile phone or other wireless device, or can be the graphical user interface of a webpage. For example, a webpage programmed in JAVA can comprise different input boxes to which text can be added by a user, wherein the string input by the user is then sent to a computer system for processing. The subject can input data in a variety of ways, or using a variety of devices. Data can be automatically obtained and input into a computer from another computer or data entry system. Another method of inputting data to a database is using an input device such as a keyboard, touch screen, trackball, or a mouse for directly entering data into a database.

In an embodiment, a computer system comprises a storage unit, a processor, and a network communication unit. For example, the computer system can be a personal computer, laptop computer, or a plurality of computers. The computer system can also be a server or a plurality of servers. Computer readable instructions, such as software or firmware, can be stored on a storage unit of the computer system. A storage unit can also comprise at least one database for storing and organizing information received and generated by the computer system. In an embodiment, a database comprises historical data, wherein the historical data can be automatically populated from another database or entered by a user.

In an embodiment, a processor of the computer system accesses at least one of the databases or receives information directly from an input device as a source of information to be processed. The processor can perform a calculation on the information source, for example, performing dynamic screening or a probability calculation method. After the calculation the processor can transmit the results to a database or directly to an output device. A database for receiving results can be the same as the input database or the historical database. An output device can communicate over a network with a computer system of the invention. The output device can be any device capable delivering processed results to a user.

Communication between devices or computer systems of the invention can be any method of digital communication including, for example, over the internet. Network communication can be wireless, ethernet-based, fiber optic, or through fire-wire, USB, or any other connection capable of communication. In an embodiment, information transmitted by a system or method of the invention can be encrypted.

It is further noted that the systems and methods can include data signals conveyed via networks (for example, local area network, wide area network, internet), fiber optic medium, carrier waves, wireless networks for communication with one or more data processing or storage devices. The data signals can carry any or all of the data disclosed herein that is provided to or from a device.

Additionally, the methods and systems described herein can be implemented on many different types of processing devices by program code comprising program instructions that are executable by the device processing subsystem. The software program instructions can include source code, object code, machine code, or any other stored data that is operable to cause a processing system to perform methods described herein. Other implementations can also be used, however, such as firmware or even appropriately designed hardware configured to carry out the methods and systems described herein.

A computer system can be physically separate from the instrument used to obtain values from the subject. In an embodiment, a graphical user interface also can be remote from the computer system, for example, part of a wireless device in communication with the network. In another embodiment, the computer and the instrument are the same device.

An output device or input device of a computer system can include one or more user devices comprising a graphical user interface comprising interface elements such as buttons, pull down menus, scroll bars, fields for entering text, and the like as are routinely found in graphical user interfaces known in the art. Requests entered on a user interface are transmitted to an application program in the system (such as a Web application). In one embodiment, a user of user device in the system is able to directly access data using an HTML interface provided by Web browsers and Web server of the system.

A graphical user interface can be generated by a graphical user interface code as part of die operating system or server and can be used to input data and/or to display input data. The result of processed data can be displayed in the interface or a different interface, printed on a printer in communication with the system, saved in a memory device, and/or transmitted over a network. A user interface can refer to graphical, textual, or auditory information presented to a user and can also refer to the control sequences used for controlling a program or device, such as keystrokes, movements, or selections. In another example, a user interface can be a touch screen, monitor, keyboard, mouse, or any other item that allows a user to interact with a system of the invention.

Use of Antibiotic Susceptibility Data

In yet another aspect, a method of taking a course of medical action by a user is provided including initiating a course of medical action based on sample analysis. The course of medical action can be delivering medical treatment to said subject. The medical treatment can be selected from a group consisting of the following: a pharmaceutical, surgery, organ resection, and radiation therapy. The pharmaceutical can include, for example, an antibiotic for a microorganism shown to be susceptible to the antibiotic through AST testing described herein. The course of medical action can include, for example, administration of medical tests, medical imaging of said subject, setting a specific time for delivering medical treatment, a biopsy, and a consultation with a medical professional. The course of medical action can include, for example, repeating a method described above. A method can further include diagnosing the medical condition of the subject by said user with said sample. A system or method can involve delivering a medical treatment or initiating a course of medical action. If a disease has been assessed or diagnosed by a method or system of the invention, a medical professional can evaluate the assessment or diagnosis and deliver a medical treatment according to his evaluation. Medical treatments can be any method or product meant to treat a disease or symptoms of the disease. In an embodiment, a system or method initiates a course of medical action. A course of medical action is often determined by a medical professional evaluating the results from a processor of a computer system of the invention. For example, a medical professional can receive output information that informs him that a subject has a 97% probability of having a particular medical condition, such as an antibiotic susceptibility or resistance. Based on this probability, the medical professional can choose the most appropriate course of medical action, such as type of antibiotic treatment, biopsy, surgery, medical treatment, or no action. In an embodiment, a computer system of the invention can store a plurality of examples of courses of medical action in a database, wherein processed results can trigger the delivery of one or a plurality of the example courses of action to be output to a user.

In an embodiment, a computer system outputs information and an example course of medical action, such as an appropriate antibiotic to use for treatment. In another embodiment, the computer system can initiate an appropriate course of medical action. For example, based on the processed results, the computer system can communicate to a device that can deliver a pharmaceutical to a subject. In another example, the computer system can contact emergency personnel or a medical professional based on the results of the processing. Courses of medical action a patient can take include self-administering a drug, applying an ointment, removing a dressing, or scheduling an appointment and/or visiting a medical professional. A medical professional can be for example a physician, emergency medical personnel, a pharmacist, psychiatrist, psychologist, chiropractor, acupuncturist, dermatologist, urologist, proctologist, podiatrist, oncologist, gynecologist, neurologist, pathologist, pediatrician, radiologist, a dentist, endocrinologist, gastroenterologist, hematologist, nephrologist, ophthalmologist, physical therapist, nutritionist, physical therapist, or a surgeon.

Platforms/Devices

Provided herein are devices (e.g., microfluidic devices) and methods that can rapidly identify a cell, including a cancer cell, or microorganism, including a pathogen, quantify their load, and diagnose their susceptibility or resistance to drugs, such as antibiotics. In some embodiments the devices can enable phenotypic detection and metabolic profiling of drug susceptibility or drug resistance using individual microorganisms or cells which can originate from various sample types, including clinical or environmental samples. These sample types can include, but are not limited to, blood, cerebral spinal fluid (CSF), saliva and urine and can also include environmental samples, such as from water or a hospital surface. In some embodiments, the devices enable incubation of cells with drugs, such as antibiotics, and then rapidly extract and quantify nucleic acids or other molecules in a contamination-free platform. The devices can use digital single-molecule measurements in microfluidics devices, which provide ultra-sensitive measurements that improve detection limits while providing quantitative data, important for differentiating pathogens from contaminants and enabling earlier differentiation between drug-resistant and susceptible microorganisms or cells. In some embodiments, these devices can differentiate the state of individual microorganisms or cells from a clinical sample, and understand the timing of their individual responses to drugs, such as for example antibiotics, providing ultra-fast drug-susceptibility measurements.

In some embodiments the devices and methods can be used in assessing gene duplications measurements for each given cells, as in response to antibiotic stress some microbes can replicate antibiotic resistant genes (like lactamases) to 100s of copies, allowing them to undergo evolution.

In some embodiments, the devices and methods allow identification of drug-resistant bacteria from a pool of bacteria, such as a clinical sample, that can include drug-susceptible bacteria and/or drug-resistant bacteria and/or contamination with pathogenic and/or nonpathogenic bacteria—or some combination of these types. In some embodiments the devices can be used to incubate cells with drugs and then rapidly extract and quantify nucleic acids, such as for example RNA, in a contamination-free platform to determine drug susceptibility. In some embodiments, the methods and devices provided herein enable microbial and cell identification and drug susceptibility testing outside of CLIA clinical laboratories Devices can comprise channels and flowpaths, such as microfluidic channels. Devices can comprise inlets, outlets, or any combination thereof. Devices can comprise wells, reservoirs, or any combination thereof. Devices can comprise reaction volumes. Devices can comprise pre-loaded reagents. In some cases, the microfluidic device comprises a SlipChip device, as described for example in U.S. Pat. Nos. 9,415,392, 9,464,319, and 9,447,461, and in International Patent Publication No. WO/2010/111265 and WO/2013/072069 A1, each of which is hereby incorporated by reference in its entirety. In some embodiments, the samples are contacted with a reagent for performing a reaction.

Platforms can comprise fluid handling mechanisms enabling loading, unloading, mixing, and other handling of sample volumes, reagent volumes, and other fluids. For example, a microfluidic device can be used comprising channels for loading fluids into wells or droplets, for mixing contents of wells or droplets, or for off-loading of contents of wells or droplets.

Some platforms are useful for conducting assays in a digital or quasi-digital format, as described herein. For example, wells, well plates, microwells, microfluidic droplets, emulsions, beads, and microarrays can provide a useful platform for conducting a digital or quasi-digital assay. In such an assay, the compartments can comprise individual wells, droplets, beads, or microarray spots.

In some embodiments, devices described herein incorporate SlipChip digital amplification technology and SlipChip sample preparation technology (Shen, et al., 2010, Analytical Chemistry, 4606-4612, Shen, et al., 2010, Lab on a Chip, 2666-2672, Shen, et al., 2011, Analytical Chemistry, 3533-3540, Shen, et al., 2011, J Am Chem Soc, 17705-17712) and can perform rapid single-molecule identification, and quantification of nucleic acids from cells and microorganisms, such as for example *Klebsiella pneumonia*, *Pseudomonas aeruginosa*, and extra-intestinal pathogenic *E. coli*. Samples can be obtained from a variety of human bodily fluids, such as for example blood, plasma, saliva, CSF or urine, or a variety of environmental samples, such as for example water or hospital surfaces. In some embodiments, this can enable clinical validation of workflow that in some embodiments provides a differential diagnosis of an infection, such as for example a UTI. In some embodiments, this device can provide quantification of total cell load and species and/or strain identification. In some embodiments, the results of the assay can be available in less than 45 minutes, less than 30 minutes, less than 20 minutes, less than 10 minutes, less than 5 minutes, less than 3 minutes, or less than 1 minute.

In some embodiments, the technology described here enables identification and quantification of nucleic acids, such as for example bacterial DNA and RNA extracted from urine samples spiked with a cell culture of reference strains. Reference strains are those are used routinely in clinical labs as part of their quality control protocol, such as for example *K. pneumoniae* (ATCC 700603), *P. aeruginosa* (ATCC 27853), and *E. coli* (ATCC 25922).(Institute., 2012, M07-A09) In some embodiments the technology and devices described in this disclosure can be integrated with standard bench methods and kits (Qiagen Qiamp DNA kit) to extract nucleic acids, and previously published universal primers can be used to target genes, such as for example the conserved region of the 16S gene, in order to quantify nucleic acid concentration (Clifford, et al., 2012, PLoS ONE, e48558, Nadkarni, et al., 2002, Microbiology, 257-266). For example, the technology can be used to target hyper-variable regions of the 16S gene to quantify and identify microorganisms (Baker, et al., 2003, Journal of Microbiological Methods, 541-555, Hansen, et al., 2013, PLoS ONE, e61439, Spilker, et al., 2004, Journal of Clinical Microbiology, 2074-2079).

In some embodiments, the devices described herein allow identification of drug-resistant bacteria from a pool of bacteria, such as a clinical sample, that can include drug-susceptible bacteria and/or drug-resistant bacteria and/or contamination with pathogenic and/or nonpathogenic bacteria, or any combination thereof.

In some embodiments, the technology can be used for bacterial DNA and RNA amplification assays using the digital SlipChip over a dynamic range of, for example, 1,000 to $1 \times 10^7$ copies/mL with, for example, three-fold resolution and a 95% confidence interval. This dynamic range is well covered by the digital SlipChip that is commercially manufactured, which contains 10,240 of 0.84 nL wells with a dynamic range of 450 to $9.7 \times 10^7$ copies/mL and a detection limit of 120 copies/mL.

A workflow of determining the resistance or susceptibility of a cell in a sample of urine to a drug according to an embodiment of the invention is shown in FIG. 2. In some embodiments, the device enables assays that perform both sample prep (e.g., exposure of microorganisms in the sample to a drug and extraction of target nucleic acids from the sample) and digital amplification (e.g., distributing and amplifying target nucleic acids to quantify the target nucleic acids present in the sample to determine a susceptibility or resistance of the microorganism to the drug).

Integrated Devices

In some embodiments, the devices provided herein are integrated devices comprising one or more modules. These modules include, but are not limited to, an incubation module, a sample preparation module, an amplification module, and a readout module. Modules and examples of, and uses of integrated devices are described in International Patent Publication No. WO/2015/085632, "Microfluidic Measurements of the Responses of an Organism to a Drug," incorporated by reference herein. In some embodiments, the integrated device combines two or more modules to provide a simplified processing flow for detecting the properties of a microorganism in response to a drug.

Kits

A kit can include a SlipChip device, and a supply of a reagent selected to participate in nucleic acid amplification. In some embodiments, the reagent can be disposed in a container adapted to engage with a conduit of the first component, the conduit of the second component, or both. Such a container can be a pipette, a syringe, and the like. In some embodiments, the kit includes a heater.

Some embodiments of the device could be used to detect different biological targets such as, for example, proteins, bacteria, viruses, infectious agents, etc., using nucleic acid labels. In some embodiments the target is tagged with an oligonucleotide which can be used for detection. The oligonucleotide tag can be further amplified using any one of a number of different nucleic acid amplification strategies, such as for example, PCR, LAMP, RPA, NASBA, RCA, etc. The oligonucleotide tag could also be visualized using fluorescent probes for example as shown by Chen (Huang, Suxian, and Yong Chen, "Polymeric Sequence Probe for Single DNA Detection." Analytical chemistry 83.19 (2011): 7250-7254.)

EQUIVALENTS AND SCOPE

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

Section and table headings are not intended to be limiting.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, Proteins: Structures and Molecular Properties (W.H. Freeman and Company, 1993); A. L. Lehninger, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.); Remington's Pharmaceutical Sciences, 18th Edition (Easton, Pa.: Mack Publishing Company, 1990); Carey and Sundberg Advanced Organic Chemistry 3rd Ed. (Plenum Press) Vols A and B(1992).

Example 1: Formation of a SlipChip

The procedure for fabricating glass SlipChips for digital LAMP (dLAMP) was based on previous work (see, e.g., B. Sun, J. Rodriguez-Manzano, D. A. Selck, E. Khorosheva, M. A. Karymov, R. F. Ismagilov. Measuring fate and rate of single-molecule competition of amplification and restriction digestion, and its use for rapid genotyping tested with hepatitis C viral RNA. *Angew. Chem. Int. Ed. Engl.* 53, 8088-8092 (2014)). The dLAMP devices were fabricated using a one-step exposing-etching protocol that created wells with a depth of 55 μm. The device contained a total of 1,280 wells (each with a volume of 3 nL). After etching, devices were subjected to the same glass silanization process, where the glass plates were first thoroughly cleaned with piranha mix and dried with 200 proof ethanol and nitrogen gas, and then oxidized in a plasma cleaner for 3 minutes and immediately transferred into a vacuum desiccator for 1.5 hours for silanization with dimethyldichlorosilane. After silanization, the devices were rinsed thoroughly with chloroform, acetone, and ethanol, and dried with nitrogen gas before use. When a glass SlipChip needed to be reused, it was cleaned with Piranha acid first, and then subjected to the same silanization and rinsing procedure described above.

The glass SlipChips for the dLAMP were assembled under degassed oil (mineral oil: tetradecane 1:4 v/v). Both top and bottom plates were immersed into the oil phase and placed face to face. The two plates were aligned under a stereoscope (Leica, Germany) and fixed using binder clips. Through-holes were drilled into the top plate to serve as fluid inlets and oil outlets in dead-end filling. The reagent solutions were loaded through the inlets by pipetting. Glass SlipChips were used for the examples described herein, unless otherwise noted.

Injection-molded SlipChips were used for Example 14 to run clinical samples 28-29 and 48-51 with the rapid dLAMP assay, with the rest being done in glass SlipChips. These disposable injection molded SlipChips contained 5,376 2.4-nL compartments, which enable shorter turnaround times between experiments.

Example 2: Antibiotic Exposure to Clinical Samples and DNA Extraction

Unless otherwise specified, before the start of each experiment on urine samples in the examples described herein, urine as received, was warmed to 37° C. over 30 min to mimic the temperature of fresh urine samples. At the start of each dAST experiment (t=0), warmed urine was added to media (pre-warmed to 37° C.) with or without antibiotics (±ABX) to initiate DNA replication and begin exposure. This addition to media dilutes the boric acid in the transport media, allowing bacterial replication to proceed. The final 500 μL sample mixture in the control and treated tubes contained 250 μL brain heart infusion media (Becton Dickinson), 25 μL DNase I (New England Biolabs,), 5 μL DNase buffer (100 mM Tris-HCl, 25 mM $MgCl_2$, and 5 mM $CaCl_2$), an aliquot of the urine, with the remaining volume NF—$H_2O$. Either 1 μg/mL cip or 16 μg/mL nit was added to the +ABX sample, with an equal volume of NF—$H_2O$ (in the case of cip) or dimethylformamide (in the case of nit) added to the control sample (−ABX). ABX concentrations were chosen based on previous work with isolates (Schoepp et al., *Angew. Chem. Int. Ed. Engl.* 55, 9557-9561 (2016)) and are near the Clinical & Laboratory Standards Institute (CLSI) and European Committee on Antimicrobial Susceptibility Testing (EUCAST) breakpoints. A 10 μL aliquot of urine was added to control and treated tubes in the cip treatments; a 25 μL aliquot was added in the nit treatments. Samples were shaken at 750 rpm at 37° C. for 30 min. After a preset time of exposure (e.g., 0, 15, and 30 min), 10 μL aliquots of the control and treated samples were removed and added to 90 μL of QuickExtract DNA Extraction Solution. The extracted samples were heated according to a modified version of the manufacturer's protocol (65° C. for 6 min, 95° C. for 4 min, chilled on ice), vortexed, and centrifuged. Next, 5 μL of each extraction was added to amplification reagents for quantification.

Example 3: DNA Quantification (qPCR and dPCR)

Unless, otherwise specified, all qPCR reactions were performed using a Roche LightCycler 96. All reactions contained only SsoFast EvaGreen Supermix at a final concentration of 1×, forward and reverse primers (forward primer TGCCGTAACTTCGGGAGAAGGC (SEQ ID NO: 1), reverse primer TCAAGGCTCAATGTTCAGTGTC (SEQ ID NO: 2)) specific for Enterobacteriaceae at a final concentration of 500 nM, template DNA at variable concentrations, and NF—$H_2O$. A single master mix containing supermix, primers, and NF—$H_2O$ was prepared and aliquoted into PCR tubes. Template was then added, bringing the final volume to 30 μL. Each tube was then mixed thoroughly via pipette and technical triplicates (9 μL each) were aliquoted into the 96 well plate. Cycling conditions consisted of an initial denaturation step at 95° C. for 3 min. followed by 30 cycles of 95° C. for 20 s, 62° C. for 20 s, and 72° C. for 20 s. Following amplification a continuous melt curve was obtained between 55 and 95° C. Total cycling time (including melt analysis) was 60 min.

Unless otherwise specified, digital PCR reactions were carried out in a BioRad QX200 Droplet Digital PCR system according to the manufacturer's instructions. Samples were prepared in identical fashion as those prepared for qPCR. For each sample, two wells of the droplet generation chip and well plate were used to generate and thermocycle droplets, respectively. Cycling conditions consisted of an initial denaturation step at 95° C. for 5 min followed by 40 cycles of 95° C. for 30 s, 60° C. for 30 s, and 72° C. for 30 s. Following initial thermocycling, the sample was cooled to 4° C. for 5 min followed by a final heating step at 95° C. for 5 min. All thermocycling steps were performed with a 2° C./s ramp rate. Total cycling time was 115 minutes.

Example 4: Digital PCR in a SlipChip

Unless otherwise noted, digital PCR was performed on a SlipChip according to the protocols described in Shen et al., "Digital PCR on a SlipChip," Lab Chip 2010 10: 2666-2672.

Briefly, in this published method, top and bottom SlipChip plates were etched with microfluidic channels and wells via photolithography and HF etching. The top and bottom plates were aligned in a mixture of 20% mineral oil/80% tetradecane and then clamped to hold in place. DNA from the extractions described above was added to PCR master mix. This solution was loaded into the SlipChip device with a pipette. After loading, a slip broke the channels into 1280 individual 3 nL compartments. Next, the SlipChip was clamped, sealed, and placed on a thermocycler for the following temperatures: 92° C. for 3 minutes, 40 cycles of: 92° C. for 20 seconds, 62° C. for 20 seconds, and 72° C. for 25 seconds. The SlipChip was imaged, positive and negative wells were counted, and the concentration of target DNA was calculated using Poisson statistics.

Example 5: Digital LAMP in a SlipChip

Unless otherwise noted, digital LAMP Amplification on a SlipChip was performed as follows: Two reagent solutions were loaded into two separate SlipChips. The first solution, which had a nucleic acid extraction from bacteria exposed to an antibiotic for 15 minutes, contained the following: 1 μL 10× IsoAmp buffer II, 0.2 μL 50 mg/mL BSA, 0.3 μL 100 mM $MgSO_4$, 0.4 μL BST 3.0 DNA polymerase (8000 U/mL), 0.5 μL 20×23S LAMP primer mix, 1.4 μL 10 mM dNTPs, 0.5 μL 40 μM Syto-9 dye, 4.7 μL nuclease-free water, and 1 μL nucleic acid extraction from the sample treated with antibiotic. The second solution, which had a nucleic acid extraction from bacteria without exposure to an antibiotic for 15 minutes, contained the following: 1 μL 10× IsoAmp buffer II, 0.2 μL 50 mg/mL BSA, 0.3 μL 100 mM $MgSO_4$, 0.4 μL BST 3.0 DNA polymerase (8000 U/mL), 0.5 μL 20×23S LAMP primer mix, 1.4 μL 10 mM dNTPs, 0.5 μL 40 μM Syto-9 dye, 4.7 μL nuclease-free water, and 1 μL nucleic acid extraction from the sample that was not treated with antibiotic.

The top piece of each SlipChip was moved relative to the bottom piece, which partitioned the solution into 1,280 3-nL compartments (lab made glass SlipChips) or 5,376 2.4-nL compartments (injection-molded plastic SlipChips) (injection-molded used in Example 14). When using the injection-molded plastic SlipChips, the treated chip was loaded 30 s after the control chip. The SlipChips were then placed onto the thermal cycler of a digital real-time imaging instrument and incubated at 72° C. for 20 min. Amplification time was recorded starting from when the thermal cycler reached 72° C.

Experiments were performed on a Bio-Rad PTC-200 thermocycler with a custom machined block. The block contains a flat 3"×3" portion onto which the devices are placed ensuring optimal thermal contact. The excitation light source used was a Philips Luxeon S (LXS8-PW30) 1315 lumen LED module with a Semrock filter (FF02-475). Image Acquisition was performed with a VX-29MG camera and a Zeiss Macro Planar T F2-100 mm lens. A Semrock filter (FF01-540) was used as an emission filter.

Images were taken every 20 s and the fluorescent intensity was measured for each compartment. Images acquired were analyzed using Labview software as described in Selck et al., *PLoS One* 11, e0163060 (2016). The data were analyzed by first creating a binary mask that defined the location of each reaction volume within the image. The masked spots were then overlaid on the stack of images collected over the course of the experiment and the average intensity of each individual masked spot was tracked over the course of the stack. Background subtraction of the real-time trace was performed by creating a least mean square fit of each individual trace. Threshold was then manually set at the half height of the averaged maximum intensity, and the time-to-positive of each reaction was then determined as the point at which the real-time curve crossed the defined threshold Example 6: Statistical Analyses of qPCR and dPCR Raw Ct values are not normally distributed; therefore, a typical plot showing the mean Ct+/−2·SD does not mean that the true mean will lie in the confidence interval 95% of the time. Understanding this fact, we would still like to represent the variability in qPCR measurements for the raw Ct plot. We did this with a standard confidence interval calculation:

$$Ct_{U/L} = Ct_{avg} \pm t_{crit} \cdot \frac{s_{Cq}}{\sqrt{n}}$$

The critical t value (t_crit) for a 98% confidence interval with 2 degrees of freedom is 4.85; with n=3 replicates, this results in the SD being multiplied by 2.80 for the confidence intervals. This does not mean that the true Ct is within this interval 98% of the time, but it does give a representation of the variability in Ct measurements.

In order to calculate the p-value for comparing treated and untreated samples, the raw Ct values (which are exponential) were linearized into a relative quantity (FC) with t=0 min as the reference point using 〖FC=2〗^(Ct(t)−Ct(0)). The log ratio of these linearized quantities was compared to ln(1.1) using a one-tailed t test. A one-tailed test was chosen because the untreated sample should have a higher concentration than the treated sample; if by some random event the treated sample has a statistically significant higher concentration than untreated, we don't want to draw the false conclusion that the isolate is susceptible. To account for pipetting variation (the treated sample could have randomly had 10% more bacteria pipetted into its media at time=0 than the untreated sample), the null hypothesis is ln((FC_ut)/(FC_t))−ln(1.1)=0 instead of ln((FC_ut)/(FC_t))=0. This makes the AST more conservative (reducing very major errors) by requiring that the untreated sample have at least 1.1 fold more copies than the treated sample.

P-values for digital PCR were calculated with a one-tailed Z test comparing ln((FC_ut)/(FC_t)) to ln(1.1), with FC_ut representing the fold change in concentration of the untreated sample with respect to time=0 and FC_t representing the same quantity, but for the treated sample.

Example 7: Statistical Analysis of dLAMP

Poisson statistics were used to calculate the 95% or 98% confidence interval of the NA concentration for each digital measurement. To calculate the error in fold change we used standard error-propagation methods (see, e.g., H. H. Ku. Notes on the use of propagation of error formulas. *Journal of Research of the National Bureau of Standards, Section C: Engineering and Instrumentation* 70C, 263-263 (1966)). With λ as a concentration and 6 the standard deviation, the equation is:

$$\sigma_{ratio} = \sqrt{\left(\frac{\sigma_{\lambda_2}}{\lambda_1}\right)^2 + \left(\frac{\lambda_2 \cdot \sigma_{\lambda_1}}{\lambda_1^2}\right)^2}$$

Kreutz, et. al., *Anal. Chem.* 83, 8158-8168 (2011) demonstrated that results from a Z-test (assuming a normal distribution) and a permutation test are in very good agreement for various SlipChip designs. Therefore, it is appropriate to calculate P-values comparing digital NA concentrations with a one-sided Z-test. This Z-test asks if the control NA concentration ($\lambda_{control}$) is 1.10× higher than the treated NA concentration ($\lambda_{ABX}$) (26, 45):

$$Z = \frac{\ln(\lambda_{control}) - \ln(1.10 \cdot \lambda_{ABX})}{\sqrt{\sigma_{\ln(\lambda_{control})}^2 + \sigma_{\ln(\lambda_{ABX})}^2}}$$

Concentration (λ) and standard deviation (σ) for each digital NA measurement were calculated from the number of positive and negative compartments with Poisson statistics as described in Kreutz et al. for single volume digital NA quantification. A significance level of 0.05 was used.

Example 8: Optimization of LAMP Isothermal Amplification

We designed primers and optimized real-time LAMP in bulk solutions to maximize amplification speed, while eliminating background amplification. At very high nucleic acid concentrations, real-time bulk LAMP assays have been reported to be as fast as 5 min, but at the lower concentrations of a single target molecule present in a single digital partition (~1 copy/nL=$10^6$ copies/mL), amplification takes 10 min or more. To mimic the concentration of template in a single digital partition, we performed our bulk optimization experiments at ~$10^6$ copies/mL. We selected the *E. coli* 23S rDNA gene as the pathogen-specific NA sequence (dAST marker) and as the target for primer design as the marker for DNA replication in the context of AST. Pan-Enterobacteriaceae primers would be useful for targeting other UTI pathogens. Although we did not purposefully design our primers to include other Enterobacteriaceae pathogens, we were able to detect *Klebsiella pneumoniae* and *Proteus mirabilis* in pilot experiments using the same primers.

The LAMP optimization process (FIG. 7) consisted of four steps: 1) screening multiple LAMP primer sets for speed and lack of background amplification; 2) screening multiple loop primer pairs with the selected primer set from step one for speed and lack of background amplification; 3) testing the selected LAMP and loop primers with a range of magnesium ion (Mg) concentrations; and 4) selecting the optimal amplification temperature from the data obtained in step three. Each parameter was tested using a temperature gradient, which proved to be critical to minimizing the time-to-positive (TTP), the reaction time to detect a positive sample.

LAMP primer optimization experiments (FIG. 7, steps 1-2) were performed on a Roche LightCyler 96 using the SYBR Green I channel for readout, 6 μL reaction volumes, and the following concentrations of reagents: 20 mM Tris-HCl pH 8.8, 50 mM KCl, 10 mM $(NH_4)_2SO_4$, 0.1% Tween-20, 1.4 mM dNTPs, 2 μM Syto-9, 400 U/mL Bst 2.0 (New England Biolabs), ~700 copies/μL *E. coli* gDNA, and 8 mM $MgSO_4$. All samples were run across a temperature gradient spanning 60-72° C.

Figure 7:
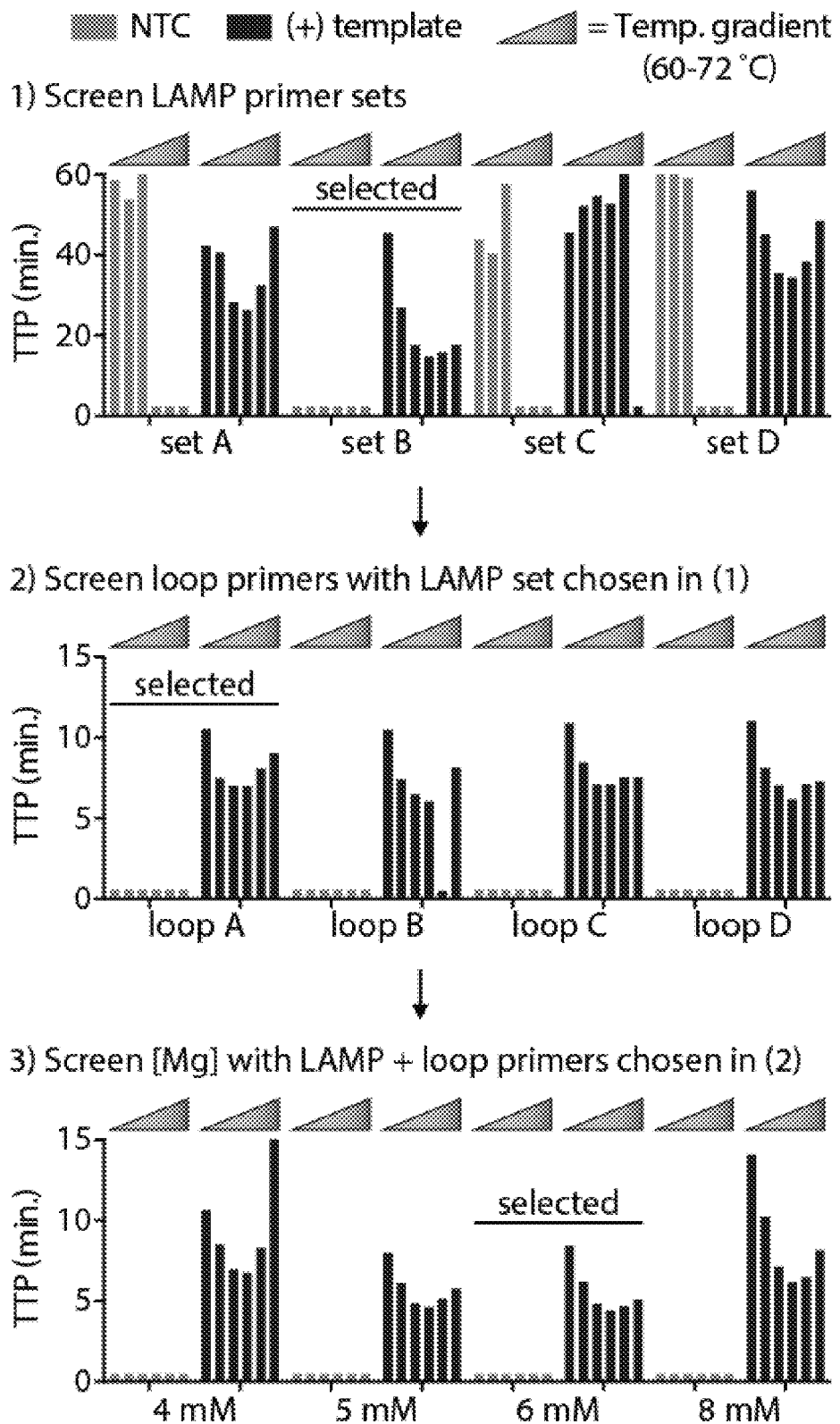
FIG. 7 shows a real-time LAMP optimization protocol used to reduce the time-to-positive (TTP) from 15 min to <5 min and results from screening at each step. Panels 1-3 of FIG. 7 show the results of 1) screening multiple LAMP primer sets for speed and lack of background amplification; 2) screening multiple loop primer pairs with the selected primer set from step one for speed and lack of background amplification; 3) testing the selected LAMP and loop primers with a range of magnesium ion (Mg) concentrations.

The experiments optimizing magnesium concentration (FIG. 7, step 3) were performed using the same protocol as above with the following concentrations of reagents: 20 mM Tris-HCl pH 8.8, 150 mM KCl, 10 mM $(NH_4)_2SO_4$, 0.1% Tween-20, 1.4 mM dNTPs, 2 μM Syto-9, 360 U/mL Bst 3.0 (New England Biolabs), ~700 copies/μL *E. coli* gDNA, and variable concentrations of $MgSO_4$ (FIG. 7). All samples were run across a temperature gradient spanning 60-74° C.

Primer concentrations were kept constant in all experiments: 1.6 μM FIP/BIP, 0.2 μM FOP/BOP, and 0.4 μM loopF/loopR (when included). Optimization was performed at a template concentration of ~700 copies/reaction or 0 copies/reaction (no template control, NTC). A value of 0.5 indicates no amplification was observed. N=1 for all time-to-positive (TTP) values.

Of the four tested LAMP primer sets, we selected set B as it showed the fastest amplification and no background amplification (FIG. 7, step 1). No loop primer pair showed much earlier TTPs than any other pair, and no pair showed theoretical or experimental evidence of primer-dimers. We selected the loop A set (FIG. 7, step 2).

The final selected primer set for *E. coli* 23S rDNA gene (dAST marker) amplification was as follows: GGCGT-TAAGTTGCAGGGTAT (FOP) (SEQ ID NO: 3), TCACGAGGCGCTACCTAA (BOP) (SEQ ID NO: 4), CGGTTCGGTCCTCCAGTTAGTGTTTTCCCGAAAC-CCGGTGATCT (FIP) (SEQ ID NO: 5), TAGCG-GATGACTTGTGGCTGGTTTTTCGGGGAGAACCAG-CTATC (BIP) (SEQ ID NO: 6), ACCTTCAACCTGCC-CATG (LoopF) (SEQ ID NO: 7), GTGAAAGGCCAAT-CAAACC (LoopR) (SEQ ID NO: 8).

Four concentrations of Mg were tested using the DNA polymerase Bst 3.0. The resulting TTPs varied by as much as 11 min depending on the amplification temperature. This optimization process resulted in TTPs as fast as ~4-5 min for ~700 target copies in a 6 µL amplification volume, with the fastest TTP (4.4 min) obtained using 6 mM Mg at 71° C.

Subsequent LAMP assays described in the following Examples use the same concentration of reagents as the experiments to optimize $MgSO_4$ concentration, but were run with 5 mM $MgSO_4$, unless otherwise noted. Although 6 mM $MgSO_4$ yielded the fastest TTP, 5 mM $MgSO_4$ was used in subsequent experiments in order to minimize the risk of background amplification. We have not observed background amplification with the primers described here, but other primer sets are sensitive to $MgSO_4$ concentration. The optimal TTP using 5 mM $MgSO_4$ was only 12 s slower than when using 6 mM $MgSO_4$. Under these conditions, the LAMP assay was optimized to reduct the time-to-positive (TTP) peak from 15 min to <5 min.

Example 9: Lamp Assay Specificity

Figures 8A, 8B:
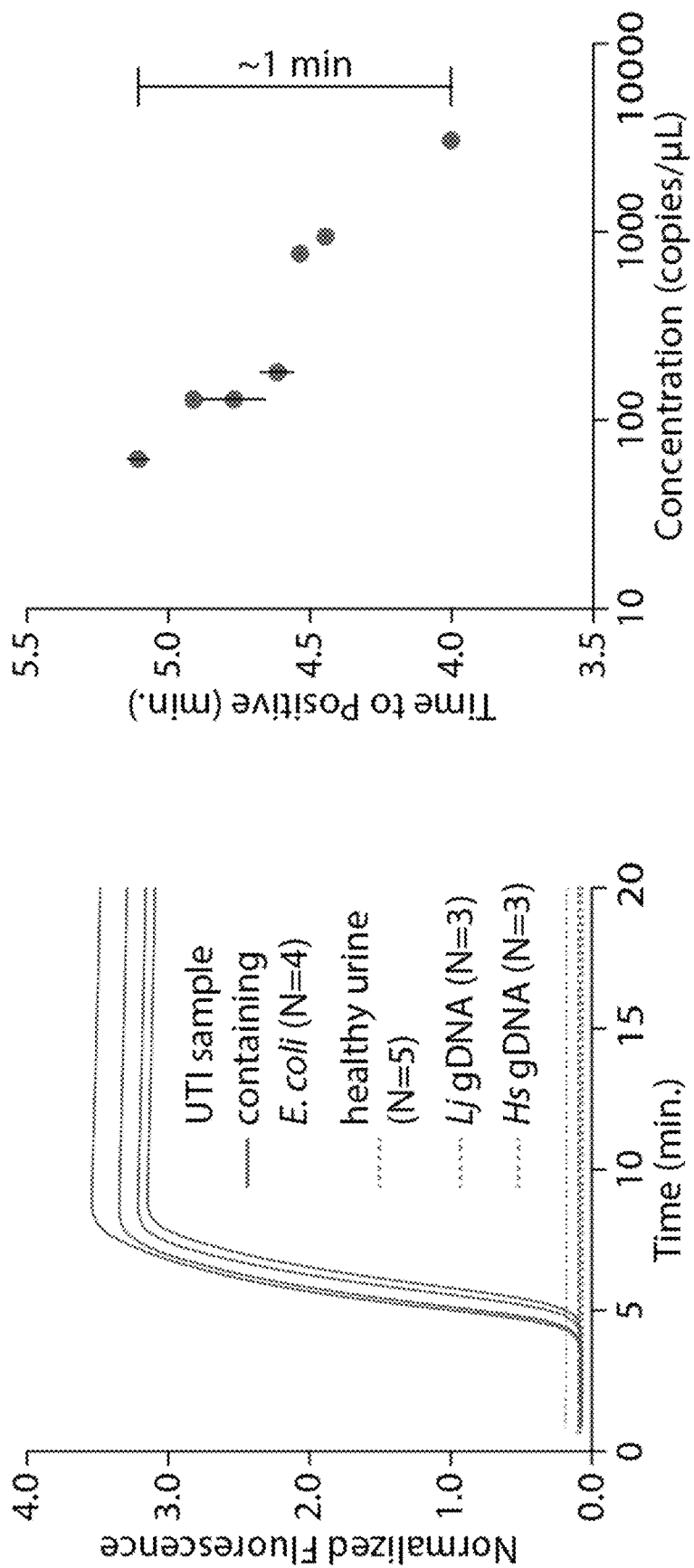
FIGS. 8A and 8B show the results of a LAMP specificity assay and compatibility with clinical samples. Real-time fluorescence readout of amplified DNA for UTI urine samples containing *E. coli* (solid lines), healthy urine samples, urine samples containing gDNA of *L. jensenii* (Lj), and urine samples containing human (Hs) gDNA (dashed lines) (FIG. 8A). TTP values for clinical UTI urine samples containing a range of pathogen concentrations (FIG. 8B). Error bars represent a single standard deviation from the average of technical triplicates. N=3 technical replicates for each TTP value.

Once LAMP primers and protocols had been optimized, we further tested their specificity for the dAST marker. BLAST was used to evaluate primer specificity against the families Enterobacteriaciae, Staphylococcaceae, and Enterococcaceae. The specificity of the LAMP primers targeting the *E. coli* 23S rDNA gene was tested against human genomic DNA (Hs gDNA), Lj gDNA, urine from healthy donors, and water (FIG. 8A). Hs gDNA was tested at 0.002, 0.02, and 0.2 ng/µL final reaction concentration as measured using a NanoDrop 2000c (Thermo Fisher Scientific). Lj gDNA was tested at final reaction concentrations of 0.16, 0.8, and 1.6 ng/µL, as measured using a NanoDrop 2000c. Urine from healthy donors was run at 10% final reaction volume.

Real-time LAMP amplification was also performed in a standard well-plate format using a range of concentrations of *E. coli* gDNA (Ec gDNA) prepared from clinical UTI urine samples and quantified using droplet digital PCR (FIG. 8B) to verify a correlation between TTP and target concentration, thus further showing specificity for the dAST marker.

Real-time LAMP amplification was performed in a standard-well plate format on a Roche LightCyler 96 using the SYBR Green I channel for readout, 6 µL reaction volumes, and the following concentrations of reagents: 20 mM Tris-HCl pH 8.8, 150 mM KCl, 10 mM $(NH_4)_2SO_4$, 0.1% Tween-20, 1.4 mM dNTPs, 2 µM Syto-9, 360 U/mL Bst 3.0 (New England Biolabs), ~700 copies/µL *E. coli* gDNA, and 5 mM $MgSO_4$. The primer set used is as described in Example 8, and provided in Table 1, below:

TABLE 1

LAMP primers in amplification reaction volume

| Name | Seq ID NO: | Sequence | Final Conc. |
|------|-----------|----------|-------------|
| FOP | 3 | GGCGTTAAGTTGCAGGGTAT | 0.2 µM |
| BOP | 4 | TCACGAGGCGCTACCTAA | 0.2 µM |
| FIP | 5 | CGGTTCGGTCCTCCAGTTAG TGTTTTCCCGAAACCCGGTG ATCT | 1.6 µM |
| BIP | 6 | TAGCGGATGACTTGTGGCTG GTTTTTCGGGGAGAACCAGC TATC | 1.6 µM |
| LOOPF | 7 | ACCTTCAACCTGCCCATG | 0.4 µM |
| LOOPR | 8 | GTGAAAGGCCAATCAAACC | 0.4 µM |

As shown in FIG. 8A, the primers only showed amplification in the presence of DNA extracted from samples containing *E. coli*. No positive signals were obtained when we ran real-time LAMP using Lj genomic DNA (gDNA), human gDNA, or urine from healthy donors with no symptoms of UTI. When testing clinical UTI samples, a positive signal was only obtained when *E. coli* DNA was present. TTPs ranged from 4-5 min for clinical UTI samples (FIG. 8B). However, using this LAMP method in a standard well-plate format to resolve a 1.5× difference in concentration would require detecting a difference in TTP of ~8 s, which is difficult in practice to perform robustly.

Example 10: AST Specificity from an Impure Sample

To show accurate determination of microorganism susceptibility using the present method, a susceptible and a resistant isolate of *E. coli* (Ec) from patients diagnosed with urinary tract infections (UTI) were treated separately with ("treated") and without ("control") antibiotics in the presence of varying concentrations of *Lactobacillus jensenii* (Lj) (from 0.1× to 1× to 10× relative to the concentration of the Ec present in the sample) also isolated from a UTI urine sample. The concentrations of Ec and Lj were estimated by optical density at 600 nm. Samples were exposed to 1 µg/mL ciprofloxacin for a total of 30 min. After 0, 15, and 30 min. of exposure, an aliquot of the sample was removed and total DNA extracted. Next, DNA from each extraction was quantified using droplet digital PCR with 23S primers specific to the Enterobacteriacea family, of which Ec is a member. The primers used for this PCR amplification are included in Table 2 and the PCR mix used is included in Table 3.

TABLE 2

PCR primer mix

| Name | SEQ ID NO: | Sequence | Conc. |
|---|---|---|---|
| forward | 1 | TGCCGTAACTTCGGGAGAAGGC | 10 µM |
| reverse | 2 | TCAAGGCTCAATGTTCAGTGTC | 10 µM |

TABLE 3

PCR mix used (per 10 µL reaction).

| Reagent | Volume added (µL) |
|---|---|
| Bio-Rad SsoFast EvaGreen qPCR Supermix | 5 |
| PCR primer mix | 0.5 |
| Nuclease-free water | 2.5 |
| Target | 2.0 |

Figure 9:
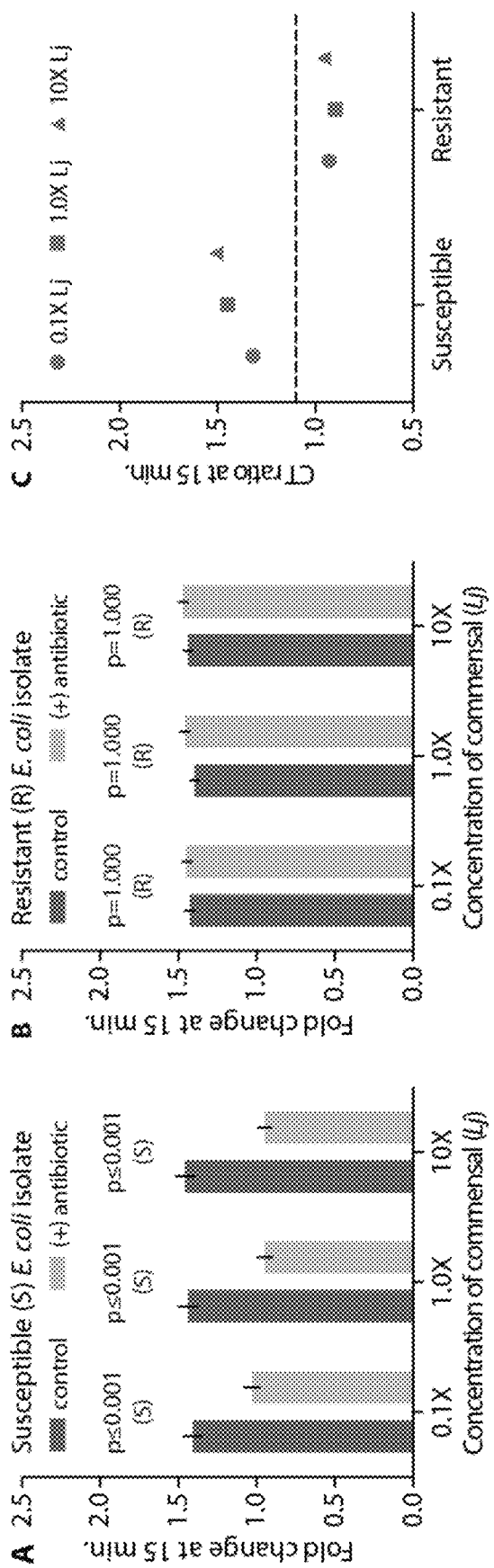
FIG. 9 shows the result of a dAST using dPCR in the presence of high concentrations of commensal bacteria. (A) A cip-susceptible *E. coli* isolate and (B) a cip-resistant *E. coli* isolate from the urine of patients diagnosed with UTIs were exposed to 1.0 μg/mL cip in the presence of varying amounts of *L. jensenii* (Lj), a common urine commensal. Fold changes relative to time 0 were compared as described in Schoepp et al. *Angew. Chem. Int. Ed. Engl.* 55, 9557-9561 (2016), and used to determine susceptibility. (C) Susceptibility determined using CT ratios after 15 min of antibiotic exposure for each concentration of Lj tested. N=2 technical replicates for each biological sample. Error bars are 98% confidence intervals.

FIG. 9A and FIG. 9B show the fold change in the concentration of DNA relative to time 0 in the control and treated samples after 15 min. of antibiotic exposure of E. coli in the presence of 0.1×, 1×, and 10× L. jensenii (i.e., 1:10, 1:1, and 10:1 L. Jensenii:E. coli, respectively). The significance of this difference is measured by the p-value and is calculated with Poisson statistics in the case of digital quantification. When the untreated sample has a significantly higher fold change than the treated sample, the bacteria is determined to be susceptible to the antibiotic. Here, susceptible and resistant Ec could be detected by our method even in the presence of commensal Lj from 0.1 to 10× the concentration of Ec.

The CT ratios at 15 min were calculated as the ratios of the marker concentrations in the control and ABX-treated samples to determine susceptibility (FIG. 9C). N=2 technical replicates for each biological sample. Error bars are 98% confidence intervals.

Example 11: Digital AST (dAST) Using Ultrafast Single-Molecule Counting (Digital LAMP)

We tested whether using the optimized LAMP chemistry in a digital format would yield accurate determination of ABX susceptibility while preserving the speed observed in bulk solutions. This would require the ability to resolve small changes in NA concentrations that occur after a 15 min exposure to ABX, despite any heterogeneity in TTPs (the difference in amplification kinetics of individual molecules), which has been observed previously. Because sample matrices might increase the heterogeneity in TTPs and thus decrease resolution, we tested clinical urine samples, which can contain urea, proteins, blood (including heme as a potent PCR inhibitor), and other cellular components that can interfere with assay detection. To eliminate extracellular DNA present in clinical urine as a potential source of error, we include DNase during the antibiotic exposure step to digest any extracellular DNA. We used the optimized LAMP assay from Example 8 with SlipChip microfluidic devices in a digital format. The SlipChip partitioned samples into 1,280 digital compartments. In each compartment, single molecules were amplified and counted in real time. We tested whether differences in NA concentrations between the control and ABX-treated samples could be resolved reliably using a single 1,280-well SlipChip for each measurement.

Figure 10:
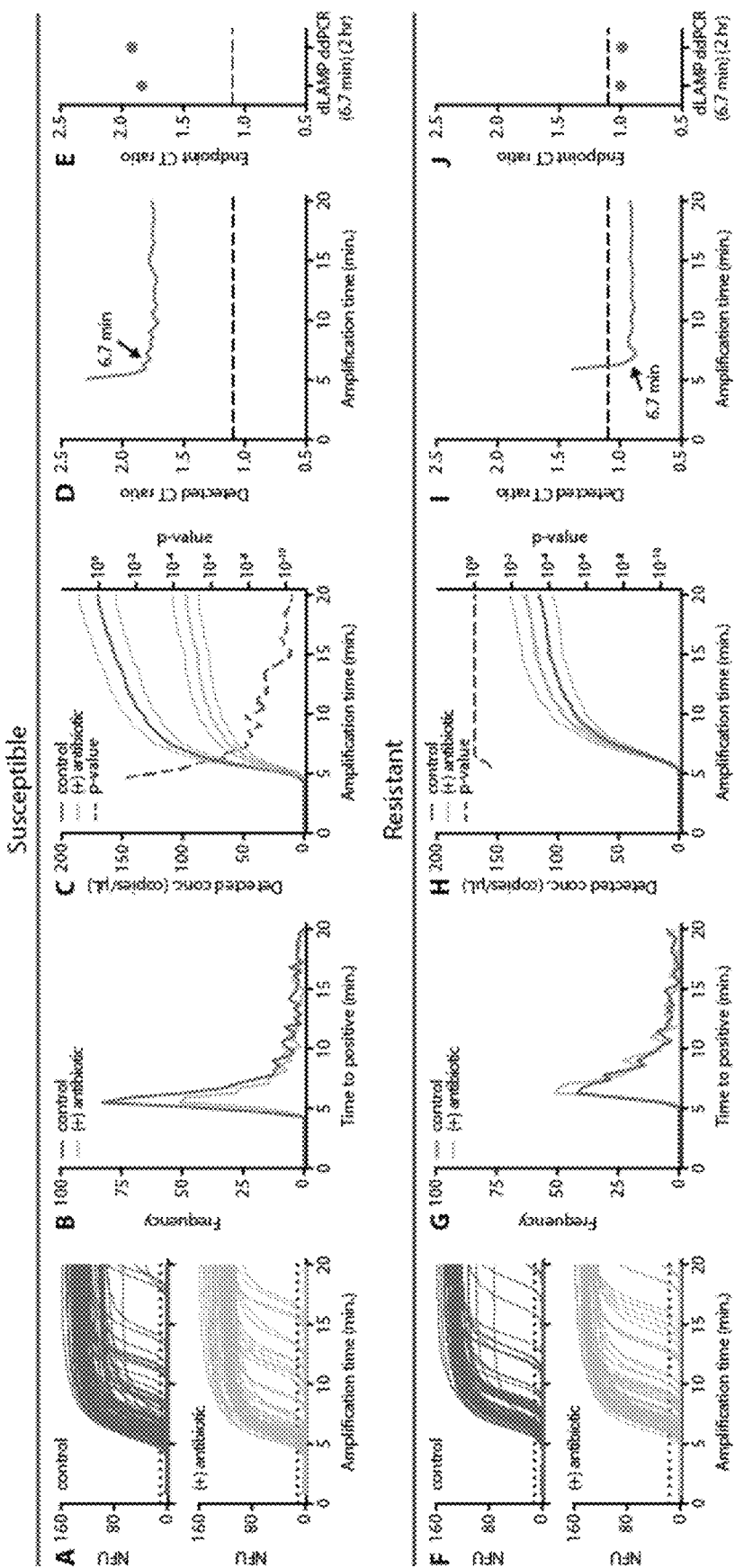
FIG. 10 shows the results of high-resolution single-molecule NA amplification using ultrafast dLAMP for dAST of clinical UTI urine samples. UTI urine samples with (A-E) antibiotic-susceptible and (F-J) antibiotic-resistant *E. coli*. (A, F) Real-time fluorescence amplification traces (200 of 1,280 traces shown for clarity). NFU=normalized fluorescence units; dotted line=positive threshold; when the normalized fluorescence intensity of a compartment crosses the threshold, that compartment is counted as positive. (B, G) TTP distribution determined by counting the number of compartments that crossed the positive threshold at each time point. (C, H) Detected concentrations of the target dAST marker in control and antibiotic-treated samples for successive image cycles. Note these curves are distinct from amplification curves shown in panels A and F. Grey lines represent 95% confidence intervals. P-values were calculated using a Z-test (see Statistical Analysis). (D, I) Detected CT ratios over time. Dashed line indicates susceptibility threshold. (E, J) Comparison of CT ratios for droplet digital PCR (ddPCR) after 2 h and dLAMP after 6.7 min of amplification.
Figure 11:
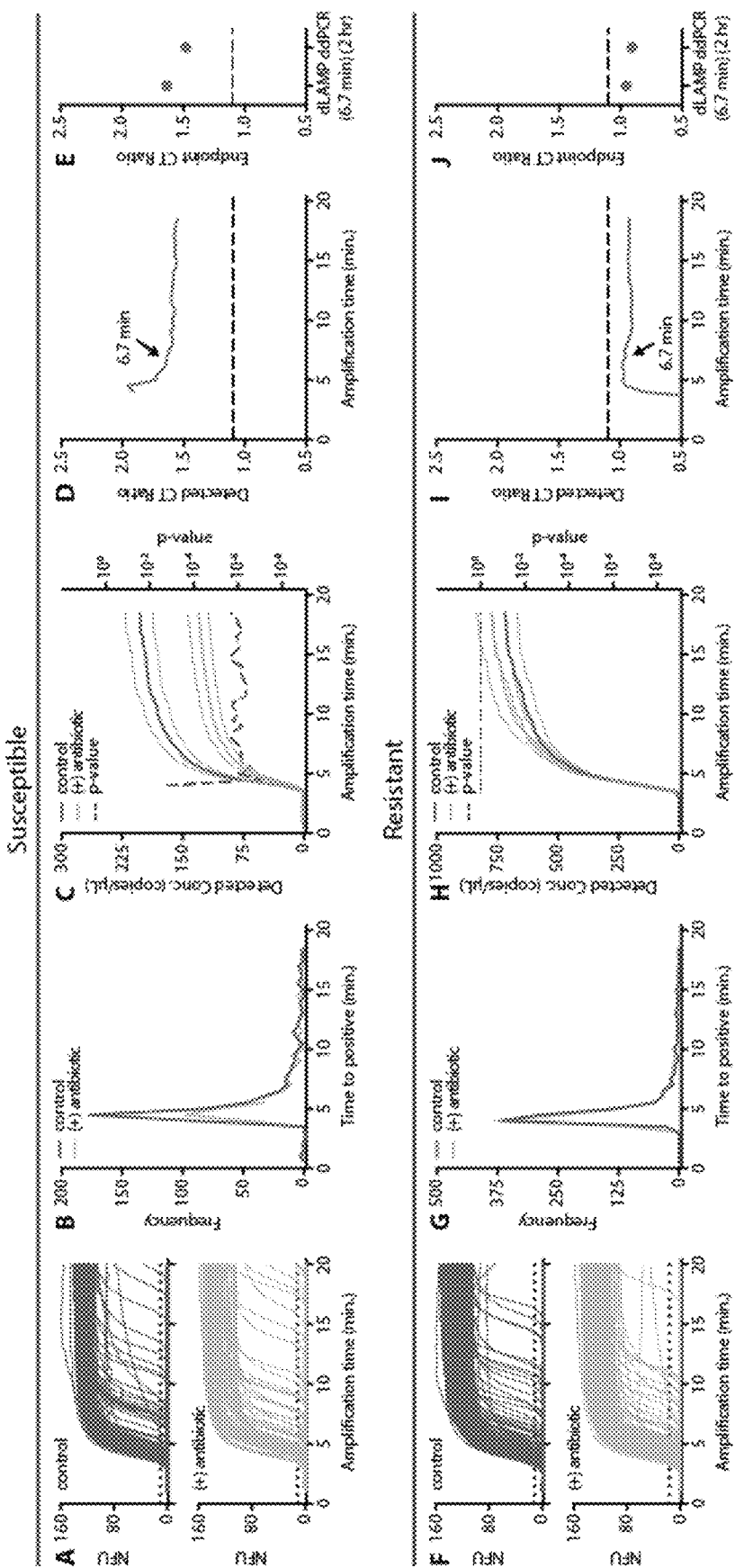
FIG. 11 shows the results of real-time dLAMP DNA quantification of a UTI sample with nitrofurantoin (nit) treatment. (A,F) Real-time fluorescence amplification traces (only 200 of 1,280 traces shown for clarity). NFU=normalized fluorescence units; dotted line=positive threshold; when the normalized fluorescence intensity of a compartment crosses the threshold, that compartment is counted as positive. (B,G) Time-to-positive (TTP) distribution was determined by counting the number of compartments that crossed the positive threshold at each time point. (C,H) Detected concentrations of the target dAST marker in control and antibiotic-treated samples for successive image cycles. Grey lines represent 95% confidence intervals. Note these curves are not the amplification curves shown in A and F. (D,I) Detected control-treated (CT) ratios over time. Dashed line indicates susceptibility threshold. (E,J) Comparison of CT ratios for droplet digital PCR (dPCR) after 2 h and dLAMP (after 6.7 min of amplification).

We performed this dLAMP assay for one cip-susceptible and one cip-resistant clinical urine sample (FIG. 10), and then again for one nit-susceptible and one nit-resistant clinical urine sample (FIG. 11).

Digital LAMP Amplification on a SlipChip was performed as follows: Two reagent solutions were loaded into two separate SlipChips. The first solution, which had a nucleic acid extraction from bacteria exposed to an antibiotic for 15 minutes, contained the following: 1 µL 10× IsoAmp buffer II, 0.2 µL 50 mg/mL BSA, 0.3 µL 100 mM $MgSO_4$, 0.4 µL BST 3.0 DNA polymerase (8000 U/mL), 0.5 µL 20×23S LAMP primer mix, 1.4 µL 10 mM dNTPs, 0.5 µL 40 µM Syto-9 dye, 4.7 µL nuclease-free water, and 1 µL nucleic acid extraction from the sample treated with antibiotic. The second solution, which had a nucleic acid extraction from bacteria without exposure to an antibiotic for 15 minutes, contained the following: 1 µL 10× IsoAmp buffer II, 0.2 µL 50 mg/mL BSA, 0.3 µL 100 mM $MgSO_4$, 0.4 µL BST 3.0 DNA polymerase (8000 U/mL), 0.5 µL 20×23S LAMP primer mix, 1.4 µL 10 mM dNTPs, 0.5 µL 40 µM Syto-9 dye, 4.7 µL nuclease-free water, and 1 µL nucleic acid extraction from the sample that was not treated with antibiotic. The two solutions were loaded onto two SlipChip devices and heated at 72° C. for 40 minutes on a custom-built real-time instrument. LAMP primers used were as described in Examples 8 and 9.

Experiments were performed on a Bio-Rad PTC-200 thermocycler with a custom machined block. The block contains a flat 3"×3" portion onto which the devices are placed ensuring optimal thermal contact. The excitation light source used was a Philips Luxeon S (LXS8-PW30) 1315 lumen LED module with a Semrock filter (FF02-475). Image Acquisition was performed with a VX-29MG camera and a Zeiss Macro Planar T F2-100 mm lens. A Semrock filter (FF01-540) was used as an emission filter.

Images acquired were analyzed using self-developed Labview software. The data were analyzed by first creating a binary mask that defined the location of each reaction volume within the image. The masked spots were then overlaid on the stack of images collected over the course of the experiment and the average intensity of each individual masked spot was tracked over the course of the stack. Background subtraction of the real-time trace was performed by creating a least mean square fit of each individual trace. Threshold was then manually set at the half height of the averaged maximum intensity, and the time-to-positive of each reaction was then determined as the point at which the real-time curve crossed the defined threshold.

Images were taken every 30 seconds and the fluorescent intensity was measured for each compartment. The number of positive compartments (those compartments with a fluorescent intensity exceeding the threshold) was monitored in real-time and a histogram of the number of positives was generated. The concentration of 23S was calculated using Poisson statistics and was based on the number of compartments that had exceeded a fluorescence intensity threshold. The significance of the difference in concentrations is measured by the p-value and is calculated with a concentration and standard error calculated from Poisson statistics, and the Z-test. When the untreated sample has a significantly higher concentration than the treated sample, the bacteria is determined to be susceptible to the antibiotic.

Using dLAMP to assay cip-susceptible and cip-resistant clinical urine sample exposed or not exposed to cip, most (>80%) single molecules amplified between 4-10 min, as shown by the fluorescence curves plotted in FIG. 10, panels A,F. As expected, heterogeneity in TTP was observed, likely as a result of the stochasticity of single-molecule amplification. Despite heterogeneity and matrix effects of clinical urine, we detected a significant difference in NA concentration ($P=6.1\times10^{-4}$) after only 5 min of amplification time for the cip-susceptible clinical urine sample (FIG. 10, panel C). For the cip-resistant sample, no significant difference in concentration was detected during the dLAMP assay (P>0.05) (FIG. 10, panel H). In both samples, the CT ratios were stable after 6 min and 40 seconds (6.7 min) of amplification (FIG. 10, panels D,I), were consistent with the ratios obtained by dPCR (FIG. 10, panels E,J), and yielded the correct AST call (susceptible vs. resistant).

We then repeated this dLAMP assay for one nit-susceptible and one nit-resistant clinical urine sample exposed or not exposed to nit. After 6.7 min of dLAMP amplification time, the CT ratios for both samples were stable, and the correct ABX-susceptibility call was determined (FIG. 11). This demonstrates that the optimized dLAMP assay yields correct AST calls in only 6.7 min, below the 10 min limit necessary to achieve a 30-min dAST.

Normally, a full 30-, 40-, or 60-minute amplification is performed to enable all digital units that contain a nucleic acid molecule to amplify. However, the results of these assays (FIG. 8A and FIG. 11) show that most digital units amplify within 10 minutes and that collecting a full data set at an amplification time of 6-10 minutes still enables the determination of a relative concentration difference between treated and untreated samples that is statistically significant.

Further, individual DNA target molecules were detected and the DNA concentration accurately quantified even after dilution during ABX exposure and sample preparation. Table 4 shows pathogen-specific 23S DNA concentration as determined by digital LAMP after 6.7 min of amplification time (FIG. 10, panels C/H). Taking into account the number of rDNA copies per *E. coli* chromosome, and the efficiency of dLAMP in counting DNA in 6.7 min, the concentration of full genomes is ~6 times lower than the number reported in this table. CFU/mL was determined by plate counting at the UCLA Clinical Microbiology Laboratory.

TABLE 4

Concentration of clinical urine samples determined by digital LAMP

| Caltech Sample # | 23S Conc. (cop/mL) | CFU/mL |
|---|---|---|
| 1 | 1.59E+07 | >100,000 |
| 2 | 2.52E+07 | >100,000 |
| 3 | 3.94E+07 | >100,000 |
| 4 | 5.63E+07 | >100,000 |
| 5 | 3.14E+07 | >100,000 |
| 6 | 7.86E+06 | >100,000 |
| 7 | 7.07E+06 | >100,000 |
| 8 | 5.08E+07 | >100,000 |
| 9 | 1.72E+07 | >100,000 |
| 10 | 2.64E+07 | >100,000 |
| 11 | 7.44E+06 | >100,000 |
| 12 | 2.75E+07 | >100,000 |
| 13 | 2.07E+07 | >100,000 |
| 14 | 1.55E+07 | >100,000 |
| 15 | 2.12E+08 | >100,000 |
| 16 | 1.59E+07 | >100,000 |
| 17 | 5.12E+07 | >100,000 |
| 18 | 1.44E+07 | >100,000 |
| 19 | 2.62E+07 | >100,000 |
| 20 | 4.52E+06 | >100,000 |
| 21 | 4.25E+07 | >100,000 |
| 22 | 1.30E+08 | >100,000 |
| 23 | 3.04E+07 | >100,000 |
| 24 | 2.38E+07 | >100,000 |
| 25 | 4.19E+07 | >100,000 |
| 26 | 1.92E+07 | >100,000 |
| 27 | 4.63E+07 | >100,000 |
| 28 | 3.62E+07 | >100,000 |
| 29 | 6.21E+06 | >100,000 |
| 30 | 2.38E+07 | >100,000 |
| 31 | 2.98E+07 | >100,000 |
| 32 | 9.57E+07 | >100,000 |
| 33 | 1.08E+08 | >100,000 |
| 34 | 1.13E+08 | >100,000 |
| 35 | 4.84E+07 | >100,000 |
| 36 | 5.73E+07 | >100,000 |
| 37 | 1.59E+07 | >100,000 |
| 38 | 8.49E+07 | >100,000 |
| 39 | 3.18E+06 | 50,000 |
| 40 | 2.45E+07 | >100,000 |
| 41 | 1.02E+08 | >100,000 |
| 42 | 1.26E+07 | >100,000 |
| 43 | 4.97E+06 | >100,000 |
| 44 | 1.69E+08 | >100,000 |
| 45 | 2.46E+08 | >100,000 |
| 46 | 8.78E+06 | >100,000 |
| 47 | 8.58E+06 | >100,000 |
| 48 | 1.21E+07 | >100,000 |
| 49 | 1.41E+07 | >100,000 |
| 50 | 3.06E+06 | >100,000 |
| 51 | 8.02E+06 | >100,000 |

Example 12: Preliminary Quantification

In parallel with the 15 min antibiotic exposure step, we performed bulk qLAMP on the urine samples as a semi-quantitative indicator to inform the dilution factor necessary to be within the dynamic range of the 1,280 well SlipChip for digital amplification analysis. To perform the semi-quantitative qLAMP, a 2 µL aliquot from each of the control and treated DNA extractions from time 0 were added to an 8 µL LAMP mix. The samples, along with 2 standards with known DNA concentration (S1=128.5 copies/µL and S2=766.0 copies/µL), were then incubated at 72° C. for 5 min on a Roche LightCycler 96 and fluorescent traces were monitored in real-time. If the TTP of the average of the samples was earlier than the TTP of S1, then 3 µL of the NA aliquot extracted at 15 min were added to 24 µL of dLAMP mix, along with 3 µL of NF—$H_2O$. If the TTP of the sample was between the TTPs of S1 and S2, then 6 µL of the 15-min NA extraction was added to 24 µL of dLAMP mix, with no additional NF—$H_2O$ added. This step was completed within the 15 min of antibiotic exposure and guided the dilution factor of nucleic acids into the SlipChips in order to ensure that the concentration was within the dynamic range (e.g., the range shown in FIG. 8B) and could be quantified with high resolution.

Example 13: 30 Minute Sample-to-Answer Digital AST Directly from Clinical Urine Samples We tested whether the entire dAST workflow (FIG. 2, ABX exposure, sample preparation, measurement, and data analysis) could be performed in less than 30 min. To accomplish this goal, the sample-preparation time was shortened from 10 min to 2 min while maintaining compatibility with dLAMP. In parallel with ABX exposure of a clinical sample, rapid real-time LAMP was used to confirm the presence of *E. coli* and to measure the approximate NA concentration of the dAST marker in the sample (semi-quantitation). This step provided identification of the pathogen and could be used to select the amount of NAs loaded on the chip to maximize the performance of the digital assay without adding time to the workflow; it also avoided the AST quantification step for samples lacking the pathogen or containing sub-clinical amounts. We performed real-time image-analysis to calculate the concentrations of the dAST marker in real-time from each image, instead of after completion of amplification. We tested whether these steps could be performed in succession to provide a full sample-to-answer workflow, including all fluid-transfer steps and data analysis, within 30 min.

Specifically, a clinical urine sample from patients suspected of having a UTI and identified to contain *E. coli* (Ec) was treated separately with ("treated") and without ("untreated") 1 µg/mL ciprofloxacin. The final sample mixture in each tube was 10 µL clinical urine sample, 250 µL BHI media, 25 µL DNAse I (NEB), 5 µL DNAse buffer (100 mM Tris-HCl, 25 mM $MgCl_2$, and 5 mM $CaCl_2$), and 210 µL DI water. 0.5 µL 1 mg/mL ciprofloxacin was added to the "treated" tube. The treated ("(−) ABX") and untreated ("(+) ABX") samples were shaken at 750 rpm at 37° C. for a total of 30 min.

In parallel with the 15-min antibiotic-exposure step, we used the semi-quantitative ability of quantitative LAMP to predict the appropriate dilution factor for our 1,280-well digital SlipChips. 20 µL of each sample ("(−) ABX" and "(+) ABX") was added to and mixed with 80 µL of one-step DNA extraction buffer (Epicentre QE9050) which had been heated to 98° C. The two samples were then heated at 120° C. for 1 minute, after which they were chilled on ice for 30 seconds, vortexed, and centrifuged. 2 µL of each extraction was added to 8 µL LAMP mix. The primers used for this LAMP amplification and the LAMP mix used is as described in Example 12. The samples, along with two standards with known DNA concentration (S1=128.5 copies/µL and S2=766.0 copies/µL), were then incubated at 72° C. for 5 min on a Roche LightCycler 96 and fluorescent traces were monitored in real-time. If the TTP of the average of the samples was earlier than the TTP of S1, then 3 µL of the NA aliquot extracted at 15 min were added to 24 µL of dLAMP mix, along with 3 µL of NF—$H_2O$. If the TTP of the sample was between the TTPs of S1 and S2, then 6 µL of the 15-min NA extraction was added to 24 µL of dLAMP mix, with no additional NF—$H_2O$ added. This step was completed within the 15 min of antibiotic exposure. In this example, the TTP was earlier than the TTP of S1.

After 0 and 15 minutes of antibiotic exposure, 20 µL of each sample appropriately diluted according to the results of the semi quantitation ("(−) ABX" and "(+) ABX") was added to and mixed with 80 µL of one-step DNA extraction buffer (Epicentre QE9050) which had been heated to 98° C. The two samples were then heated in a heating block set to 120° C. for 1 minute, after which they were chilled on ice for 30 seconds, vortexed, and centrifuged. 3 µL of each extraction was added to 24 µL LAMP mix along with 3 µL nuclease-free water. This solution was then pipette-mixed and simultaneously loaded into two separate SlipChips. After partitioning into 1200 compartments, the SlipChips were placed onto the thermal cycler of a real-time imaging instrument at 72° C.

Images were taken every 26 s and concentrations were calculated based on the number of positive and negative wells as each image was taken instead of after the assay completed. CT ratios were also calculated for each time point; the value of the CT ratio after 6.7 min of amplification time is plotted in FIG. 12 and was compared to a threshold of 1.10 to determine susceptibility or resistance.

Figure 12:
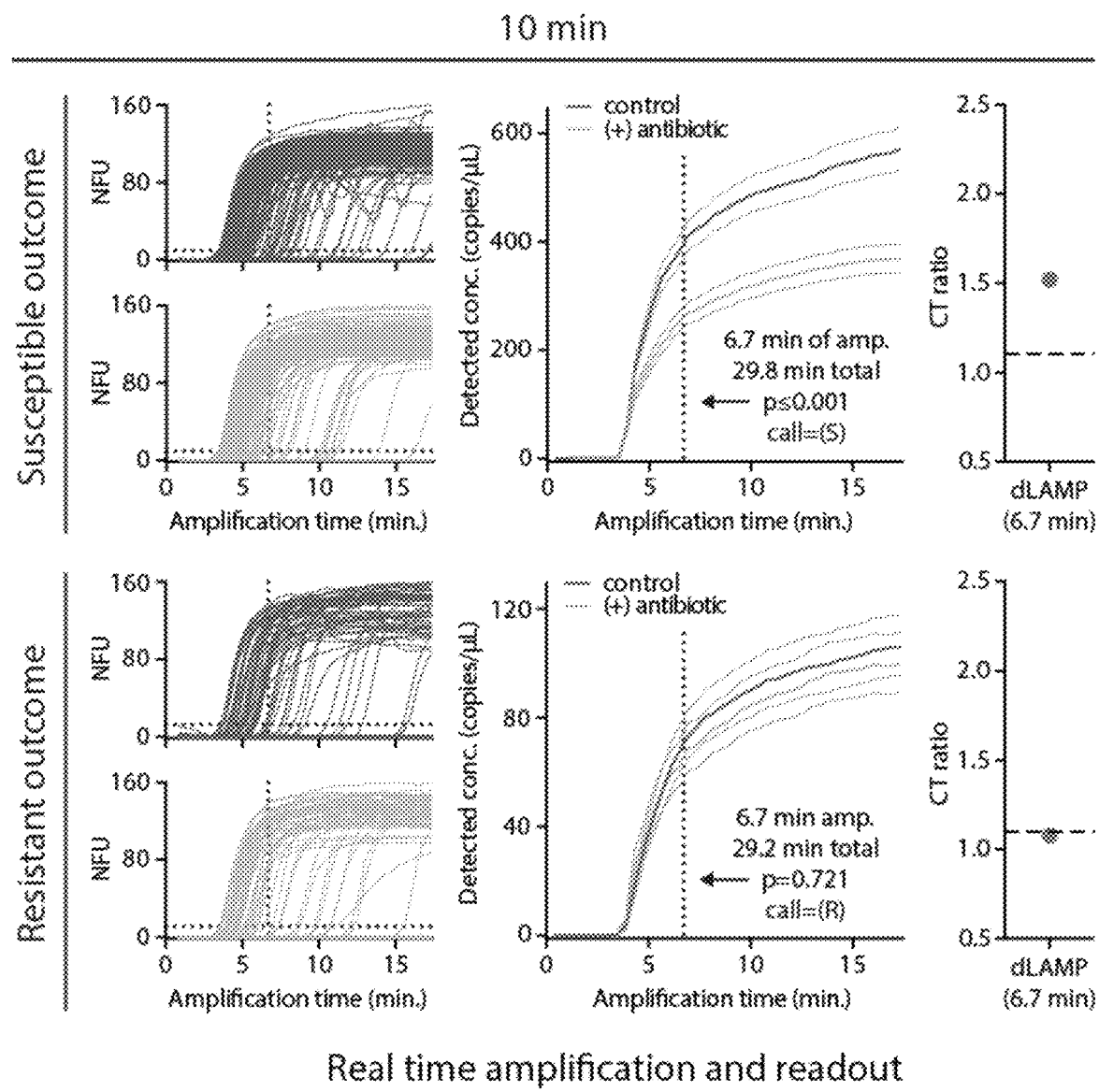
FIG. 12 shows the results of a complete sample-to-answer AST performed in less than 30 minutes. dLAMP was monitored in real time and a susceptibility call determined after 6.7 min of amplification; data for one resistant and one susceptible sample are shown. P-values were calculated using a Z-test (see Statistical Analysis). NFU=normalized fluorescence units. Grey lines represent 95% confidence intervals.

The entire process from addition of an infected clinical urine sample to media with and without cip to final determination of susceptibility or resistance of the microorganism using the CT ratio was performed in 29.8 min (including 6.7 min of dLAMP amplification time to CT ratio determination). From this process, the software reported the control and treated concentrations for the cip-susceptible sample to be significantly different (P=7.4×10$^{-10}$), with a CT ratio of 1.59 (FIG. 12). For the cip-resistant sample, no significant difference in concentration was reported through the entire dLAMP assay (P>0.05). At 29.2 min (6.7 min of dLAMP amplification time) the CT ratio for the cip-resistant sample was 0.98 (FIG. 12). This result shows how a combination of rapid partitioning, fast isothermal amplification, and high-resolution digital measurements enabled ABX susceptibility to be determined in less than 30 min.

Note that not all digital compartments become positive at the same time; some compartments show delayed amplification. This could present a delay if all of the amplification curves, including those showing delayed amplification, had to be analyzed. This approach takes advantage of the fact that this comparison does not require determination of absolute counts of an AST marker. Relative counts of AST markers in the exposed vs unexposed samples could be compared. To achieve this comparison rapidly, we compare the number of positive compartments in the exposed and unexposed samples in real time, and use these numbers to calculate the apparent concentration of the dAST marker. Poisson statistics were used to determine whether the obtained apparent concentrations are likely to be statistically different or the same.

In combination these approaches allowed us to determine susceptibility in about 6.7 minutes after the start of amplification.

Example 14: Digital AST Using a Set of 51 Clinical Samples

Having established that the dAST method can be performed, sample-to-answer, in less than 30 min, we next tested dAST with 51 clinical samples using both dPCR and dLAMP readouts. Samples were exposed to ABX for 15 min and NA extraction was performed on a total of 51 clinical UTI samples containing ≥5×10$^4$ CFU/mL *E. coli:* 17 cip-susceptible, 14 cip-resistant, 18 nit-susceptible, and 5 nit-resistant. Three clinical samples were tested separately with cip and nit, for a total of 54 tests.

Clinical urine samples in the following examples were obtained under an approved Institutional Review Board (IRB) protocol at the UCLA CML (#15-001189) and analyzed at the California Institute of Technology (Caltech) under approved protocol IRB #15-0566. Samples were de-identified before being transported to Caltech. Samples were stored in Vacutainer Plus C&S Boric Acid Sodium Borate/Formate Tubes (Becton Dickinson), transported at ambient temperature, and stored at 4° C. once received at Caltech.

Urine samples were from otherwise healthy patients suspected of having a UTI (based on urinalysis results). Pathogens from the urine samples were isolated and identified using mass spectrometry. Broth microdilution AST was performed on samples positive for *E. coli*. Urine samples were selected for dAST analysis based on the determined MIC of the infecting *E. coli*. Samples were considered cip-susceptible if the determined MIC≤0.25 µg/mL and considered cip-resistant if the MIC≥4 µg/mL. Samples were considered nit-susceptible if the MIC≤16 µg/mL and nit-resistant if the MIC≥128 µg/mL.

Figure 13:
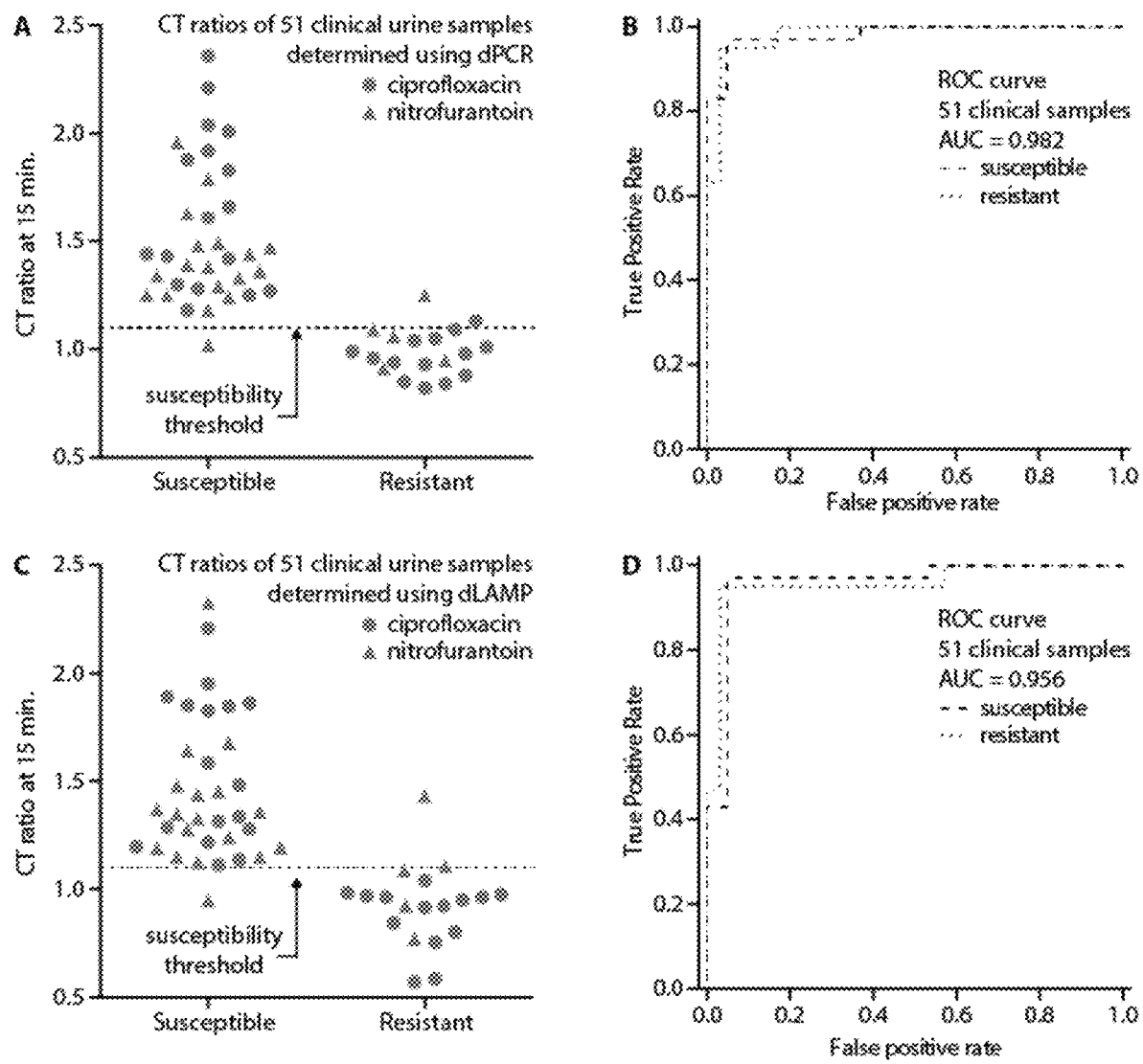
FIG. 13 shows the result of dAST directly from clinical samples using dPCR (slow) and dLAMP (fast) for quantification. (A, C) Antibiotic susceptibility of 51 clinical *E. coli*-infected UTI samples determined using CT ratios after 15 min of exposure to nit and cip (35 susceptible, 19 resistant, and three samples tested for both antibiotics). NA concentrations were quantified with dPCR (A) and dLAMP (C). (B, D) Receiver operating characteristic (ROC) curves for the dAST method as measured by dPCR (B) and dLAMP (D).

We quantified the DNA AST marker of the control and treated extractions on all 54 samples with both dPCR and dLAMP, as described in the above examples. For each sample, the CT ratio was calculated and compared to a susceptibility threshold (1.10) to classify samples as resistant or susceptible (FIG. 13A). Injection-molded SlipChips were used for clinical samples 28-29 and 48-51 with the rapid dLAMP assay, with the rest being done in glass SlipChips. These disposable injection molded SlipChips contained 5,376 2.4-nL compartments, which enable shorter turnaround times between experiments.

Discordant CT ratios were observed for five samples when compared with the gold-standard broth microdilution method. To resolve the discrepancy, we reran three of these five discordant samples, averaging the second CT ratio with the CT ratio from the first run to obtain a consensus value of the CT ratio (Samples #28, #29, #36 in table 5). As a control, we also reran one sample that was not discordant (Sample #122 in table 5).

TABLE 5

Clinical samples used in this study. Clinical urinary tract infection (UTI) urine samples tested for ciprofloxacin (cip) or nitrofurantoin (nit) susceptibility testing by gold-standard broth microdilution and by digital AST (dAST). Nucleic acids were quantified with both digital PCR (dPCR) and digital LAMP (dLAMP). Sample reruns (indicated by a "(2)") were performed several hours later on the same day when the control-treated ratio was discordant with the gold-standard AST call (CT ratio > 1.10 for a resistant sample or <1.10 for a susceptible sample).

| Caltech Sample # | UCLA ID # | Description (Color, Turbidity) | ABX | MIC (µg/mL) | Gold-standard AST call | CT Ratio (dPCR) | dAST call (dPCR) | CT Ratio (dLAMP, 6.7 min) | dAST call (dLAMP) |
|---|---|---|---|---|---|---|---|---|---|
| 1 | 15-31A-020 | red, clear | nit | <16 | S | 1.48 | S | 1.64 | S |
| 2 | 15-31A-022 | light yellow, clear | cip | <=0.25 | S | 1.44 | S | 1.34 | S |
| 3 | 15-31A-025 | light yellow, clear | nit | <16 | S | 1.33 | S | 1.33 | S |
| 4 | 15-31A-026 | light yellow, clear | nit | <16 | S | 1.36 | S | 1.35 | S |
| 5 | 15-31A-027 | light yellow, clear | nit | <16 | S | 1.25 | S | 1.24 | S |
| 6 | 15-31A-031 | colorless, clear | cip | >=4 | R | 1.09 | R | 0.95 | R |
| 6 | 15-31A-031 | colorless, clear | nit | 256 | R | 0.95 | R | 0.77 | R |
| 7 | 15-31A-039 | light yellow, clear | cip | >=4 | R | 0.99 | R | 0.84 | R |
| 8 | 15-31A-040 | light yellow, clear | nit | 128 | R | 1.06 | R | 1.09 | R |
| 9 | 15-31A-042 | dark yellow, clear | cip | <=0.25 | S | 1.92 | S | 1.83 | S |
| 10 | 15-31A-043 | light yellow, clear | cip | <=0.25 | S | 1.66 | S | 1.85 | S |
| 10 | 15-31A-043 | light yellow, clear | nit | 128 | R | 0.91 | R | 0.92 | R |
| 11 | 15-31A-049 | light yellow, clear | cip | >=4 | R | 0.96 | R | 1.04 | R |
| 12 | 15-31A-050 | dark yellow, cloudy | cip | >=4 | R | 0.88 | R | 0.96 | R |
| 13 | 15-31A-051 | light yellow, cloudy | cip | >=4 | R | 0.98 | R | 0.97 | R |
| 14 | 15-31A-054 | light yellow, cloudy | cip | <=0.25 | S | 1.42 | S | 1.48 | S |
| 15 | 15-31A-056 | light yellow, cloudy | nit | 256 | R | 1.09 | R | 1.106 | S** |
| 16 | 15-31A-060 | light yellow, cloudy | cip | <=0.25 | S | 1.83 | S | 1.31 | S |
| 17 | 15-31A-063 | yellow, cloudy | cip | <=0.25 | S | 1.28 | S | 1.111 | S |
| 18 | 15-31A-066 | yellow, cloudy | cip | >=4 | R | 0.85 | R | 0.80 | R |
| 19 | 15-31A-067 | light yellow, cloudy | cip | >=4 | R | 0.82 | R | 0.59 | R |
| 20 | 15-31A-068 | light yellow, cloudy | cip | >=4 | R | 0.84 | R | 0.57 | R |
| 21 | 15-31A-071 | light yellow, cloudy | cip | >=4 | R | 1.04 | R | 0.92 | R |
| 22 | 15-31A-079 | light yellow, cloudy | nit | 128 | R | 1.25 | S** | 1.43 | S** |
| 23 | 15-31A-084 | yellow, clear | cip | >=4 | R | 1.01 | R | 0.96 | R |
| 24 | 15-31A-086 | yellow, cloudy | cip | <=0.25 | S | 2.01 | S | 2.21 | S |
| 25 | 15-31A-088 | yellow, cloudy | cip | <=0.25 | S | 1.25 | S | 1.22 | S |

TABLE 5-continued

Clinical samples used in this study. Clinical urinary tract infection (UTI) urine samples tested for ciprofloxacin (cip) or nitrofurantoin (nit) susceptibility testing by gold-standard broth microdilution and by digital AST (dAST). Nucleic acids were quantified with both digital PCR (dPCR) and digital LAMP (dLAMP). Sample reruns (indicated by a "(2)") were performed several hours later on the same day when the control-treated ratio was discordant with the gold-standard AST call (CT ratio > 1.10 for a resistant sample or <1.10 for a susceptible sample).

| Caltech Sample # | UCLA ID # | Description (Color, Turbidity) | ABX | MIC (µg/mL) | Gold-standard AST call | CT Ratio (dPCR) | dAST call (dPCR) | CT Ratio (dLAMP, 6.7 min) | dAST call (dLAMP) |
|---|---|---|---|---|---|---|---|---|---|
| 26 | 15-31A-089 | light yellow, clear | cip | >=4 | R | 0.94 | R | 0.91 | R |
| 27 | 15-31A-091 | yellow, cloudy | cip | <=0.25 | S | 1.18 | S | 1.19 | S |
| 28 | 15-31A-093 | orange/red, clear | cip | <=0.25 | S | 1.08 | R | — | — |
| 28(2) | 15-31A-093 | orange/red, clear | cip | <=0.25 | S | 1.88 | S | 1.59 | S |
| 28_avg | 15-31A-093 | orange/red, clear | cip | <=0.25 | S | 1.48 | S | — | — |
| 29 | 15-31A-096 | light yellow, cloudy | cip | >=4 | R | 1.20 | S | — | — |
| 29(2) | 15-31A-096 | light yellow, cloudy | cip | >=4 | R | 0.93 | R | 0.98 | R |
| 29_avg | 15-31A-096 | light yellow, cloudy | cip | >=4 | R | 1.07 | R | — | — |
| 30 | 15-31A-097 | light yellow, cloudy | cip | >=4 | R | 1.13 | S** | 0.98 | R |
| 31 | 15-31A-101 | light yellow, clear | nit | <16 | S | 1.39 | S | 1.19 | S |
| 32 | 15-31A-102 | dark yellow, clear | nit | <16 | S | 1.63 | S | 1.68 | S |
| 33 | 15-31A-103 | light yellow, clear | nit | <16 | S | 1.38 | S | 1.28 | S |
| 34 | 15-31A-105 | light pink, cloudy | nit | <16 | S | 1.47 | S | 1.44 | S |
| 35 | 15-31A-108 | yellow, cloudy | nit | <16 | S | 1.29 | S | 1.37 | S |
| 36 | 15-31A-111 | yellow, clear | nit | <16 | S | 1.02 | R* | — | — |
| 36(2) | 15-31A-111 | yellow, clear | nit | <16 | S | 1.16 | S | 0.95 | R* |
| 36_avg | 15-31A-111 | yellow, clear | nit | <16 | S | 1.09 | R | — | — |
| 37 | 15-31A-112 | yellow, clear | nit | <16 | S | 1.49 | S | 1.12 | S |
| 38 | 15-31A-114 | light yellow, clear | nit | <16 | S | 1.34 | S | 1.36 | S |
| 39 | 15-31A-115 | yellow, clear | nit | <16 | S | 1.44 | S | 1.48 | S |
| 40 | 15-31A-116 | dark yellow, cloudy | cip | >=4 | R | 1.05 | R | 0.75 | R |
| 40 | 15-31A-116 | dark yellow, cloudy | nit | <16 | S | 1.96 | S | 2.33 | S |
| 41 | 15-31A-118 | yellow, clear | nit | <16 | S | 1.25 | S | 1.15 | S |
| 42 | 15-31A-119 | light yellow, clear | cip | <=0.25 | S | 2.21 | S | 1.95 | S |
| 43 | 15-31A-122 | light yellow, clear | nit | <16 | S | 1.17 | S | — | — |
| 43(2) | 15-31A-122 | light yellow, clear | nit | <16 | S | 1.79 | S | 1.45 | S |
| 43_avg | 15-31A-122 | light yellow, clear | nit | <16 | S | 1.48 | S | — | — |
| 44 | 15-31A-123 | yellow, cloudy | nit | <16 | S | 1.18 | S | 1.15 | S |
| 45 | 15-31A-126 | light yellow, clear | nit | <16 | S | 1.24 | S | 1.19 | S |
| 46 | 15-31A-131 | light yellow, clear | cip | <=0.25 | S | 1.61 | S | 1.28 | S |
| 47 | 15-31A-132 | dark yellow, clear | cip | <=0.25 | S | 1.27 | S | 1.14 | S |
| 48 | 15-31A-133 | dark yellow, cloudy | cip | <=0.25 | S | 1.30 | S | 1.29 | S |
| 49 | 15-31A-134 | dark yellow, clear | cip | <=0.25 | S | 2.36 | S | 1.85 | S |

TABLE 5-continued

Clinical samples used in this study. Clinical urinary tract infection (UTI) urine samples tested for ciprofloxacin (cip) or nitrofurantoin (nit) susceptibility testing by gold-standard broth microdilution and by digital AST (dAST). Nucleic acids were quantified with both digital PCR (dPCR) and digital LAMP (dLAMP). Sample reruns (indicated by a "(2)") were performed several hours later on the same day when the control-treated ratio was discordant with the gold-standard AST call (CT ratio > 1.10 for a resistant sample or <1.10 for a susceptible sample).

| Caltech Sample # | UCLA ID # | Description (Color, Turbidity) | ABX | MIC (µg/mL) | Gold-standard AST call | CT Ratio (dPCR) | dAST call (dPCR) | CT Ratio (dLAMP, 6.7 min) | dAST call (dLAMP) |
|---|---|---|---|---|---|---|---|---|---|
| 50 | 15-31A-136 | light yellow, clear | cip | <=0.25 | S | 2.04 | S | 1.89 | S |
| 51 | 15-31A-137 | dark yellow, clear | cip | <=0.25 | S | 1.43 | S | 1.28 | S |

S = antibiotic-susceptible;
R = antibiotic-resistant;
*major error;
**very major error.

With 1.10 as the susceptibility threshold for dPCR measurements, the dAST method returned 51 correct calls (94.4% categorical agreement), 2 very major errors for 19 resistant samples (10.5%), and 1 major error for 35 susceptible samples (2.9%). Because 1.10 was a threshold based on experiments with isolates (Schoepp et al., 2016), we generated a receiver operating characteristic (ROC) curve to inform the optimal threshold for clinical UTI samples (FIG. 13B). ROC curves show the ability of a diagnostic test to discriminate positives and negatives based on a threshold: values below the threshold are called negative (resistant) and values above the threshold are called positive (susceptible). The area under the curve (AUC) for the generated ROC was 0.98. Using the optimal threshold given by the ROC curve (1.14), 53 of 54 dAST calls matched the gold-standard AST call (98.1% categorical agreement) with 1 very major error (5.3%) and 0 major errors (0%).

We also used dLAMP (as done in Example 13) to quantify the same 54 samples. The CT ratios at 6.7 min were calculated and plotted in FIG. 13C, along with the ROC curve for dLAMP (FIG. 13D). With 1.10 as the susceptibility threshold for dLAMP measurements at 6.7 min, the dAST method returned 51 correct calls (94.4% categorical agreement), 2 very major errors for 19 resistant samples (10.5%), and 1 major error for 35 susceptible samples (2.6%). The AUC for the generated ROC curve was 0.96. Using the optimal threshold given by the ROC curve (1.11), 52 of 54 dAST calls matched the gold-standard AST call (96.3% categorical agreement) with 1 very major error (5.3%) and 1 major error (2.9%). These data show that although the optimal thresholds derived from ROC curves (1.14 for dPCR and 1.11 for dLAMP) slightly improve the categorical agreement, they are consistent with the threshold established for isolates (1.10) and are consistent with each other. Quantifying DNA with dLAMP at 6.7 min produces similar CT ratios and susceptibility calls as dPCR.

We define the true positive rate (sensitivity) as the proportion of gold-standard susceptible samples that are correctly identified as susceptible by the dAST method and the true negative rate (specificity) as the proportion of gold-standard resistant samples that are correctly identified as resistant by the dAST method.

Thus, our rapid process provides an accuracy comparable to longer methods of AST determination made after an endpoint reading of a reaction, such as digital PCR, but enables reliable sample-to-answer susceptibility determination in less than 30 minutes.

Example 15: MIC Intermediate Samples (Supplementary Material)

Figure 14:
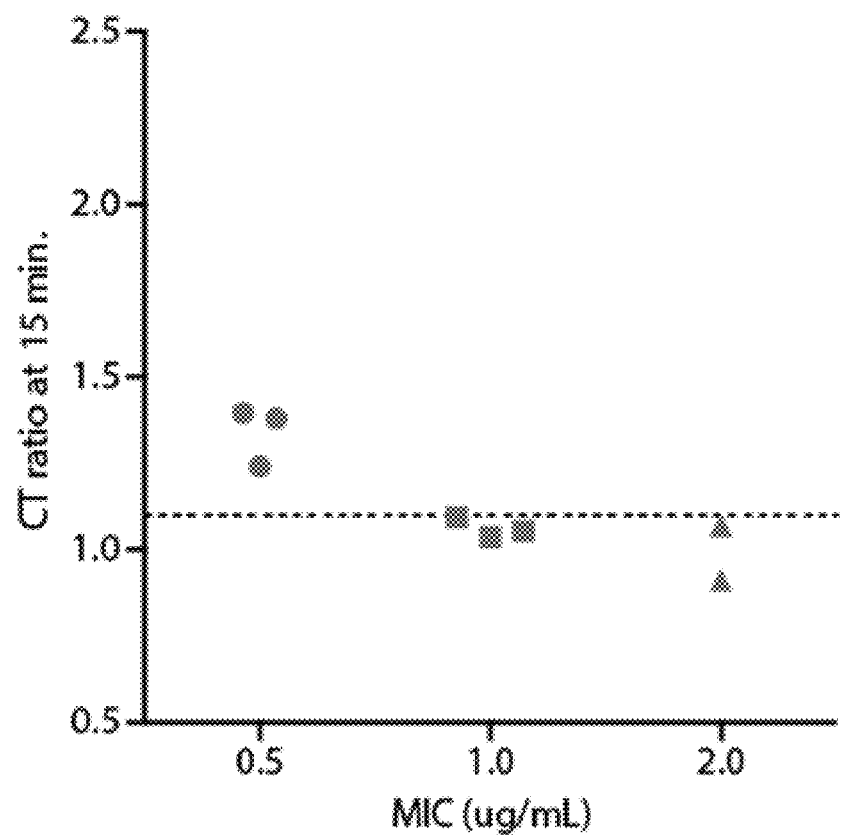
FIG. 14 shows CT values as determined by AST for near-intermediate MICs from dPCR 23S DNA concentration measurements.

To ensure that there were no special issues with bacteria with intermediate MICs, we used the dAST method on a small set of cip-intermediate isolates to better understand its performance (FIG. 14).

We analyzed 8 clinical isolates (2 operators with 4 isolates each) with intermediate and near-intermediate MICs using dPCR readout. We exposed these isolates with (1.0 µg/mL ciprofloxacin) and without antibiotics for 15 min and measured the nucleic acid concentrations with dPCR. Control-treated (CT) ratios were calculated from dPCR 23S DNA concentration measurements.

Isolates with MIC of 1.0 µg/mL (squares) and 2.0 µg/mL (triangles) are clustering very close to the threshold and slightly below, while isolates with MIC of 0.5 µg/mL (circles) are comfortably above the threshold and would be read as susceptible (FIG. 14). Thus, samples with intermediate MIC behave as expected. This also shows that MIC can be quantified by the methods provided herein.

FIG. 14 shows a changing response as a function of MIC. Thus, MIC can be inferred from the CT ratio determined by the methods provided herein.

Figure 15:
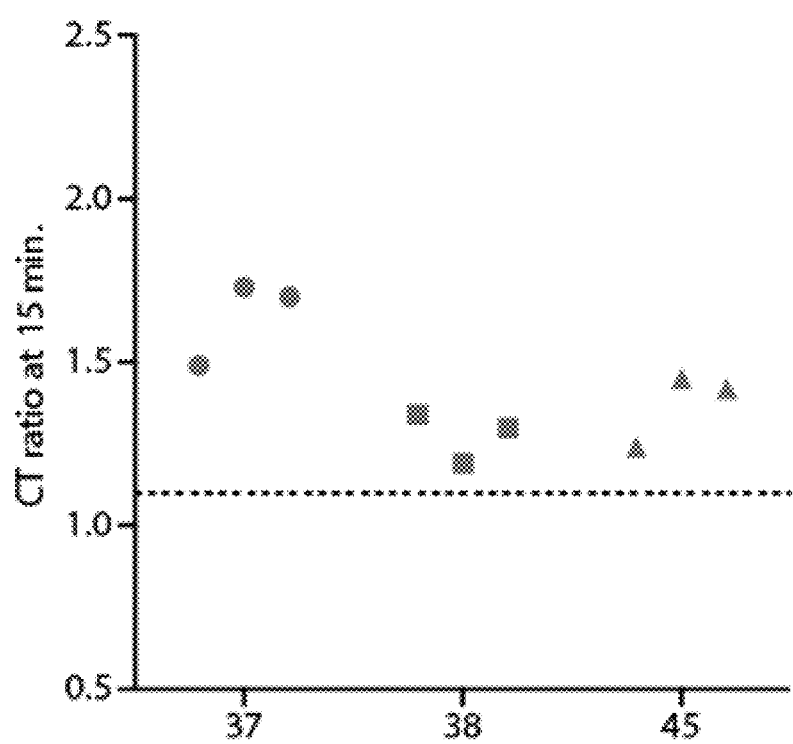
FIG. 15 shows the reproducibility of dAST method to determine CT ratios for clinical urine samples performed in triplicate. CT ratios were calculated from DNA concentration measurements using digital droplet PCR.

We performed the dAST method in triplicate on ciprofloxacin-susceptible samples (#37, #38, #45 from table 5). Control-treated (CT) ratios were calculated from DNA concentration measurements using digital droplet PCR. The results from each test are shown in FIG. 15 (#37 (circles), #38 (squares), #45 (triangles). We show a trend of changing response as a function of MIC. Thus, we can determine MIC of each microorganism from the CT ratio as determined by the dAST method taught herein.

Example 16: MIC Prediction

An *E. coli* strain isolated from a patient with a urinary tract infection, and with intermediate resistance to nitrofurantoin (minimum inhibitory concentration=64 µg/mL), was pre-cultured in Bacto Brain Heart Infusion media (BHI) and diluted into fresh media containing various concentrations of nitrofurantoin.

An *E. coli* strain isolated from a patient with a urinary tract infection, and with intermediate resistance to nitrofurantoin (minimum inhibitory concentration=64 µg/mL measured using standard CLSI protocols), was pre-cultured in Bacto Brain Heart Infusion media (BHI) and diluted to ~10^7 cells/mL as measured by optical density.

Figure 16:
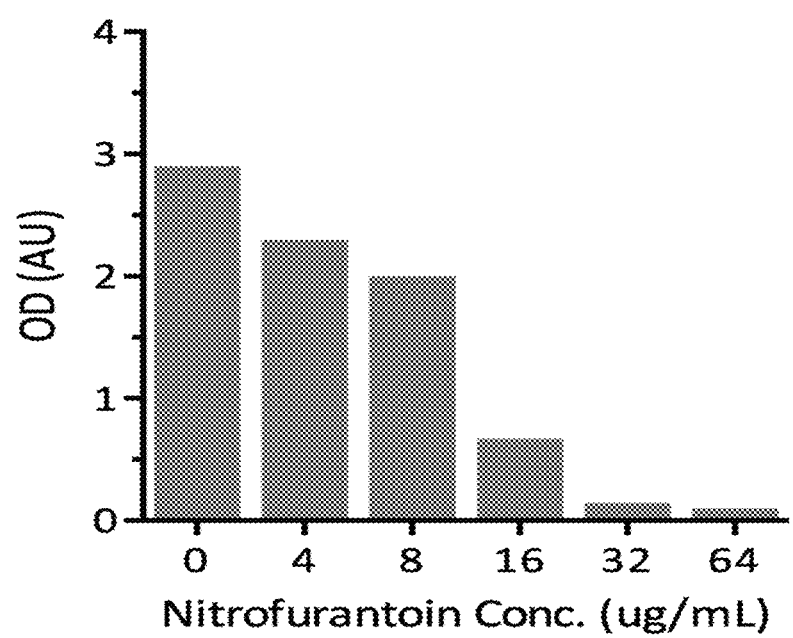
FIG. 16 shows the optical density of cultures (*E. coli* strain isolated from patient with UTI and with intermediate resistance to nitrofurantoin (MIC=64 μg/mL) grown in the presence of 0, 4, 8, 16, 32, or 64 μg/mL nitrofurantoin. The graph shows substantial inhibition of growth at 32 and 64 μg/mL of nitrofurantoin.

These cultures were grown for 2.5 hrs before growth was measured via optical density (FIG. 16). FIG. 16 shows substantial inhibition of growth at 32 and 64 μg/mL of nitrofurantoin.

Figure 17A:
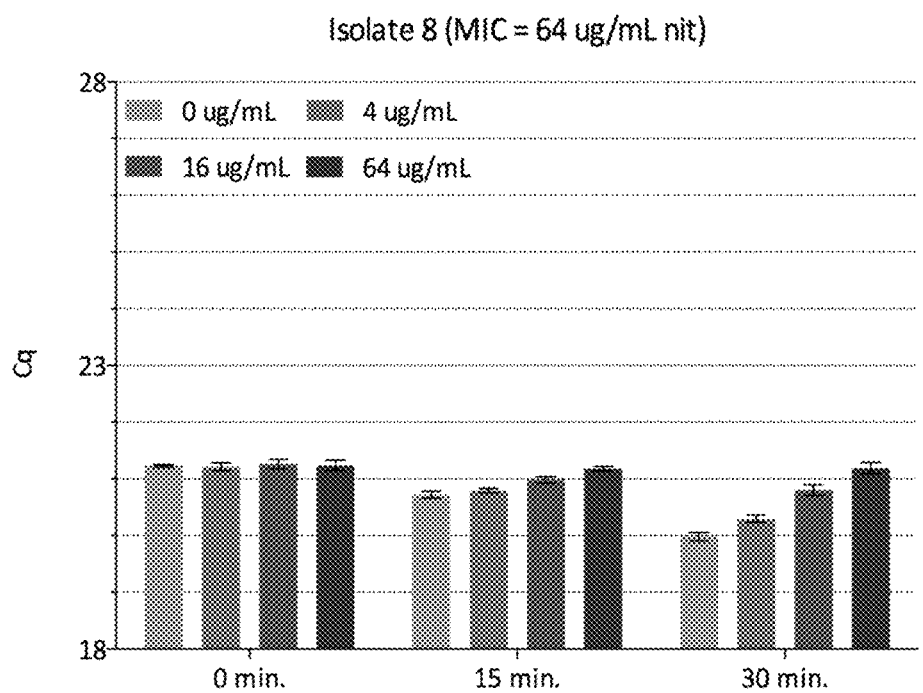
FIG. 17A shows the relationship between CT ratios over time obtained using digital LAMP and MIC for *E. coli* strain isolated from a patient with a urinary tract infection.
Figure 17B:
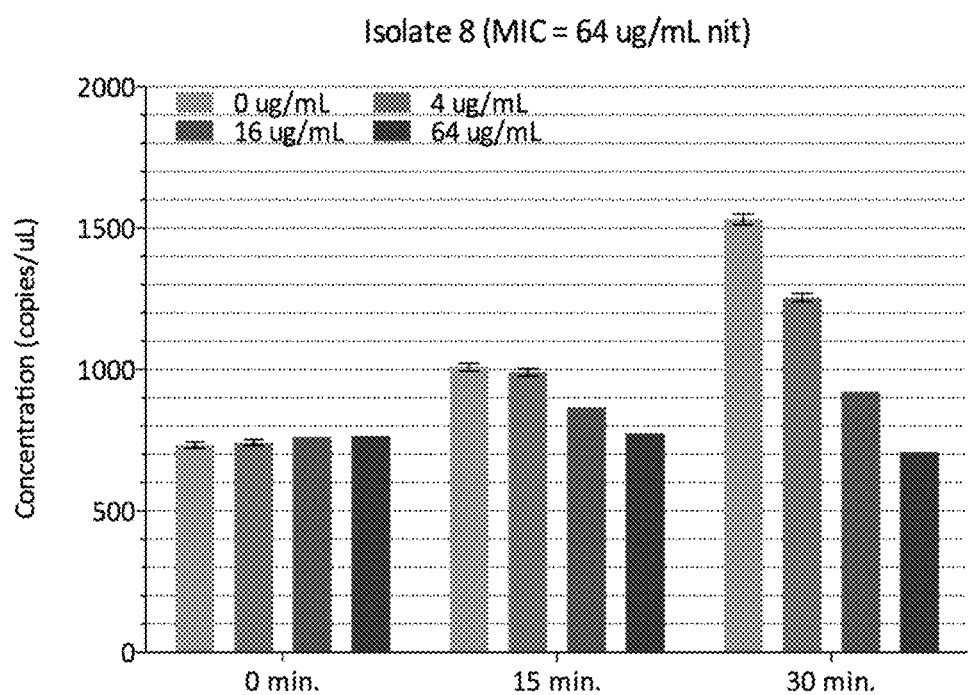
FIG. 17B shows the relationship between calculated concentrations over time obtained using digital PCR and MIC for *E. coli* strain isolated from a patient with a urinary tract infection.

500 uL aliquots of this culture were exposed to 0 (control), 4, 16, and 64 μg/mL nitrofurantoin in BHI at 37° C. with 750 rpm shaking. DNA from each aliquot was extracted at 0, 15, and 30 minutes by diluting a portion of the sample 10-fold in Epicentre Quick Extract DNA Extraction solution, following the manufacturer's protocol. DNA was quantified by qPCR (FIG. 17A) and by digital PCR (FIG. 17B).

These experiments indicate that digital quantification can be used to estimate minimal inhibitory concentrations of a given antibiotic. In other words, the extent of increase in DNA concentration measured by digital quantification methods for untreated (no ABX added) vs treated (ABX added) samples can be used to estimate how close a particular concentration of the ABX used for treatment is to the MIC.

In addition, these methods can be used to estimate MIC through the use of testing with as few as two antibiotic concentrations (along with an antibiotic-free control) and analysis of data by comparison to a standard curve generated using a broader range of antibiotic concentrations.

Example 17: Digital RPA

Other isothermal amplification methods can be used with digital methods for determining AST, as described herein. Digital RPA (recombinase polymerase reaction) was performed in the SlipChip digital platform as described in Feng et al., "Digital Isothermal Quantification of Nucleic Acids via Simultaneous Chemical Initiation of Recombinase Polymerase Amplification Reactions on SlipChip," *Analytical Chemistry* 2011 83:3533-3540.

Fluorescence of each well in the SlipChip was monitored in real-time as described in David A. Selck and Rustem F. Ismagilov. "Instrument for Real-Time Digital Nucleic Acid Amplification on Custom Microfluidic Devices" *PLoS One.* 2016 11(10): e0163060. doi:10.1371/journal.pone.0163060.

Figure 18:
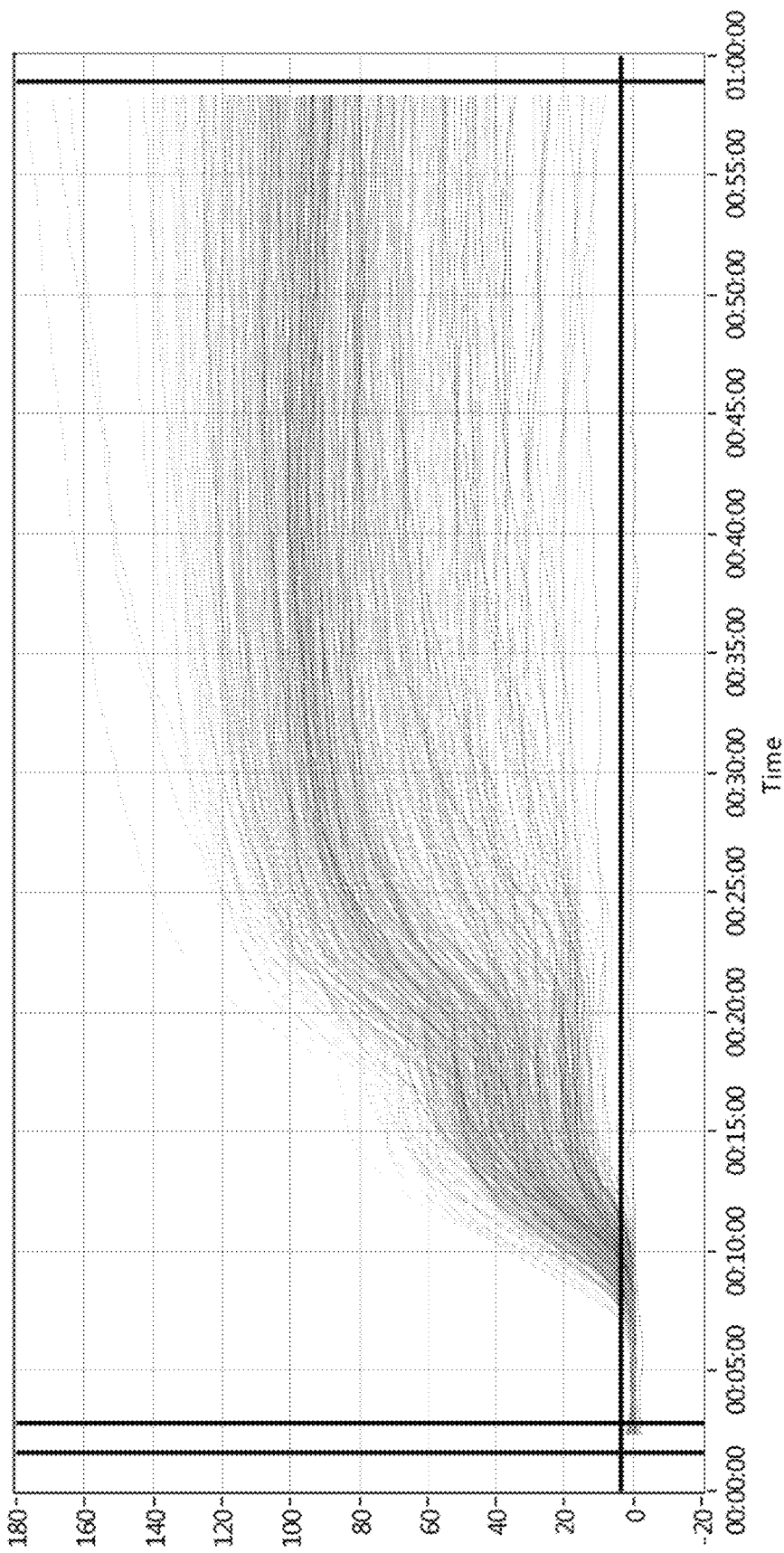
FIG. 18 shows plots of real-time fluorescent traces from RPA nucleic acid amplification reaction on a SlipChip. Each trace represents one compartment. 200 compartments are shown out of a possible 868.
Figure 19:
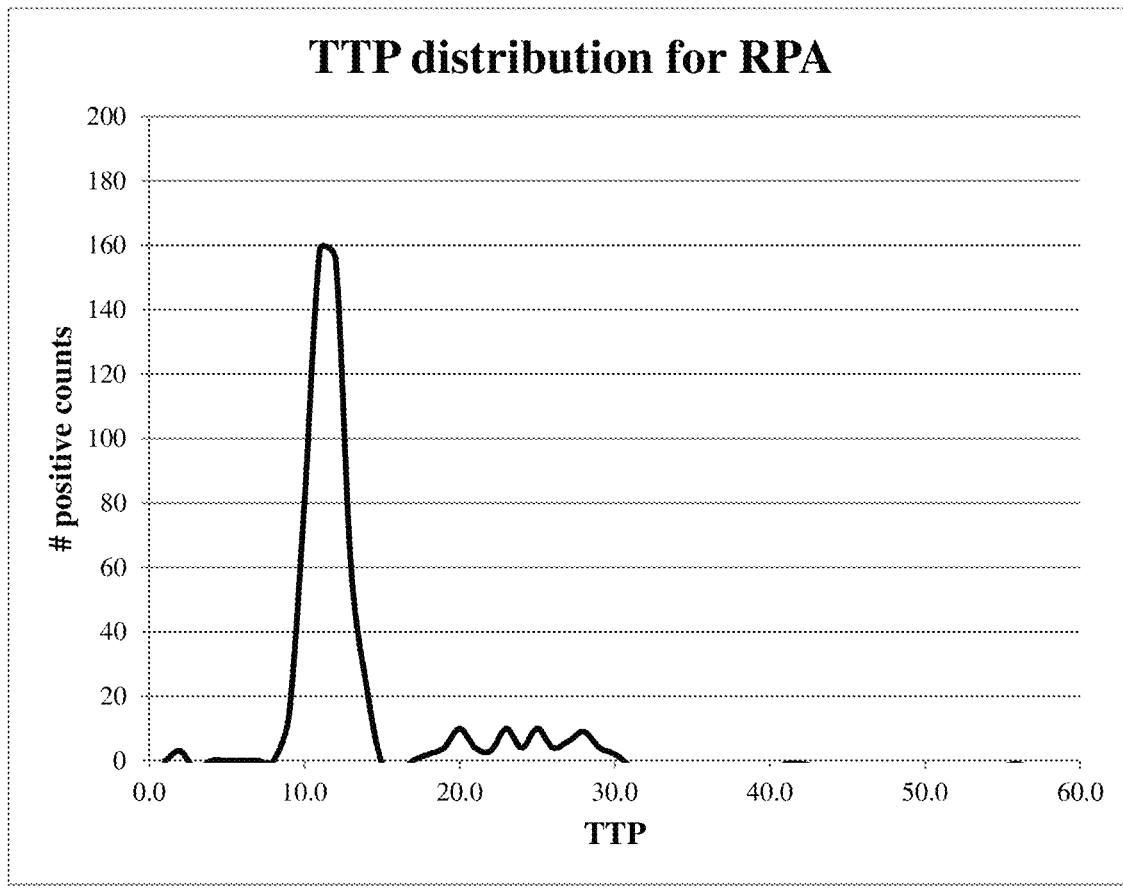
FIG. 19 shows a time-to-positive distribution from RPA nucleic acid amplification reaction on a SlipChip.

Time-to-positives are heterogeneous, similar to digital LAMP. FIG. 18 shows Real-time fluorescent traces from RPA nucleic acid amplification reaction on a SlipChip. Each trace represents one compartment. 200 compartments are shown out of a possible 868. Time-to-positive distribution from RPA nucleic acid amplification reaction on a SlipChip.

These data evidence that the methodologies described in detail herein are capable of being performed with isothermal amplification methods.

Other Embodiments

It is to be understood that the words which have been used are words of description rather than limitation, and that changes may be made within the purview of the appended claims without departing from the true scope and spirit of the invention in its broader aspects.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

The invention claimed is:

1. A method of comparing two samples, comprising
   distributing a first sample comprising a first amplifiable target molecule into a plurality of analysis regions to create a first population of digital samples;
   distributing a second sample comprising a second amplifiable target molecule into a plurality of analysis regions to create a second population of digital samples;
   initiating and performing an amplification reaction on the first population of digital samples and the second population of digital samples;
   detecting the presence or absence of amplification reaction in the first population and second population at a series of timepoints ($t_n$), said detection comprising identifying a number of analysis regions comprising a detectable signal in the first population ($^1P_n$) and identifying a number of analysis regions comprising a detectable signal in the second population ($^2P_n$) at each timepoint; and
   determining a ratio of $^1P_n$ to $^2P_n$ obtained at a timepoint around a time-to-positive maximum and prior to an endpoint of the amplification reaction, wherein $^1P_n$ is reflective of the endpoint concentration of the first target molecule in the first sample, and $^2P_n$ is reflective of the endpoint concentration of the second target molecule in the second sample, and the ratio of $^1P_n$ to $^2P_n$ is reflective of the relative endpoint concentration of first target molecule in the first sample to that of the second target molecule in the second sample, thereby comparing the two samples.

2. The method of claim 1, wherein said first amplifiable target molecule is from a first population of microorganisms not exposed to an antibiotic, and wherein said second amplifiable target molecule is from a second population of said microorganisms exposed to said antibiotic.

3. The method of claim 2, wherein said ratio is indicative of whether said microorganisms are resistant or susceptible to said antibiotic.

4. The method of claim 2, wherein a ratio of $^1P_n$ to $^2P_n$ greater than a predetermined threshold is indicative of said microorganisms being susceptible to said antibiotic.

5. The method of claim 2, wherein said first and second populations of microorganisms are from a single source sample partitioned into said first and second populations.

6. The method of claim 2, wherein the microorganisms are bacteria.

7. The method of claim 1, wherein said first amplifiable target molecule and said second amplifiable target molecule are the same.

8. The method of claim 1, wherein said first amplifiable target molecule and said second amplifiable target molecule are different.

9. The method of claim 1, wherein said series of timepoints ($t_n$) are separated by 15 seconds, 30 seconds, 60 seconds, 90 seconds, 120 seconds, or 150 seconds.

10. The method of claim 1, wherein said amplification reaction is an isothermal reaction.

11. The method of claim 1, wherein the detecting is carried out in less than 10 minutes, less than 9 minutes, less than 8 minutes, less than 7 minutes, or less than 6 minutes after initiating said amplification reaction.

12. The method of claim 1, wherein said step of detecting the presence or absence of amplification reaction at said timepoint at which said ratio of $^1P_n$ to $^2P_n$ is reflective of the relative endpoint concentration of first target molecule in the first sample to that of the second target molecule in the second sample is performed less than 10 minutes, less than 9 minutes, less than 8 minutes, less than 7 minutes, or less than 6 minutes after initiating said amplification reaction.

13. The method of claim 1, further comprising determining ratios of $^1P_n$ to $^2P_n$ at each of said series of timepoints around the time-to-positive maximum and prior to the endpoint of the amplification reaction.

14. The method of claim 1, wherein the amplifiable target molecule is a nucleic acid.

15. The method of claim 1, wherein the plurality of analysis regions comprising the first sample or the second sample comprises at least 100, 200, 500, or 1,000 analysis regions.

16. A method of assessing an antibiotic susceptibility in a population of microorganisms, comprising:
   distributing a first sample comprising an amplifiable target molecule from a first portion of a population of microorganisms among a plurality of analysis regions to create a first population of digital samples, wherein the first portion has not been exposed to an antibiotic;
   distributing a second sample comprising said amplifiable target molecule from a second portion of the population of microorganisms among a plurality of analysis regions to create a second population of digital samples, wherein the second portion has been exposed to said antibiotic;
   initiating and performing an amplification reaction on the first population of digital samples and the second population of digital samples, wherein said amplification reaction is capable of generating a detectable signal due to amplification of said amplifiable target molecule;
   detecting the presence or absence of said detectable signal in the first and second populations at a series of timepoints ($t_n$), said detection comprising identifying a number of analysis regions in the first population comprising said detectable signal ($^1P_n$) and identifying a number of detectable analysis regions in the second population comprising said detectable signal ($^2P_n$) at each timepoint;
   determining a ratio of $^1P_n$ to $^2P_n$ obtained at a timepoint wherein said detectable signals are still being generated in some of said plurality of analysis regions by said amplification reaction around a time-to-positive maximum and prior to an endpoint of the amplification reaction, wherein $^1P_n$ is reflective of the endpoint concentration of the first target molecule in the first sample, and $^2P_n$ is reflective of the endpoint concentration of the second target molecule in the second sample; and
   determining a susceptibility of the population of microorganisms to said antibiotic based on the ratio of $^1P_n$ to $^2P_n$.

17. The method of claim 16, wherein the determining the susceptibility comprises comparing the ratio of $^1P_n$ to $^2P_n$ to a threshold, wherein the ratio of $^1P_n$ to $^2P_n$ being below said threshold is indicative of resistance of said population of microorganisms to said antibiotic and wherein the ratio of $^1P_n$ to $^2P_n$ being above said threshold is indicative of susceptibility of said population of microorganisms to said antibiotic.

18. The method of claim 16, wherein the detecting is carried out in less than 10 minutes, less than 9 minutes, less than 8 minutes, less than 7 minutes, or less than 6 minutes after initiating said amplification reaction.

19. The method of claim 16, further comprising determining ratios of $^1P_n$ to $^2P_n$ at each of said series of timepoints around the time-to-positive maximum and prior to the endpoint of the amplification reaction.

20. The method of claim 16, wherein the amplifiable target molecule is less than 50 kb, less than 100 kb, less than 200 kb, or less than 400 kb from an origin of replication.

21. The method of claim 16, wherein said exposure of said second portion of the population of microorganisms to said antibiotic was for a period of no more than 30 minutes, no more than 20 minutes, no more than 15 minutes, or no more than 10 minutes.

* * * * *

SEQUENCE LISTING

```
<160> NUMBER OF SEQ ID NOS: 8

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tgccgtaact cgggagaag gc                                                  22

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tcaaggctca atgttcagtg tc                                                 22

<210> SEQ ID NO 3
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 3
ggcgttaagt tgcagggtat                                                    20

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tcacgaggcg ctacctaa                                                      18

<210> SEQ ID NO 5
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cggttcggtc ctccagttag tgttttcccg aaacccggtg atct                         44

<210> SEQ ID NO 6
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tagcggatga cttgtggctg gtttttcggg gagaaccagc tatc                         44

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
accttcaacc tgcccatg                                                      18

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gtgaaaggcc aatcaaacc                                                     19
```